United States Patent
Kamatani et al.

(10) Patent No.: US 10,109,807 B2
(45) Date of Patent: Oct. 23, 2018

(54) ORGANIC LIGHT-EMITTING ELEMENT AND DISPLAY APPARATUS

(71) Applicant: CANON KABUSHIKI KAISHA, Tokyo (JP)

(72) Inventors: Jun Kamatani, Tokyo (JP); Naoki Yamada, Inagi (JP); Tetsuya Kosuge, Yokohama (JP); Takayuki Horiuchi, Tokyo (JP); Shigemoto Abe, Yokohama (JP); Yosuke Nishide, Kawasaki (JP); Hirokazu Miyashita, Tokyo (JP); Kengo Kishino, Tokyo (JP); Akihito Saitoh, Gotemba (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 358 days.

(21) Appl. No.: 14/649,048

(22) PCT Filed: Dec. 24, 2013

(86) PCT No.: PCT/JP2013/085311
§ 371 (c)(1),
(2) Date: Jun. 2, 2015

(87) PCT Pub. No.: WO2014/104387
PCT Pub. Date: Jul. 3, 2014

(65) Prior Publication Data
US 2015/0333279 A1   Nov. 19, 2015

(30) Foreign Application Priority Data

Dec. 27, 2012 (JP) ................................ 2012-285621

(51) Int. Cl.
| H05B 33/14 | (2006.01) |
| H01L 51/50 | (2006.01) |
| G03G 15/04 | (2006.01) |
| C09K 11/06 | (2006.01) |
| C09B 57/10 | (2006.01) |
| C07F 15/00 | (2006.01) |
| H01L 51/00 | (2006.01) |
| C09B 57/00 | (2006.01) |

(52) U.S. Cl.
CPC ...... *H01L 51/0085* (2013.01); *C07F 15/0033* (2013.01); *C09B 57/00* (2013.01); *C09B 57/10* (2013.01); *C09K 11/06* (2013.01); *G03G 15/04036* (2013.01); *H05B 33/14* (2013.01); *C09K 2211/1007* (2013.01); *C09K 2211/1011* (2013.01); *C09K 2211/1029* (2013.01); *C09K 2211/1088* (2013.01); *C09K 2211/185* (2013.01); *H01L 51/0077* (2013.01); *H01L 51/0092* (2013.01); *H01L 51/5012* (2013.01); *H01L 51/5016* (2013.01); *H01L 51/5024* (2013.01)

(58) Field of Classification Search
CPC combination set(s) only.
See application file for complete search history.

(56) References Cited

U.S. PATENT DOCUMENTS

| 6,824,894 | B2 | 11/2004 | Takiguchi et al. |
| 7,078,115 | B2 | 7/2006 | Takiguchi et al. |
| 7,976,958 | B2 | 7/2011 | Takiguchi et al. |
| 8,330,153 | B2 | 12/2012 | Ooishi et al. |
| 8,519,384 | B2 | 8/2013 | Xia et al. |
| 9,466,804 | B2 * | 10/2016 | Kishino ................. C09K 11/06 |
| 2007/0231601 | A1 | 10/2007 | Nakasu et al. |
| 2008/0210930 | A1 | 9/2008 | Kamatani et al. |
| 2009/0159130 | A1 | 6/2009 | Eum et al. |
| 2009/0165860 | A1 | 7/2009 | Kim et al. |
| 2010/0102710 | A1 | 4/2010 | Cho et al. |
| 2010/0219407 | A1 | 9/2010 | Kamatani et al. |
| 2011/0227049 | A1 | 9/2011 | Xia et al. |
| 2012/0280218 | A1 * | 11/2012 | Watanabe ............ C07D 209/82 257/40 |
| 2014/0027757 | A1 | 1/2014 | Yamada et al. |
| 2014/0319505 | A1 * | 10/2014 | Nagayama .............. C09K 11/06 257/40 |
| 2015/0194609 | A1 * | 7/2015 | Nishide ................ C07D 405/14 257/40 |
| 2015/0364701 | A1 * | 12/2015 | Horiuchi ............. C07F 15/0033 315/291 |

(Continued)

FOREIGN PATENT DOCUMENTS

| JP | 3760508 B2 | 3/2006 |
| JP | 2009-114137 A | 5/2009 |
| JP | 2009-152568 A | 7/2009 |

(Continued)

OTHER PUBLICATIONS

Pending U.S. Appl. No. 14/758,683, filed Jun. 30, 2015 (not yet published).
Pending U.S. Appl. No. 14/648,494, filed May 29, 2015 (not yet published).
Pending U.S. Appl. No. 14/648,095, filed May 28, 2015 (not yet published).
Pending U.S. Appl. No. 14/761,049, filed Jul. 15, 2015 (not yet published).

(Continued)

*Primary Examiner* — Amanda L Aguirre
(74) *Attorney, Agent, or Firm* — Fitzpatrick, Cella, Harper & Scinto

(57) ABSTRACT

Provided is an organic light-emitting element having high luminous efficiency and a long lifetime. The organic light-emitting element includes a pair of electrodes and an organic compound layer placed between the pair of electrodes, in which the organic compound layer includes an iridium complex having a benzo[f]isoquinoline of a specific structure as a ligand and a metal complex compound of a specific structure.

20 Claims, 1 Drawing Sheet

(56) References Cited

U.S. PATENT DOCUMENTS

2015/0364702 A1* 12/2015 Abe .................. C09K 11/06 257/40

FOREIGN PATENT DOCUMENTS

| | | |
|---|---|---|
| JP | 2009-218571 A | 9/2009 |
| JP | 2009/275030 A | 11/2009 |
| JP | 2010-93048 A | 4/2010 |
| JP | 2012-229195 A | 11/2012 |
| JP | 2012-240952 A | 12/2012 |
| JP | 2012-243983 A | 12/2012 |
| WO | 2010/028151 A1 | 3/2010 |
| WO | 2012/141229 A1 | 10/2012 |

OTHER PUBLICATIONS

Pending U.S. Appl. No. 14/760,093, filed Jul. 9, 2015 (not yet published).

Pending U.S. Appl. No. 14/764,204, filed Jul. 29, 2015 (not yet published).

Pending U.S. Appl. No. 14/764,376, filed Jul. 29, 2015 (not yet published).

Chinese Office Action issued in corresponding application No. 201380067401.2 dated Apr. 19, 2016—14 pages with English translation.

Fletcher, S., et al., "Oxidation of p-Aminophenols and Formal Radical Cyclization onto Benzene Rings: Formation of Benzo-Fused Nitrogen Heterocycles," Organic Letters, vol. 7, No. 1, pp. 23-26 (2005).

Eloy, F., et al., "Sur une Méthode Nouvelle de Sythèdes Aza-2 Phénanthrènes (Benzo[f]isoquinoléines) (Note de Laboratoire)," Chimica Therapeutica, vol. 6, No. 1, pp. 48-49 (1971).

Wiley, R., et al., "Substitued 4,7-Phenanthrolines and Benzo[f]quinolines as Scintillation Solutes," The Journal of Organic Chemistry, vol. 23, No. 2, pp. 268-271 (1958).

Roesch, K., et al., "Synthesis of Isoquinolines and Pyridines by the Palladium-Catalyzed Iminoannulation of Internal Alkynes," The Journal of Organic Chemistry, vol. 66, No. 24, pp. 8042-8051 (2001).

* cited by examiner

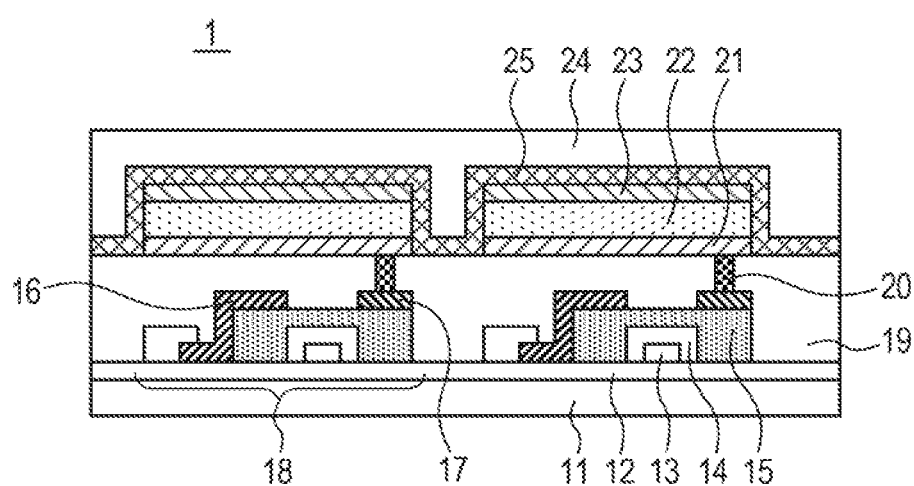

ORGANIC LIGHT-EMITTING ELEMENT AND DISPLAY APPARATUS

TECHNICAL FIELD

The present invention relates to an organic light-emitting element and a display apparatus.

BACKGROUND ART

An organic light-emitting element (also referred to as "organic electroluminescence element" or "organic EL element") is an electronic element including a pair of electrodes and an organic compound layer placed between the pair of electrodes. An electron and a hole are injected from the pair of electrodes, and then the electron and the hole recombine in the organic compound layer to produce an exciton of a luminous organic compound. The organic light-emitting element emits light upon return of the exciton to its ground state.

Recent development of the organic light-emitting elements is significant and the developed elements have, for example, the following features. The light-emitting elements can be driven at low voltages, emit light beams having various wavelengths, have high-speed responsiveness, and can be reduced in thickness and weight.

By the way, the creation of a compound suitable for the organic light-emitting element has been vigorously performed heretofore. This is because the creation of a compound having an excellent element lifetime characteristic is important for providing a high-performance organic light-emitting element.

An organometallic complex to be used as a phosphorescent light-emitting material is included in the compounds created heretofore. The organometallic complex is specifically, for example, an iridium complex described in PTL 1. In addition, another example of the metal complex to be used as a constituent material for the organic light-emitting element is such a metal complex as described in PTL 2. Meanwhile, a metal complex disclosed in PTL 3 or PTL 4 is available as a metal complex to be incorporated as a host into an emission layer together with the iridium complex.

CITATION LIST

Patent Literature

PTL 1: Japanese Patent Application Laid-Open No. 2009-114137
PTL 2: Japanese Patent No. 3760508
PTL 3: Japanese Patent Application Laid-Open No. 2009-152568
PTL 4: Japanese Patent Application Laid-Open No. 2009-218571
PTL 5: International Publication No. 2010/028151

Non Patent Literature

NPL 1: J. Org. Chem., Vol. 66, No. 24, pp. 8042-8051 (2001)
NPL 2: Org. Lett., Vol. 7, No. 1, pp. 23-26 (2005)
NPL 3: Chimica Therapeutica, Vol. 6, No. 1, pp. 48-49 (1971)
NPL 4: J. Org. Chem., Vol. 23, pp. 268-271 (1958)

SUMMARY OF INVENTION

Solution to Problem

According to one embodiment of the present invention, there is provided an organic light-emitting element, including:

a pair of electrodes; and
an organic compound layer placed between the pair of electrodes,
in which the organic compound layer includes an iridium complex represented by the following general formula [1] and a metal complex compound represented by the following general formula [5].

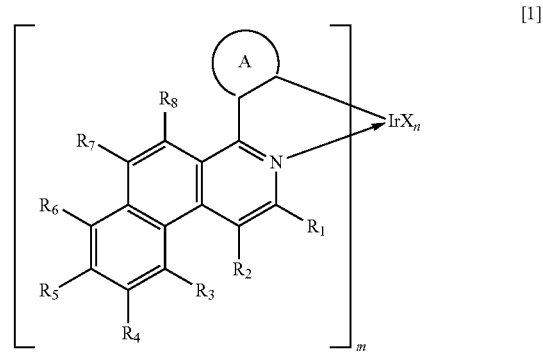

[1]

In the formula [1], $R_1$ to $R_8$ each represent a hydrogen atom, a halogen atom, an alkyl group, an alkoxy group, a substituted amino group, a substituted or unsubstituted aromatic hydrocarbon group, or a substituted or unsubstituted heteroaromatic group.

m represents an integer of 1 to 3 and n represents an integer of 0 to 2, provided that m+n equals 3.

A ring A includes a substituted or unsubstituted aromatic group, represents a cyclic structure selected from the group consisting of a benzene ring, a naphthalene ring, a phenanthrene ring, a fluorene ring, a 9,9-spirobifluorene ring and a chrysene ring, and is covalently bonded to a benzo[f]isoquinoline skeleton and an Ir metal, and the ring A may further have a substituent.

X represents a bidentate ligand.

A partial structure $IrX_n$ includes any one of structures represented by the following general formulae [2] to [4].

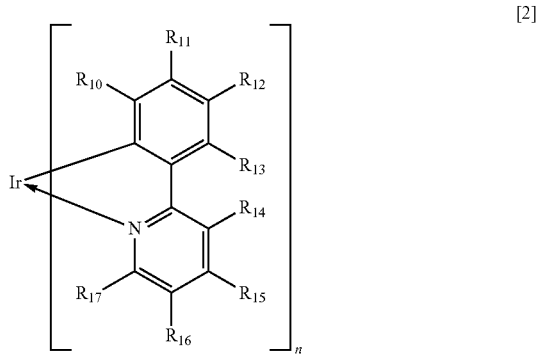

[2]

-continued

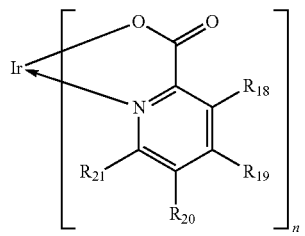
[3]

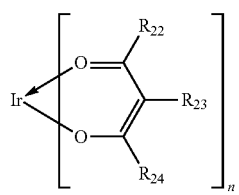
[4]

In the formulae [2] to [4], $R_{10}$ to $R_{24}$ each represent a hydrogen atom, a halogen atom, a substituted or unsubstituted alkyl group, an alkoxy group, an aryloxy group, an aralkyl group, a substituted amino group, a substituted or unsubstituted aromatic hydrocarbon group, or a substituted or unsubstituted heteroaromatic group, and when n represents 2, multiple substituents represented by any one of $R_{10}$ to $R_{24}$ may be identical to or different from each other.

$$ML_2 \quad [5]$$

In the formula [5], M represents a divalent metal atom selected from the group consisting of beryllium, magnesium and zinc.

L represents a bidentate ligand.

When M represents beryllium or magnesium, a partial structure ML includes any one of structures represented by the following general formulae [6] to [11], and when M represents zinc, the partial structure ML includes any one of the structures represented by the following general formulae [6] to [9].

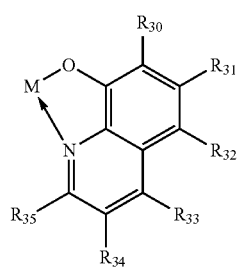
[6]

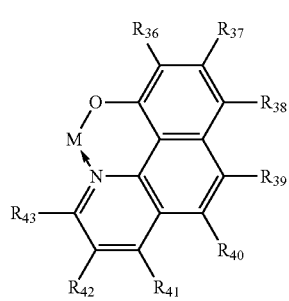
[7]

-continued

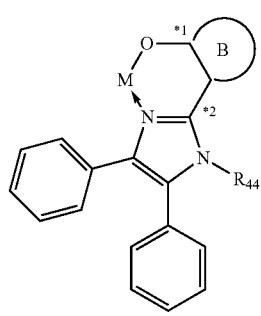
[8]

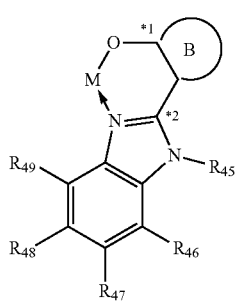
[9]

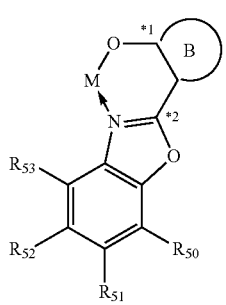
[10]

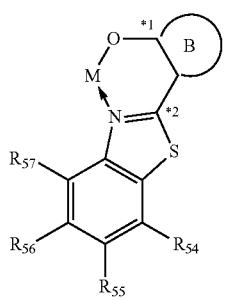
[11]

In the formulae [6] to [11], $R_{30}$ to $R_{57}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

In the formulae [8] to [11], a ring B includes any one of cyclic structures represented by the following general formulae [12] to [14].

*1 represents a bonding position with an oxygen atom and *2 represents a bonding position with a carbon atom in a heterocyclic five-membered ring skeleton.

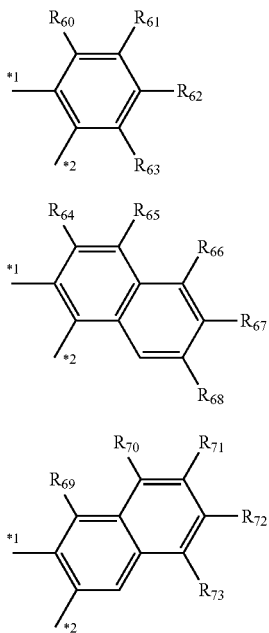

[12]

[13]

[14]

In the formulae [12] to [14], $R_{60}$ to $R_{73}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

Further features of the present invention will become apparent from the following description of exemplary embodiments with reference to the attached drawing.

BRIEF DESCRIPTION OF DRAWINGS

FIGURE is a schematic sectional view illustrating an example of a display apparatus including an organic light-emitting element according to an embodiment of the present invention and an active element connected to the organic light-emitting element.

DESCRIPTION OF EMBODIMENTS

PTL 1 exemplifies a zinc complex as a host to be incorporated into an emission layer together with a phosphorescent light-emitting material. However, the zinc complex itself has low luminous efficiency. In addition, the metal complex described in PTL 2 has not been used as a host to be incorporated into the emission layer together with the phosphorescent light-emitting material. Further, the luminous efficiency of an organic light-emitting element obtained by incorporating the metal complex disclosed in PTL 3 or PTL 4 as a host into its emission layer is also low.

Therefore, none of the organic light-emitting elements disclosed in PTLS 1 to 4 has been able to obtain high luminous efficiency and a high lifetime characteristic.

The present invention has been made to solve the problems, and an object of the present invention is to provide an organic light-emitting element having high luminous efficiency and a long lifetime.

Hereinafter, the present invention is described in detail.

(1) Organic Light-Emitting Element

An organic light-emitting element of the present invention is a light-emitting element including at least: an anode and a cathode as a pair of electrodes opposite to each other; and an organic compound layer placed between the pair of electrodes. In addition, the organic light-emitting element of the present invention includes, in the organic compound layer, an iridium complex represented by the following general formula [1] and a metal complex compound represented by the following general formula [5].

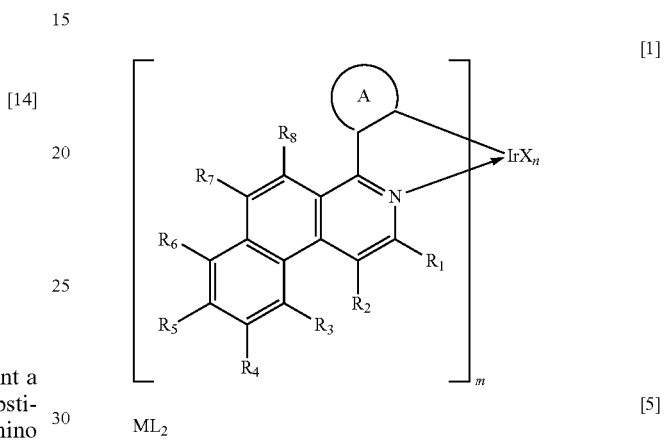

$ML_2$  [5]

Details about the iridium complex represented by the general formula [1] and the metal complex compound represented by the general formula [5] are described later.

The element construction of the organic light-emitting element of the present invention is, for example, a multi-layer-type element construction obtained by sequentially laminating, on a substrate, electrode layers and an organic compound layer described in each of the following constructions (1) to (6). It should be noted that in each of the element constructions, the organic compound layer necessarily includes an emission layer including a light-emitting material.

(1) Anode/emission layer/cathode
(2) Anode/hole-transporting layer/emission layer/electron-transporting layer/cathode
(3) Anode/hole-transporting layer/emission layer/electron-transporting layer/electron-injecting layer/cathode
(4) Anode/hole-injecting layer/hole-transporting layer/emission layer/electron-transporting layer/cathode
(5) Anode/hole-injecting layer/hole-transporting layer/emission layer/electron-transporting layer/electron-injecting layer/cathode
(6) Anode/hole-transporting layer/electron-blocking layer/emission layer/hole-blocking layer/electron-transporting layer/cathode It should be noted that those element construction examples are only very basic element constructions and the element construction of the organic light-emitting element of the present invention is not limited thereto.

For example, the following various layer constructions can each be adopted: an insulating layer, an adhesion layer, or an interference layer is provided at an interface between an electrode and the organic compound layer, the electron-transporting layer or the hole-transporting layer is constituted of two layers having different ionization potentials, or the emission layer is constituted of two layers including different light-emitting materials.

In the present invention, the embodiment according to which light output from the emission layer is extracted (element configuration) may be the so-called bottom emission type in which the light is extracted from an electrode on a side closer to the substrate or may be the so-called top emission type in which the light is extracted from a side opposite to the substrate. In addition, a double-face extraction type in which the light is extracted from each of the side closer to the substrate and the side opposite to the substrate can be adopted.

Of the element constructions (1) to (6), the construction (6) is preferred because the construction includes both the electron-blocking layer and the hole-blocking layer. In other words, the construction (6) including the electron-blocking layer and the hole-blocking layer provides an organic light-emitting element that does not cause any carrier leakage and has high luminous efficiency because both carriers, i.e., a hole and an electron can be trapped in the emission layer with reliability.

In the organic light-emitting element of the present invention, the iridium complex represented by the general formula [1] and the metal complex compound represented by the general formula [5] are preferably incorporated into the emission layer out of the organic compound layer. In this case, the emission layer includes at least the iridium complex represented by the general formula [1] and the metal complex compound represented by the general formula [5]. The applications of the compounds to be incorporated into the emission layer in this case vary depending on their content concentrations in the emission layer. Specifically, the compounds are classified into a main component and a sub-component depending on their content concentrations in the emission layer.

The compound serving as the main component is a compound having the largest weight ratio (content concentration) out of the group of compounds to be incorporated into the emission layer and is a compound also called a host. In addition, the host is a compound present as a matrix around the light-emitting material in the emission layer, and is a compound mainly responsible for the transport of a carrier to the light-emitting material and the donation of an excitation energy to the light-emitting material.

In addition, the compound serving as the sub-component is a compound except the main component and can be called a guest (dopant), a light emission assist material, or a charge-injecting material depending on a function of the compound. The guest as one kind of sub-component is a compound (light-emitting material) responsible for main light emission in the emission layer. The light emission assist material as one kind of sub-component is a compound that assists the light emission of the guest and is a compound having a smaller weight ratio (content concentration) in the emission layer than that of the host. The light emission assist material is also called a second host by virtue of its function.

The concentration of the guest with respect to the host is 0.01 wt % or more and 50 wt % or less, preferably 0.1 wt % or more and 20 wt % or less with reference to the total amount of the constituent materials for the emission layer. The concentration of the guest is particularly preferably 10 wt % or less from the viewpoint of preventing concentration quenching.

In the present invention, the guest may be uniformly incorporated into the entirety of the layer in which the host serves as a matrix, or may be incorporated so as to have a concentration gradient. In addition, the guest may be partially incorporated into a specific region in the emission layer to make the layer a layer having a region free of the guest and formed only of the host.

In the present invention, the following aspect is preferred: both the iridium complex represented by the general formula [1] and the metal complex compound represented by the general formula [5] are incorporated as the guest and the host, respectively, into the emission layer. In this case, in addition to the iridium complex represented by the general formula [1], another phosphorescent light-emitting material may be further incorporated into the emission layer for assisting the transfer of an exciton or a carrier.

In addition, a compound different from the metal complex compound represented by the general formula [5] may be further incorporated as the second host into the emission layer for assisting the transfer of the exciton or the carrier. In the present invention, the (light emission) assist material is preferably an iridium complex, provided that the iridium complex to be used as the (light emission) assist material is an iridium complex except the iridium complex represented by the general formula [1].

(2) Iridium Complex

Next, the iridium complex as one constituent material for the organic light-emitting element of the present invention is described. The iridium complex as one constituent material for the organic light-emitting element of the present invention is a compound represented by the following general formula [1].

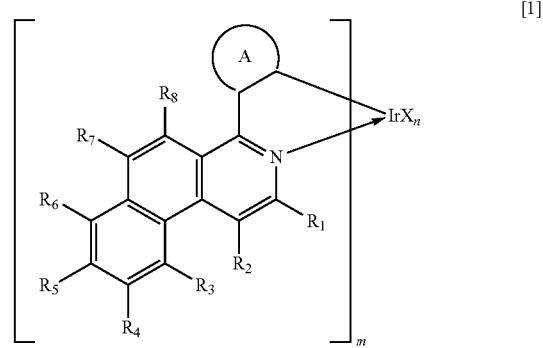

[1]

In the formula [1], $R_1$ to $R_8$ each represent a hydrogen atom, a halogen atom, an alkyl group, an alkoxy group, an aryloxy group, a trifluoromethyl group, a cyano group, a substituted or unsubstituted aromatic hydrocarbon group, or a substituted or unsubstituted heteroaromatic group.

Specific examples of the halogen atom represented by any one of $R_1$ to $R_8$ include fluorine, chlorine, bromine, and iodine atoms.

The alkyl group represented by any one of $R_1$ to $R_8$ is preferably an alkyl group having 1 or more and 6 or less carbon atoms. Specific examples of the alkyl group having 1 or more and 6 or less carbon atoms include a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group. It should be noted that part or all of hydrogen atoms in the alkyl group may be substituted with a fluorine atom as in a trifluoromethyl group or the like. Of those alkyl groups, a methyl group or a tert-butyl group is particularly preferred.

Specific examples of the alkoxy group represented by any one of $R_1$ to $R_8$ include, but, of course, not limited to, a methoxy group, an ethoxy group, an i-propoxy group, an n-butoxy group, a tert-butoxy group, a 2-ethyl-octyloxy group, and a benzyloxy group. Of those alkoxy groups, a methoxy group or an ethoxy group is preferred.

Specific examples of the aromatic hydrocarbon group represented by any one of $R_1$ to $R_8$ include, but, of course, not limited to, a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group. Of those aromatic hydrocarbon groups, a phenyl group, a naphthyl group, a fluorenyl group, or a biphenyl group is preferred, and a phenyl group is more preferred.

Specific examples of the heteroaromatic group represented by any one of $R_1$ to $R_8$ include, but, of course, not limited to, a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group.

Each of the aromatic hydrocarbon group and heteroaromatic group represented by $R_1$ to $R_8$ may further have a substituent. Specific examples thereof include: alkyl groups such as a methyl group, an ethyl group, and a propyl group; aralkyl groups such as a benzyl group; aryl groups such as a phenyl group, a biphenyl group, and a tetrakis(9,9-dimethylfluorenyl) group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, and a propoxyl group; aryloxyl groups such as a phenoxyl group; halogen atoms such as fluorine, chlorine, bromine, and iodine atoms; and a cyano group.

In the formula [1], m represents an integer of 1 to 3 and n represents an integer of 0 to 2, provided that m+n equals 3.

In the formula [1], the ring A represents a cyclic structure selected from a benzene ring, a naphthalene ring, a fluorene ring, a phenanthrene ring, a 9,9-spirobifluorene ring, and a chrysene ring. The ring A is bonded to a benzo[f]isoquinoline skeleton and an Ir metal with respective covalent bonds.

It should be noted that the ring A may further have a substituent. Specific examples thereof include: alkyl groups such as a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group; a halogen atom selected from fluorine, chlorine, bromine, and iodine atoms; alkoxy groups such as a methoxy group, an ethoxy group, an i-propoxy group, an n-butoxy group, and a tert-butoxy group; aryloxy groups such as a phenoxy group, a 4-tert-butylphenoxy group, and a thienyloxy group; substituted amino groups such as an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphtylamino group, an N,N-difluorenylamino group, an N-phenyl-N-tolylamino group, an N,N-ditolylamino group, an N-methyl-N-phenylamino group, an N,N-dianisoylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group; aromatic hydrocarbon groups such as a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, a terphenyl group, a dimethylphenyl group, a tert-butylphenyl group, a cyanophenyl group, a trifluoromethylphenyl group, and a methoxyphenyl group; heteroaromatic groups such as a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, an oxadiazolyl group, and a dimethylpyridyl group; a cyano group; and a trifluoromethyl group.

In the formula [1], $R_1$ to $R_8$ each preferably represent a hydrogen atom, an alkyl group having 1 to 4 carbon atoms, or a phenyl group that may be substituted with an alkyl group having 1 to 4 carbon atoms.

In the formula [1], X represents a bidentate ligand. In the present invention, a partial structure $IrX_n$ of the complex including X is specifically any one of the structures represented by the following general formulae [2] to [4].

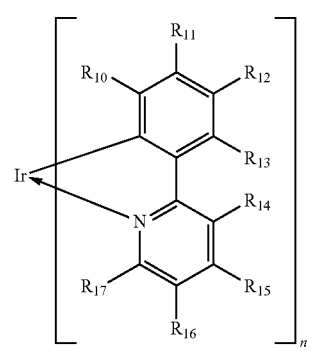

[2]

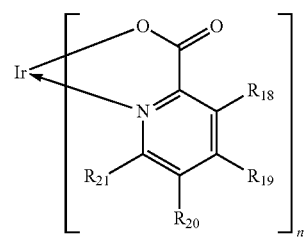

[3]

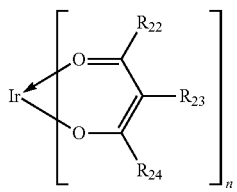

In the formulae [2] to [4], $R_{10}$ to $R_{24}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

Specific examples of the halogen atom, alkyl group, alkoxy group, trifluoromethyl group, cyano group, aromatic hydrocarbon group, and heteroaromatic group represented by $R_{10}$ to $R_{24}$ are the same as the specific examples in $R_1$ to $R_8$ in the general formula [1]. In addition, when the substituent represented by any one of $R_{10}$ to $R_{24}$ is an aromatic hydrocarbon group or a heteroaromatic group, specific examples of the substituent that the substituent may further have are the same as the specific examples in $R_1$ to $R_8$ in the general formula [1].

The substituent represented in any one of the formulae [2] to [4], i.e., any one of $R_{10}$ to $R_{24}$ preferably represents a hydrogen atom, an alkyl group having 1 to 4 carbon atoms, or a phenyl group that may be substituted with an alkyl group having 1 to 4 carbon atoms.

In the iridium complex represented by the general formula [1], m preferably represents 2 and n preferably represents 1.

In addition, the iridium complex represented by the general formula [1] is preferably an iridium complex represented by the following general formula [15].

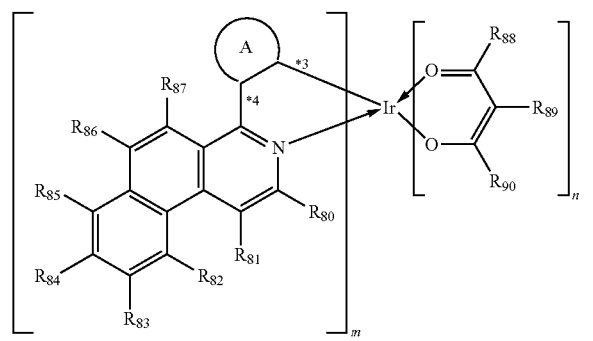

In the formula [15], $R_{80}$ to $R_{90}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

Specific examples of the halogen atom, alkyl group, alkoxy group, trifluoromethyl group, cyano group, aromatic hydrocarbon group, and heteroaromatic group represented by $R_{80}$ to $R_{90}$ are the same as the specific examples of $R_1$ to $R_8$ in the general formula [1]. In addition, when the substituent represented by any one of $R_{80}$ to $R_{90}$ is an aromatic hydrocarbon group or a heteroaromatic group, specific examples of the substituent that the aromatic hydrocarbon group and the heteroaromatic group may each further have are the same as the specific examples of $R_1$ to $R_8$ in the general formula [1].

The substituents represented in the formula [15], i.e., $R_{80}$ to $R_{90}$ each preferably represent a hydrogen atom, an alkyl group having 1 to 4 carbon atoms, or a phenyl group that may be substituted with an alkyl group having 1 to 4 carbon atoms.

In the formula [15], m represents an integer of 1 to 3 and n represents an integer of 0 to 2, provided that m+n equals 3.

In the formula [15], *3 represents a bond between the ring A and the Ir metal and *4 represents a bond between the ring A and a carbon atom at the 1-position of the benzo[f]isoquinoline skeleton.

In the formula [15], the ring A is a substituted or unsubstituted aromatic ring, is specifically a partial structure represented by any one of the following general formulae [16] to [20], and is preferably a structure represented by the general formula [16].

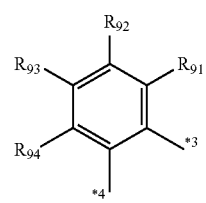

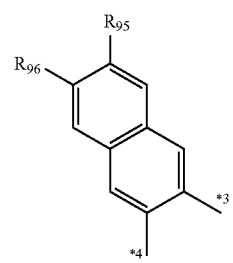

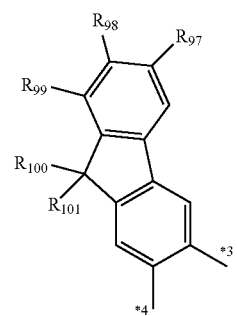

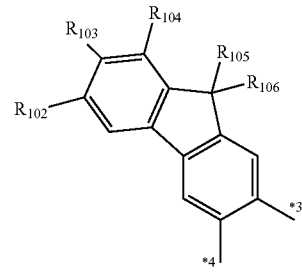

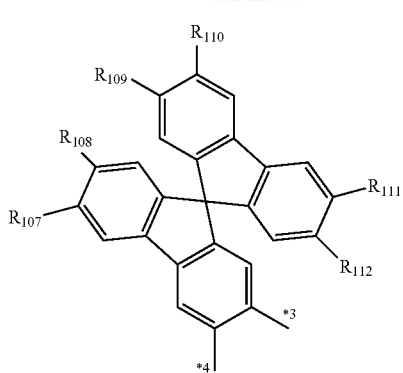

In the formulae [16] to [20], $R_{91}$ to $R_{112}$ each represent a hydrogen atom, a halogen atom, an alkyl group, an alkoxy group, a trifluoromethyl group, a cyano group, a substituted or unsubstituted aromatic hydrocarbon group, or a substituted or unsubstituted heteroaromatic group.

Specific examples of the halogen atom, alkyl group, alkoxy group, trifluoromethyl group, cyano group, aromatic hydrocarbon group, and heteroaromatic group represented by $R_{91}$ to $R_{112}$ are the same as the specific examples of $R_1$ to $R_8$ in the general formula [1]. In addition, when the substituent represented by any one of $R_{91}$ to $R_{112}$ is an aromatic hydrocarbon group or a heteroaromatic group, specific examples of the substituent which the substituent may further have are the same as the specific examples of $R_1$ to $R_8$ in the general formula [1].

The substituent represented in any one of the formulae [16] to [20], i.e., any one of $R_{91}$ to $R_{112}$ preferably represents a hydrogen atom, an alkyl group having 1 to 4 carbon atoms, or a phenyl group that may be substituted with an alkyl group having 1 to 4 carbon atoms.

In the formulae [16] to [20], *3 represents a bonding position with the Ir metal and *4 represents a bonding position with the carbon atom at the 1-position in the benzo[f]isoquinoline skeleton.

In addition, the iridium complex represented by the general formula [1] is particularly preferably an iridium complex represented by the following general formula [21].

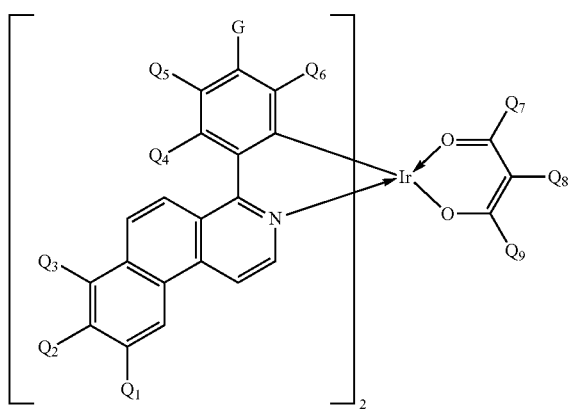

In the formula [21], $Q_1$ to $Q_9$ each represent a hydrogen atom, a halogen atom, an alkyl group, an alkoxy group, a trifluoromethyl group, or a cyano group. Specific examples of the halogen atom, alkyl group, and alkoxy group represented by $Q_1$ to $Q_9$ are the same as the specific examples in $R_1$ to $R_8$ in the general formula [1].

The substituents represented in the formula [21], i.e., $Q_1$ to $Q_9$ each preferably represent a hydrogen atom, an alkyl group having 1 to 4 carbon atoms, or a phenyl group that may be substituted with an alkyl group having 1 to 4 carbon atoms.

In the formula [21], G represents a hydrogen atom, a halogen atom, an alkyl group, an alkoxy group, a trifluoromethyl group, a cyano group, or a substituted or unsubstituted phenyl group. Specific examples of the halogen atom, alkyl group, and alkoxy group represented by G, and the substituent that the phenyl group represented by G may further have are the same as the specific examples in $R_1$ to $R_8$ in the general formula [1].

By the way, the compounds to be incorporated, if nothing else, into the organic light-emitting element of the present invention, specifically, the iridium complex and the metal complex to be described later can each be appropriately changed in luminous wavelength, band gap, and HOMO-LUMO by providing its basic skeleton with a specific substituent. It should be noted that providing an excessively large number of substituents reduces its sublimability.

From the foregoing viewpoint, particularly when any one of $R_1$ to $R_8$ in the general formula [1] is provided with a substituent, the substituent is preferably a substituent having a molecular weight of 100 or less such as an alkyl group having 1 to 6 carbon atoms, a methoxy group, an ethoxy group, a phenyl group, a pyridyl group, a fluorine group, or a cyano group.

(3) Metal Complex Compound Serving as Host

Next, the metal complex compound to be used as the host of the emission layer in the organic light-emitting element of the present invention is described. The metal complex compound serving as the host to be incorporated into the organic light-emitting element of the present invention is specifically a compound represented by the following general formula [5].

$$ML_2 \quad [5]$$

In the formula [5], M represents a divalent metal atom selected from beryllium, magnesium, and zinc.

L represents a bidentate ligand.

When M represents beryllium or magnesium, the partial structure ML is any one of the structures represented by the following general formulae [6] to [11]. In addition, when M represents zinc, the partial structure ML is any one of the structures represented by the following general formulae [6] to [9].

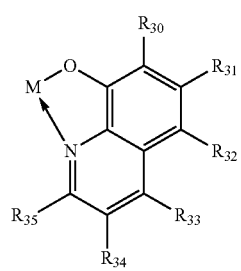

[6]

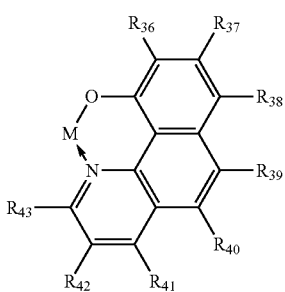

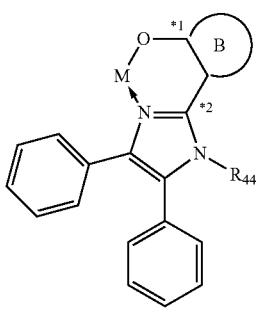

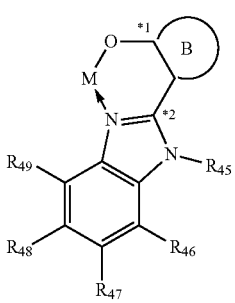

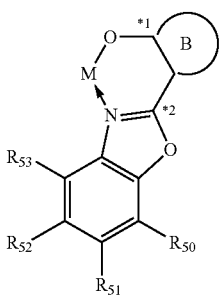

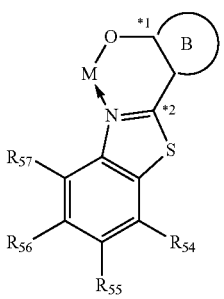

In the formulae [6] to [11], $R_{30}$ to $R_{57}$ each represent a hydrogen atom, a halogen atom, a substituted or unsubstituted alkyl group, an alkoxy group, an aryloxy group, an aralkyl group, a substituted amino group, a substituted or unsubstituted aromatic hydrocarbon group, or a substituted or unsubstituted heteroaromatic group.

Specific examples of the halogen atom represented by any one of $R_{30}$ to $R_{57}$ include fluorine, chlorine, bromine, and iodine atoms.

The alkyl group represented by any one of $R_{30}$ to $R_{57}$ is preferably an alkyl group having 1 or more and 6 or less carbon atoms. Specific examples of the alkyl group having 1 or more and 6 or less carbon atoms include a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group. Of those alkyl groups, a methyl group or a tert-butyl group is particularly preferred.

Specific examples of the alkoxy group represented by any one of $R_{30}$ to $R_{57}$ include, but, of course, not limited to, a methoxy group, an ethoxy group, an i-propoxy group, an n-butoxy group, a tert-butoxy group, a 2-ethyl-octyloxy group, and a benzyloxy group. Of those alkoxy groups, a methoxy group or an ethoxy group is preferred.

Examples of the aryloxy group represented by any one of $R_{30}$ to $R_{57}$ include, but, of course, not limited to, a phenoxy group, a 4-tert-butylphenoxy group, and a thienyloxy group.

An example of the aralkyl group represented by any one of $R_{30}$ to $R_{57}$ is, but, of course, not limited to, a benzyl group.

Examples of the substituted amino group represented by any one of $R_{30}$ to $R_{57}$ include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphtylamino group, an N,N-difluorenylamino group, an N-phenyl-N-tolylamino group, an N,N-ditolylamino group, an N-methyl-N-phenylamino group, an N,N-dianisoylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Specific examples of the aromatic hydrocarbon group represented by any one of $R_{30}$ to $R_{57}$ include, but, of course, not limited to, a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group. Of those aromatic hydrocarbon groups, a phenyl group, a naphthyl group, a fluorenyl group, or a biphenyl group is preferred, and a phenyl group is more preferred.

Specific examples of the heteroaromatic group represented by any one of $R_{30}$ to $R_{57}$ include, but, of course, not limited to, a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group.

Examples of the substituent that the alkyl group, the aryl group, and the heterocyclic group each may further have include: alkyl groups such as a methyl group, an ethyl group, and a propyl group; aralkyl groups such as a benzyl group; aryl groups such as a phenyl group, a biphenyl group, and a tetrakis(9,9-dimethylfluorenyl) group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, and a propoxyl group; aryloxyl groups such as a phenoxyl group; halogen atoms such as fluorine, chlorine, bromine, and iodine atoms; and a cyano group.

The substituents represented in any one of the formulae [6] to [11], i.e., $R_{30}$ to $R_{57}$ each preferably represent a hydrogen atom, an alkyl group having 1 to 4 carbon atoms, or a phenyl group that may be substituted with an alkyl group having 1 to 4 carbon atoms.

In the formulae [8] to [11], *1 represents a bonding position with an oxygen atom and *2 represents a bonding position with a carbon atom sandwiched between heteroatoms in a heterocyclic five-membered ring skeleton represented below.

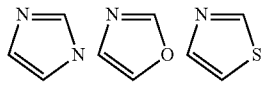

In the formulae [8] to [11], a ring B is any one of the cyclic structures represented by the following general formulae [12] to [14].

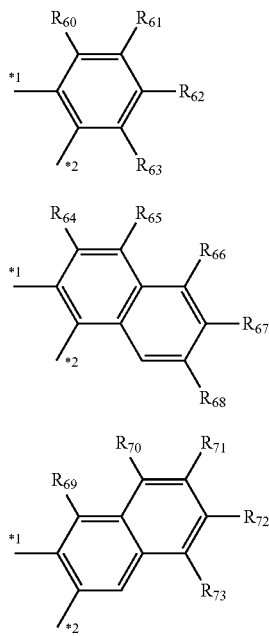

In the formulae [12] to [14], $R_{60}$ to $R_{73}$ each represent a hydrogen atom, a halogen atom, a substituted or unsubstituted alkyl group, an alkoxy group, an aryloxy group, an aralkyl group, a substituted amino group, a substituted or unsubstituted aromatic hydrocarbon group, or a substituted or unsubstituted heteroaromatic group.

Specific examples of the halogen atom, alkyl group, alkoxy group, aryloxy group, aralkyl groups substituted amino group, aromatic hydrocarbon group, and heteroaromatic group represented by $R_{60}$ to $R_{73}$, and the substituent that the alkyl group, the aromatic hydrocarbon group, and the heteroaromatic group each may further have are the same as the specific examples in $R_{30}$ to $R_{57}$ in the general formulae [6] to [11].

The substituents represented in any one of the formulae [12] to [14], i.e., $R_{60}$ to $R_{73}$ each preferably represent a hydrogen atom, an alkyl group having 1 to 4 carbon atoms, or a phenyl group that may be substituted with an alkyl group having 1 to 4 carbon atoms.

(4) Operations and Effects Exhibited by Host and Guest

The organic compound layer (especially the emission layer) constituting the organic light-emitting element of the present invention includes at least the iridium complex represented by the general formula [1] and the metal complex represented by the general formula [5]. The iridium complex represented by the formula [1] is an organometallic complex in which at least one arylbenzo[f]isoquinoline ligand coordinates to an iridium metal, i.e., a biq-based Ir complex. Here, as described in PTL 1, the biq-based Ir complex is a phosphorescent light-emitting material having a high emission quantum efficiency and capable of emitting red light. Here, the term "red light emission" refers to such light emission that an emission peak wavelength is 580 nm or more and 650 nm or less, i.e., the lowest triplet excited level ($T_1$) falls within the range of 1.9 eV or more to 2.1 eV or less. Therefore, the incorporation of the biq-based Ir complex as a guest into the emission layer makes the luminous efficiency of the organic light-emitting element extremely high.

Meanwhile, performances required in the organic light-emitting element are, for example, a luminescent color, a driving voltage, and a element lifetime as well as the luminous efficiency. A high-performance organic light-emitting element can be produced by satisfying those requirements.

The optimization of the combination of the light-emitting material and the host is important for realizing the high-performance organic light-emitting element. Here, when a material that emits phosphorescence at room temperature is used as the light-emitting material, the following items are important:

[Item 1] a relationship between the excitation energies ($T_1$) in a triplet state of the light-emitting material and the host;
[Item 2] a relationship between the band gaps ($S_1$) of the light-emitting material and the host;
[Item 3] a relationship between the HOMO-LUMO's of the light-emitting material and the host; and
[Item 4] the luminous efficiency of the light-emitting material.

The fact that [Item 1] is important results from the fact that the light emission of the phosphorescent light-emitting material is light emission from the $T_1$. If values for the $T_1$ of the host and the $T_1$ of the light-emitting material are close to each other, an energy (emission energy) needed for the light-emitting material to emit phosphorescence is absorbed by the host. In that case, the luminous efficiency reduces. Accordingly, the values for the $T_1$ of the host and the $T_1$ of the light-emitting material are prevented from becoming close to each other. In addition, the materials are preferably selected so that the host may have a longer phosphorescence lifetime than that of the light-emitting material. This is because in that case, the energy can be passed to the light-emitting material. In this respect, the host to be used is a metal complex having a $T_1$ in terms of a wavelength shorter than that of the light-emitting material by 30 nm or more, and having a longer phosphorescence lifetime and a smaller atomic number than those of the light-emitting material. As a result, the high-performance organic light-emitting element can be produced.

It is because the $S_1$ of each material is largely involved in the driving voltage of the element that the fact that [Item 2] is important. Here, values for the $S_1$'s of the light-emitting material and the host are preferably set to be as close as possible to each other in order that the driving voltage of the element may be reduced. In this respect, in view of a relationship between the $S_1$ and $T_1$ of the host, a difference between the $S_1$ and the $T_1$ is preferably as small as possible.

It is because the HOMO-LUMO of each of the light-emitting material and the host is largely related to the driving voltage that the fact that [Item 3] is important. Here, the HOMO-LUMO level of the light-emitting material (phosphorescent light-emitting material) to be used in the organic light-emitting element of the present invention is shallow and hence the emission layer traps a hole. In this regard, when the trapping property of the layer is excessively high, the voltage increases and hence the power consumption of the element increases. Accordingly, a material having as shallow an HOMO as possible needs to be used as the host.

It is because the luminous efficiency directly affects the performance of the organic light-emitting element that the fact that [Item 4] is important. Therefore, the use of a high-efficiency light-emitting material is essential for the production of the high-performance organic light-emitting element. In that respect, the light-emitting material used in the present invention is a light-emitting material having very high luminous efficiency out of the light-emitting materials that emit red light.

Upon combination of the light-emitting material and the host for producing the high-performance organic light-emitting element in consideration of the four items, the luminous efficiency of the light-emitting material itself needs to be improved (a light-emitting material having high luminous efficiency needs to be selected). In addition, a material having a small $S_1$ and a small $T_1$ needs to be selected as the host. A material optimum as a host satisfying those conditions is a metal complex. This is because the metal complex has a small $S_1$ and its HOMO can be shallowed as compared with any other compound. In addition, the light-emitting material emits light having a wavelength of 610 nm or more, and hence a metal having a $T_1$ of 580 nm or less, and having a longer phosphorescence lifetime and a smaller atomic number than those of the light-emitting material is preferably used in the metal complex to be used as the host.

In this respect, the organic light-emitting element including the iridium complex represented by the general formula [1] and the metal complex represented by the general formula [5] has higher performance than that of a related art phosphorescent light-emitting element particularly from the viewpoint of luminous efficiency.

(5) Specific Examples of Iridium Complex

Specific structural formulae of the iridium complex defined by the general formula [1] are exemplified below.

[Group 1 compound]

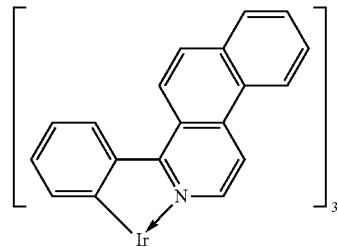

Ir-101

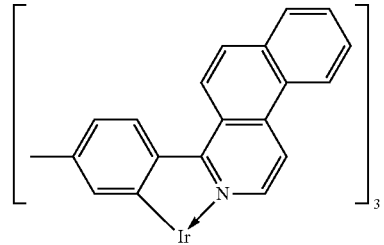

Ir-102

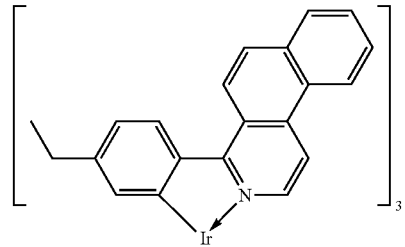

Ir-103

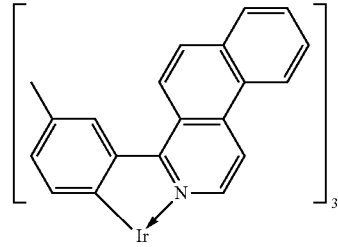

Ir-104

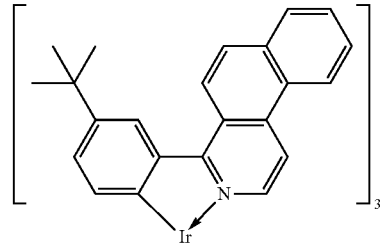

Ir-105

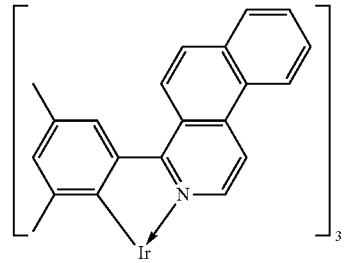

Ir-106

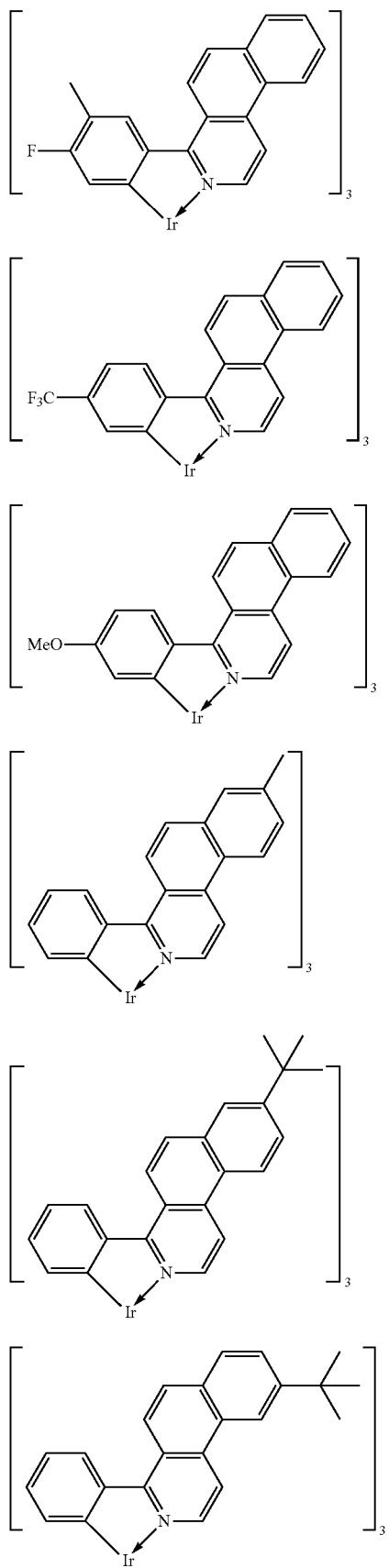

Ir-119
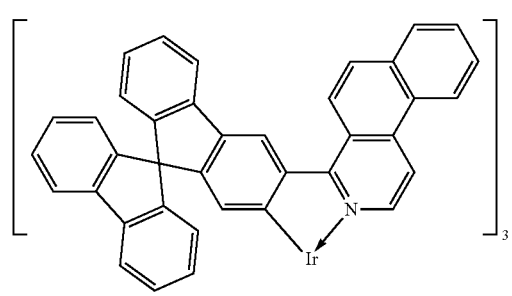
Ir-120
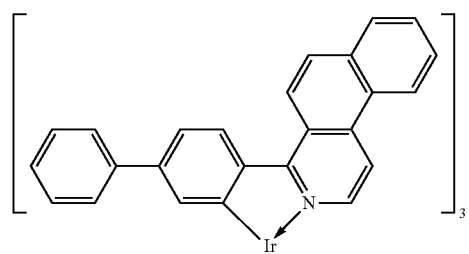
Ir-121
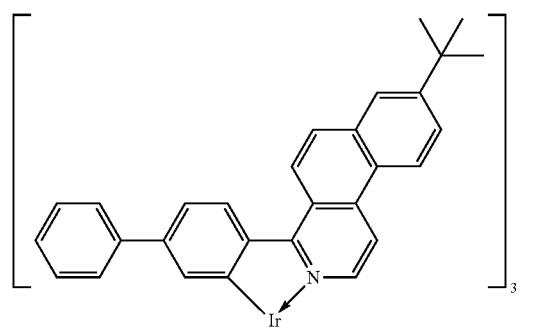
Ir-122
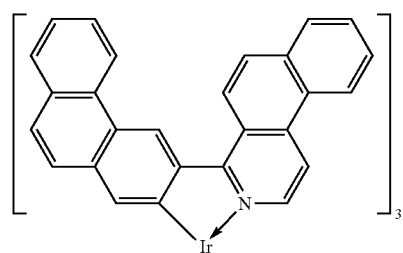
Ir-123
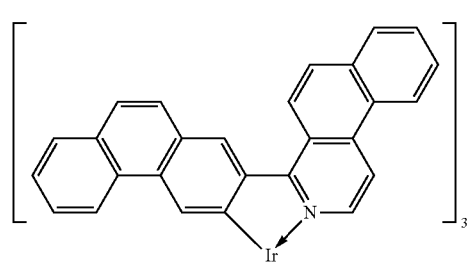
[Group 2 compound]
Ir-201
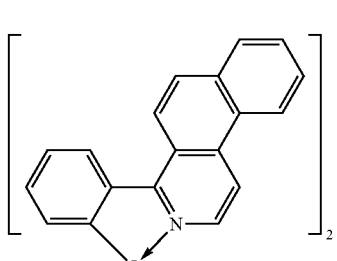
Ir-202
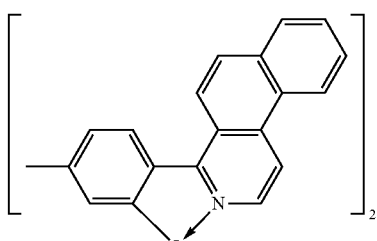
Ir-203
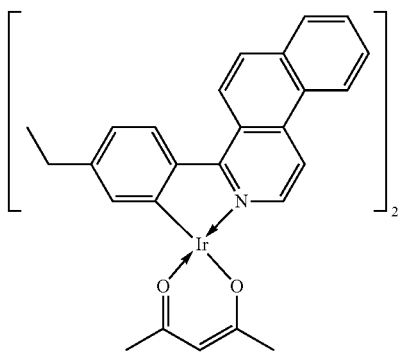
Ir-204
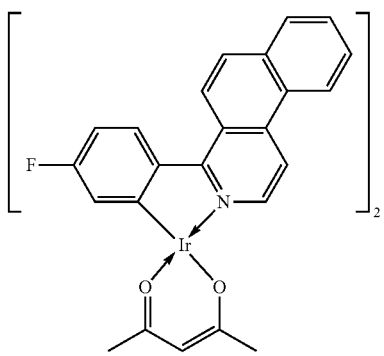

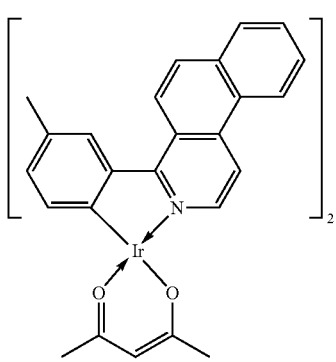 Ir-205
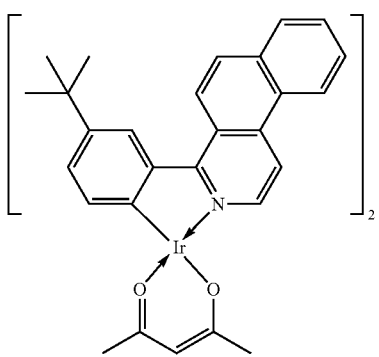 Ir-206
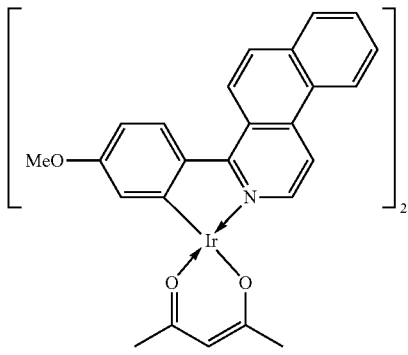 Ir-207
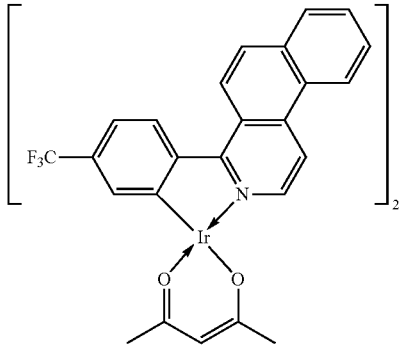 Ir-208
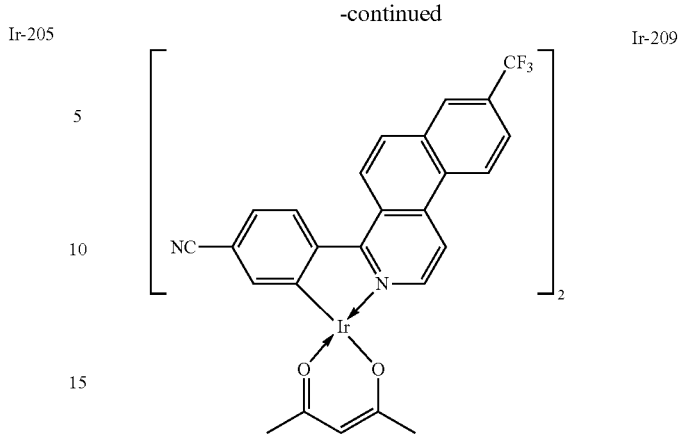 Ir-209
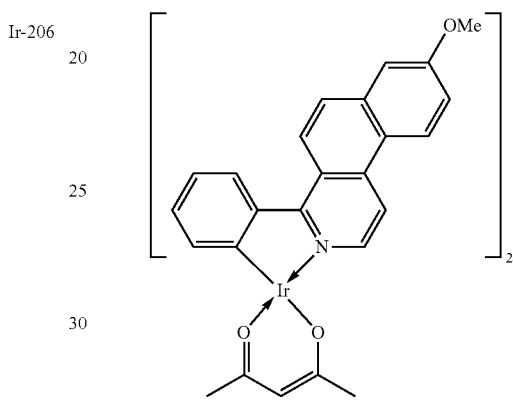 Ir-210
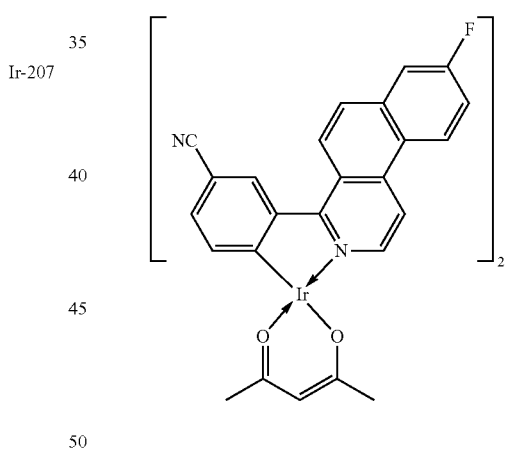 Ir-211
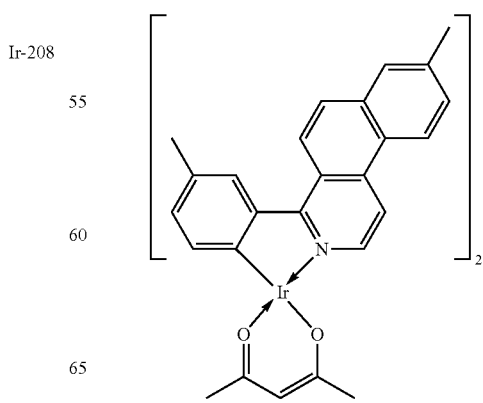 Ir-212

Ir-213
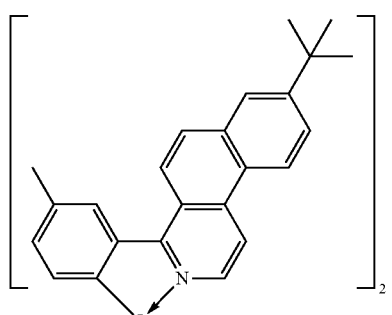
Ir-214
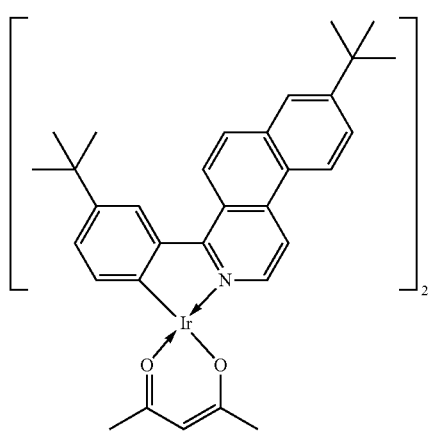
Ir-215
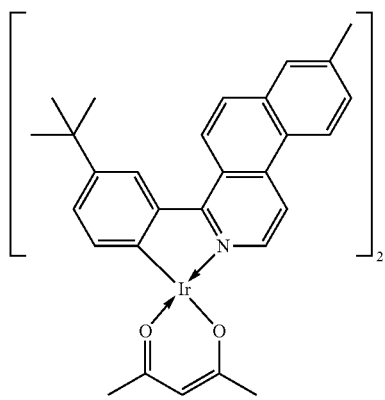
Ir-216
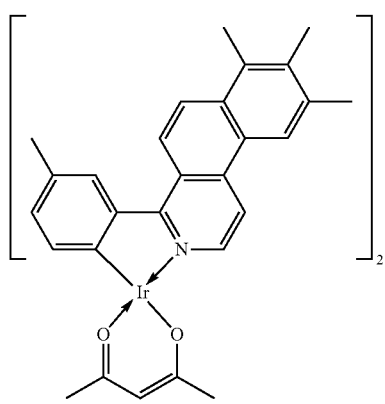
Ir-217
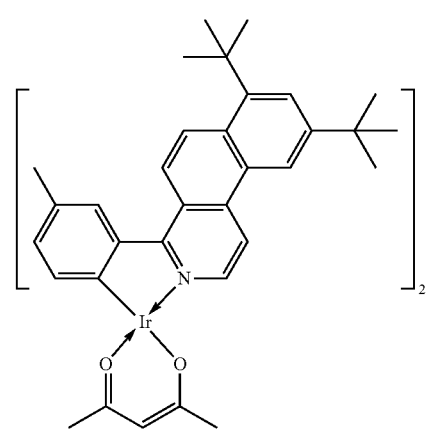
Ir-218
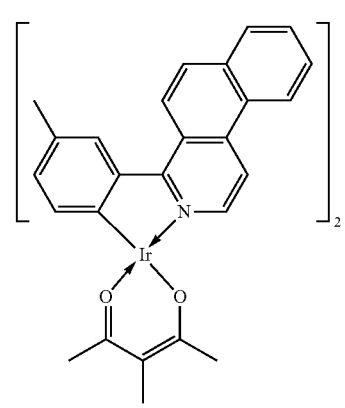
Ir-219
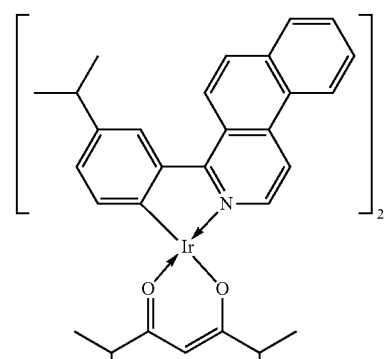
Ir-220
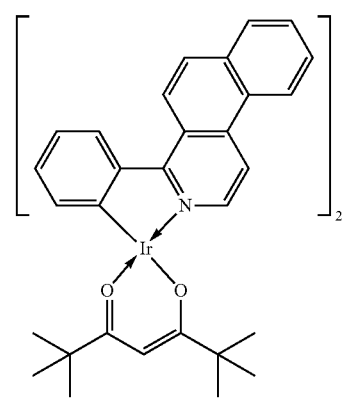

Ir-221
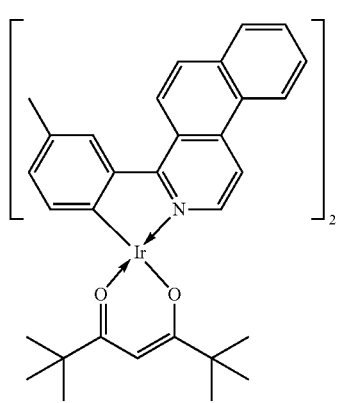
Ir-222
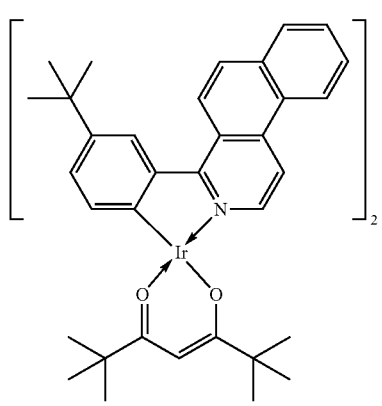
Ir-223
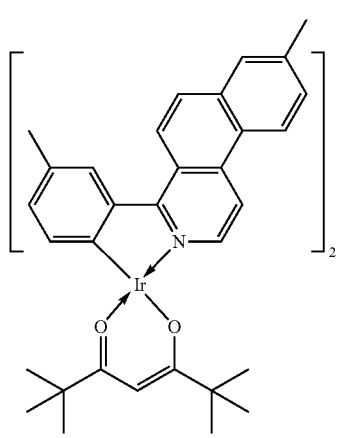
Ir-224
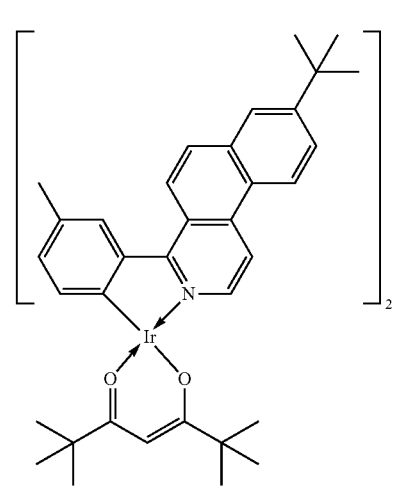
Ir-225
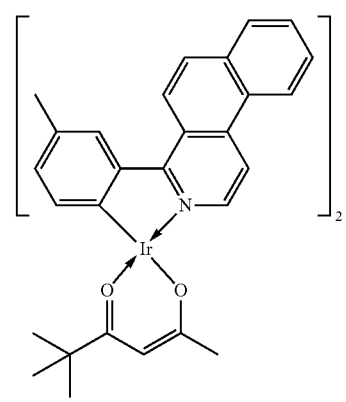
Ir-226
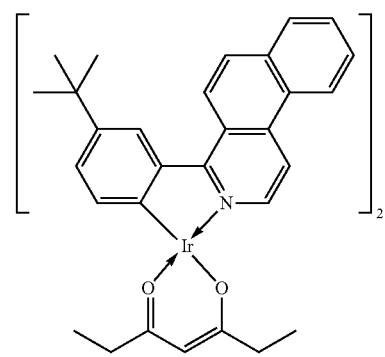
[Group 3 compound]
Ir-301
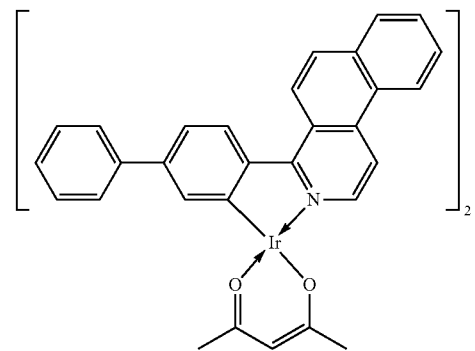

-continued
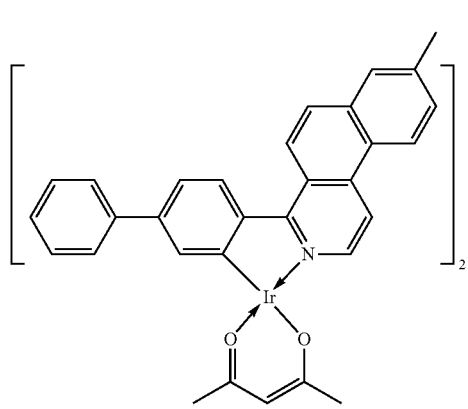
Ir-302
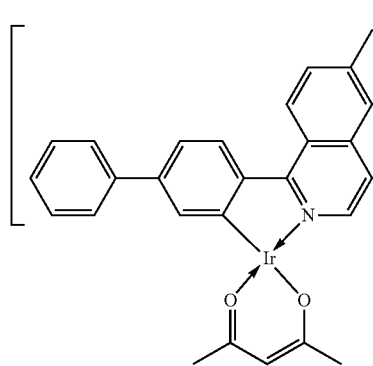
Ir-303
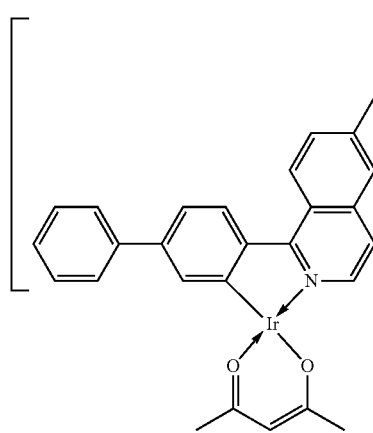
Ir-304
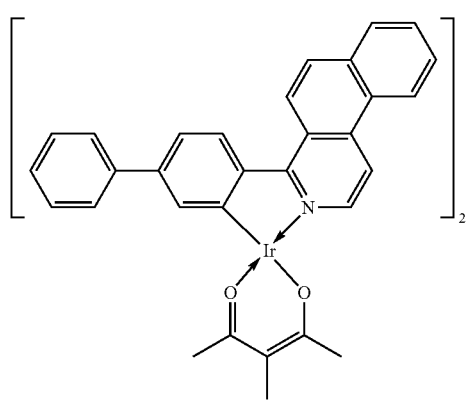
Ir-305
-continued
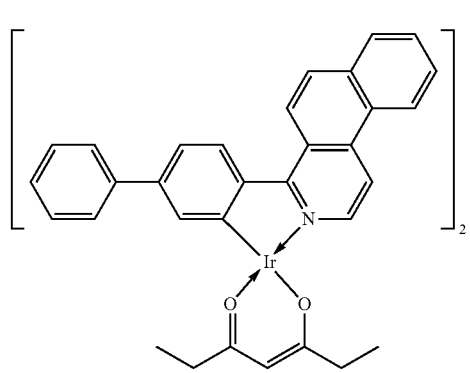
Ir-306
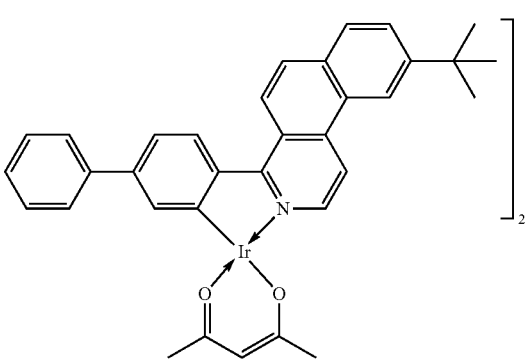
Ir-307
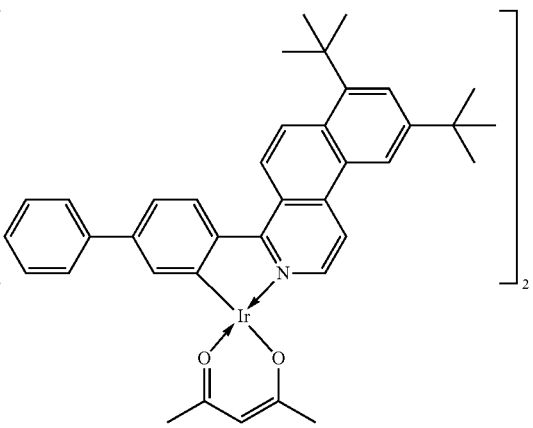
Ir-308
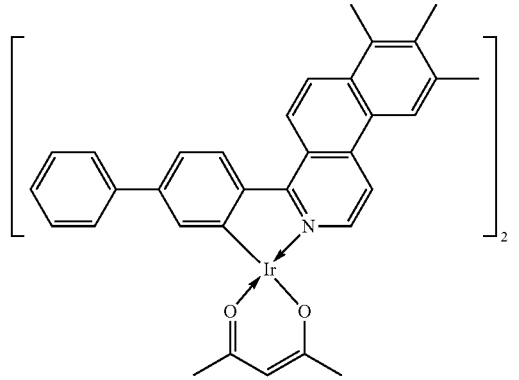
Ir-309

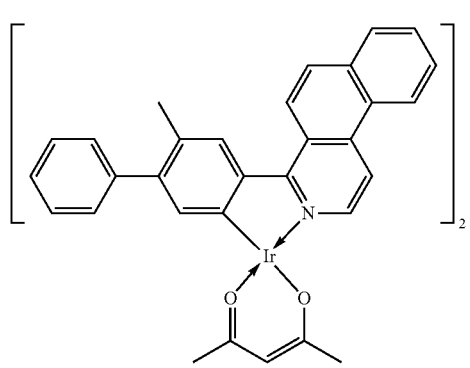
Ir-310
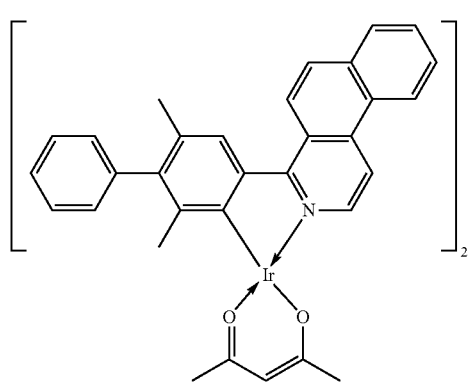
Ir-311
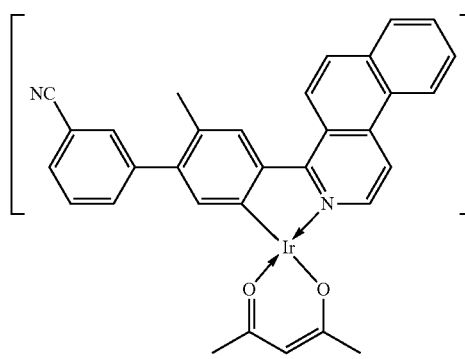
Ir-312
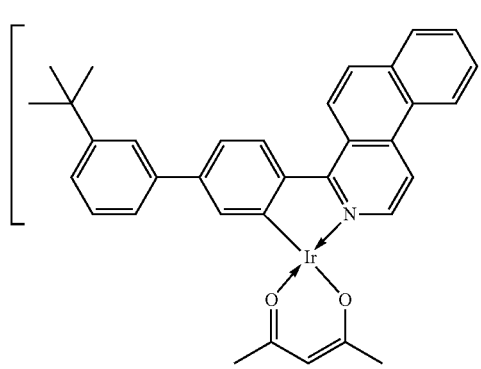
Ir-313
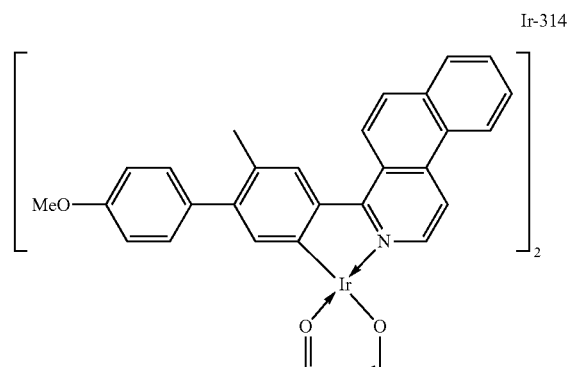
Ir-314
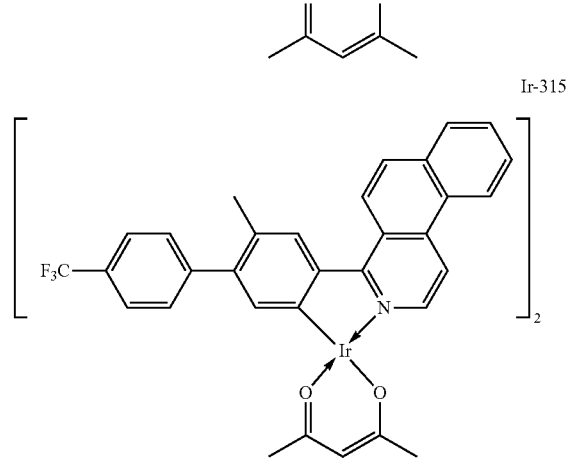
Ir-315
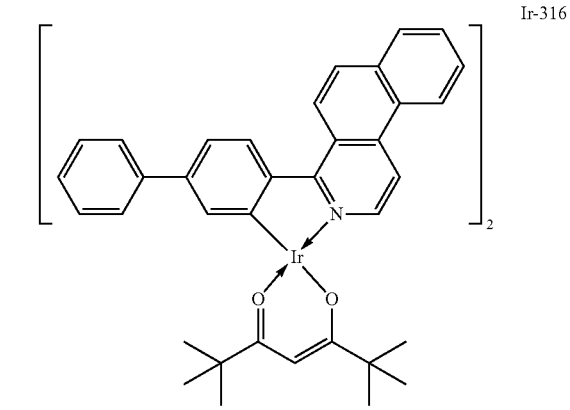
Ir-316
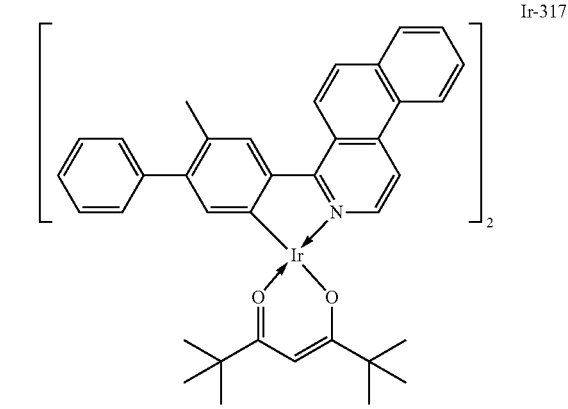
Ir-317

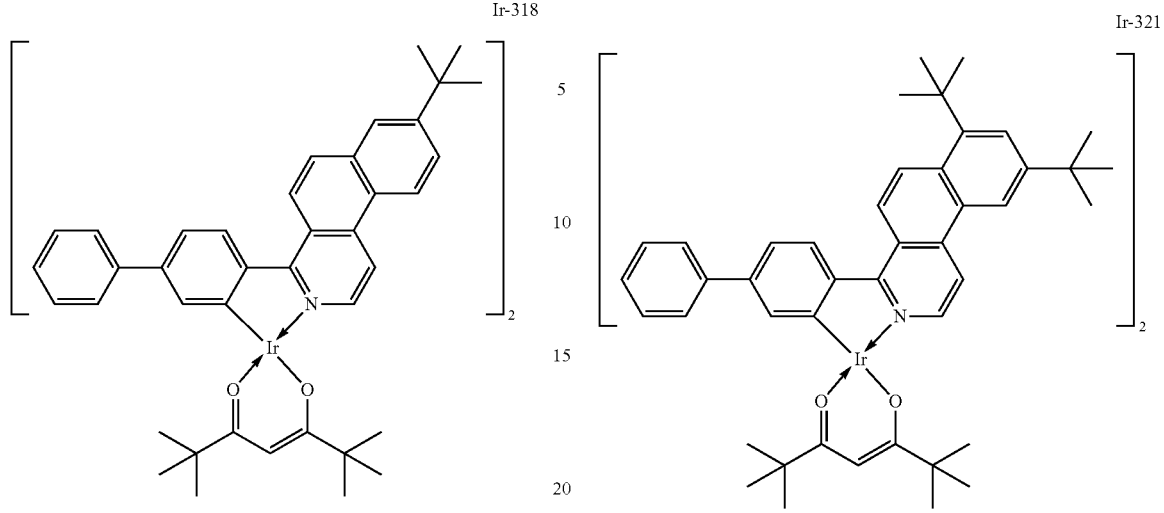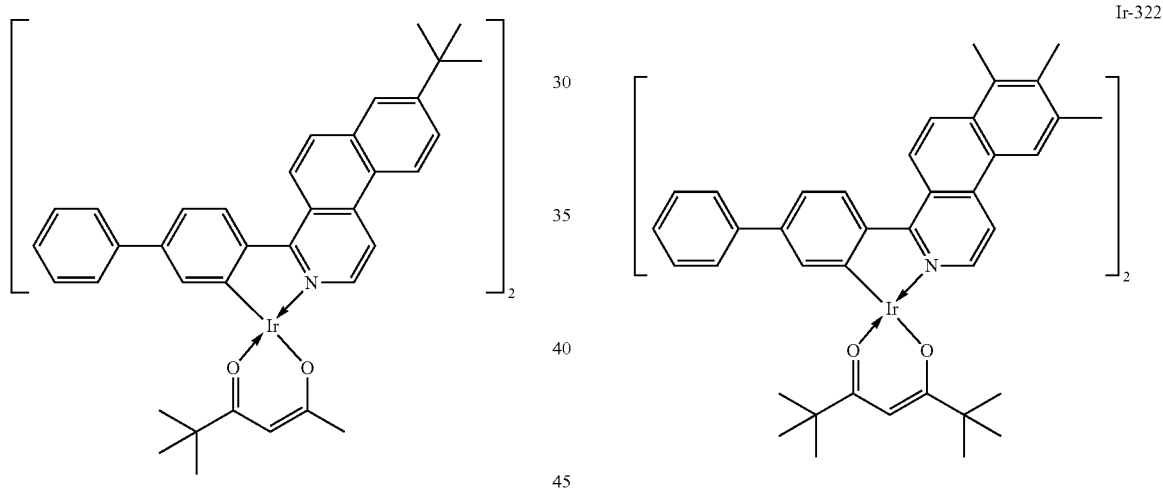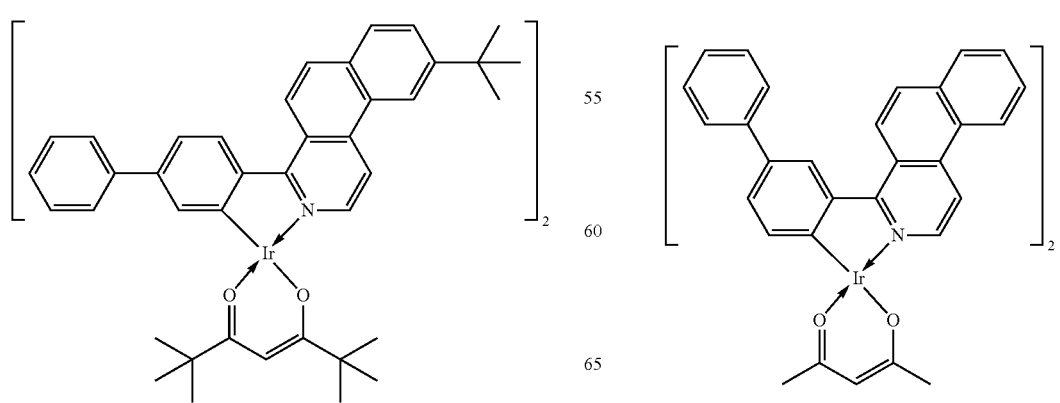

Ir-402
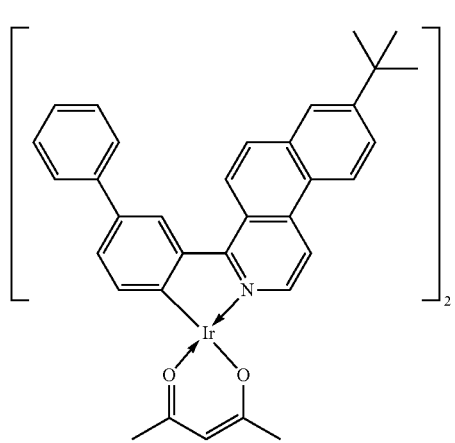
Ir-403
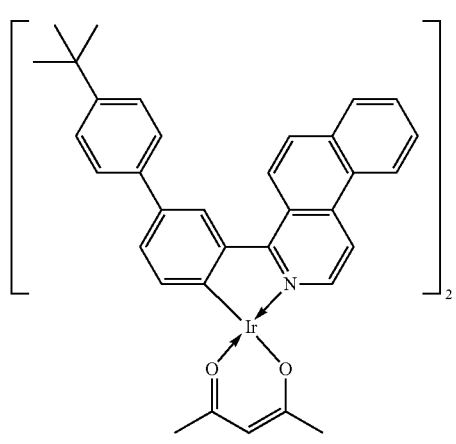
Ir-404
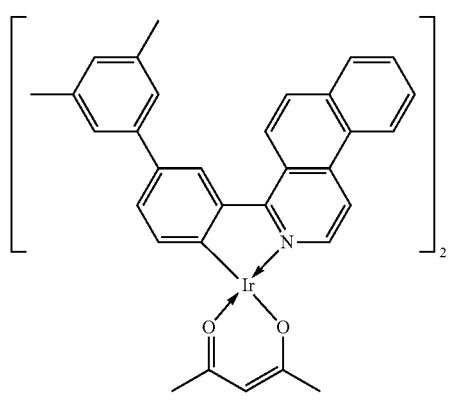
Ir-405
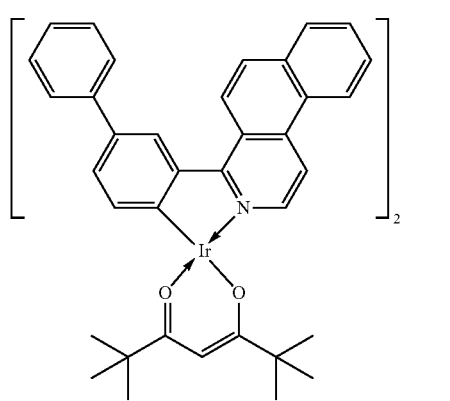
Ir-406
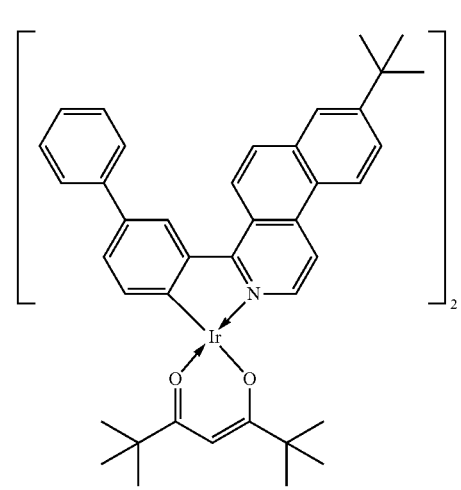
Ir-407
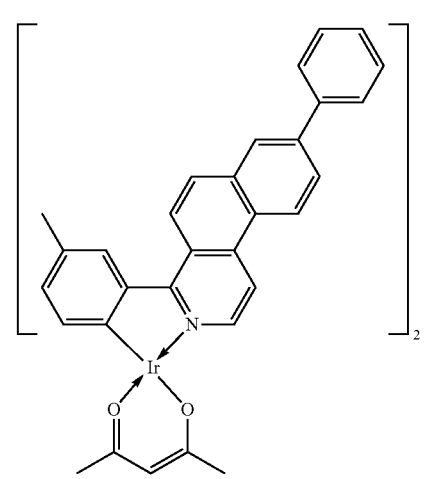
Ir-408
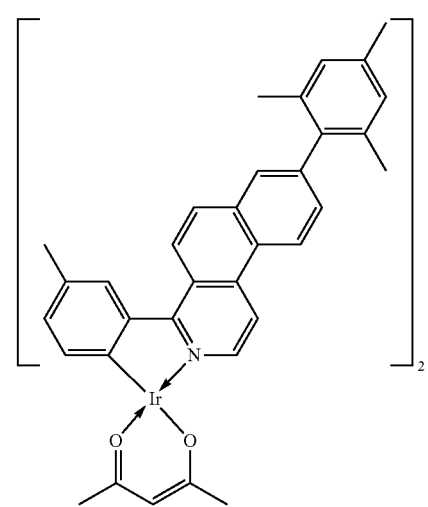

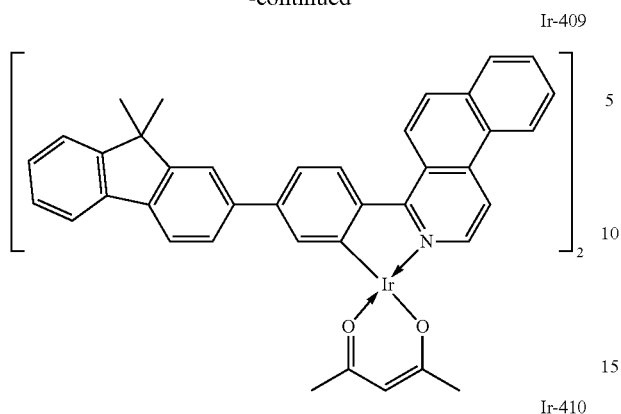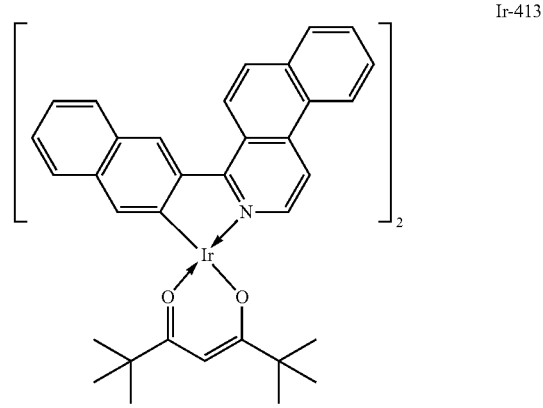

-continued
Ir-417
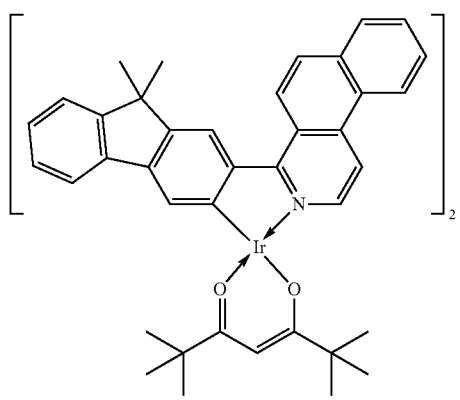
Ir-418
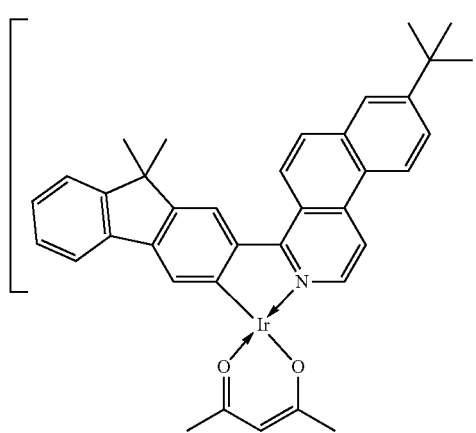
Ir-419
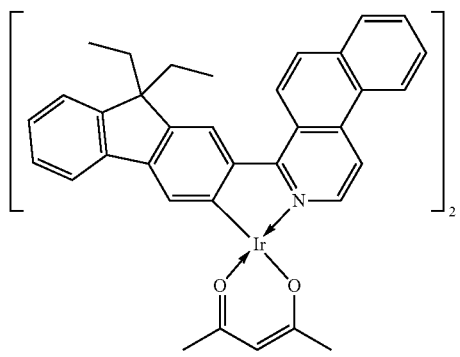
Ir-420
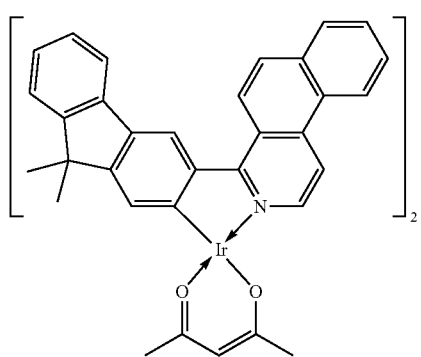
-continued
Ir-421
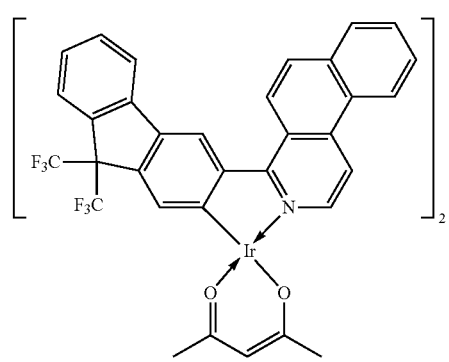
Ir-422
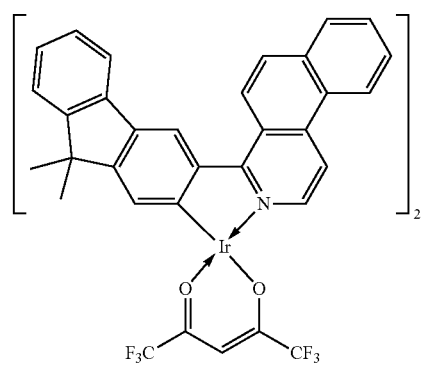
Ir-423
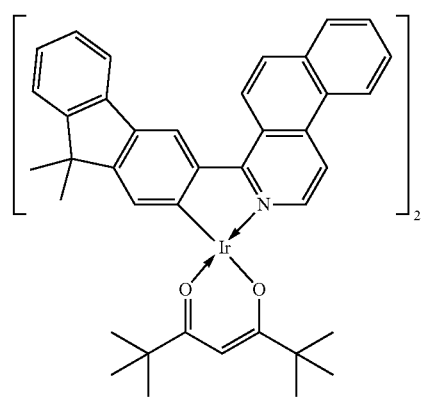
Ir-424
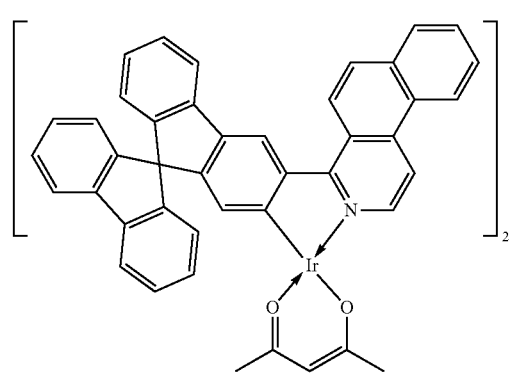

Ir-425
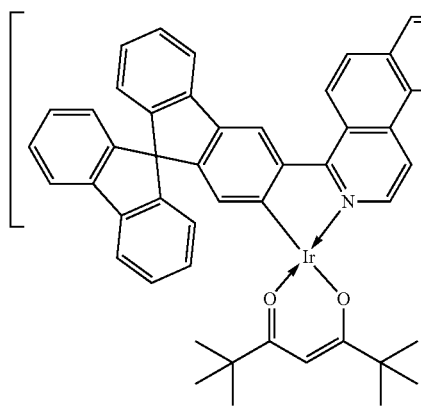
Ir-426
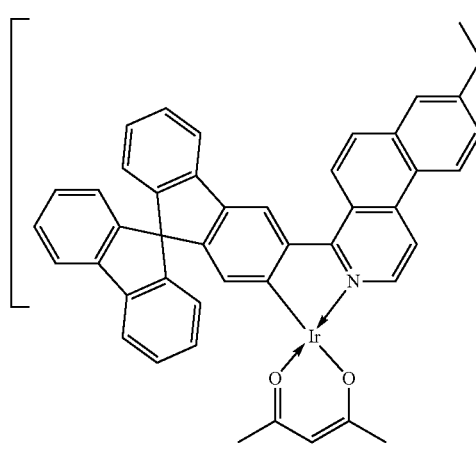
Ir-427
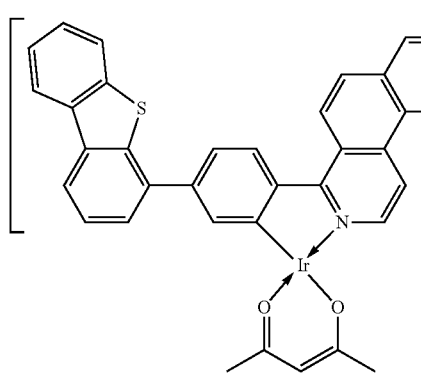
Ir-428
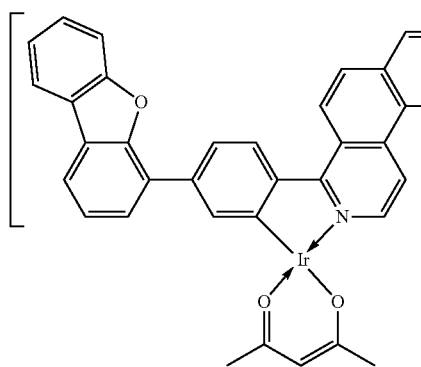
Ir-429
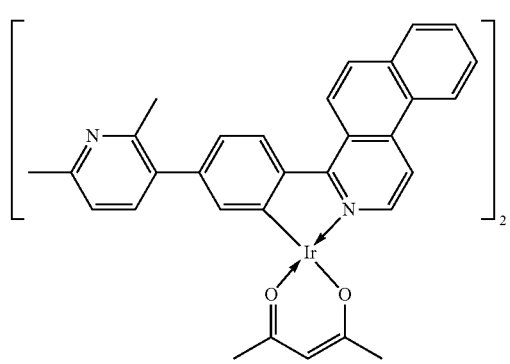
[Group 5a compound]
Ir-501
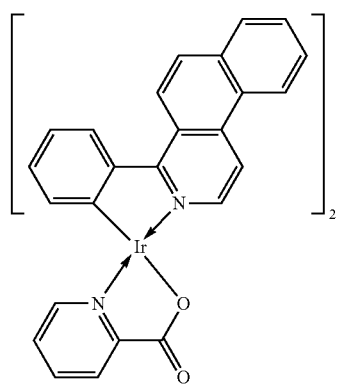
Ir-502
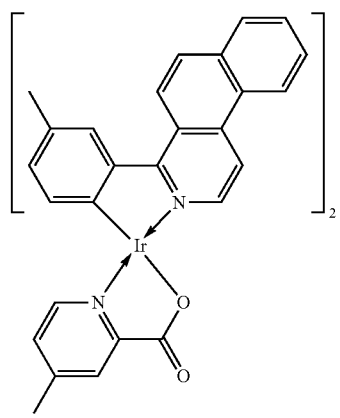
Ir-503
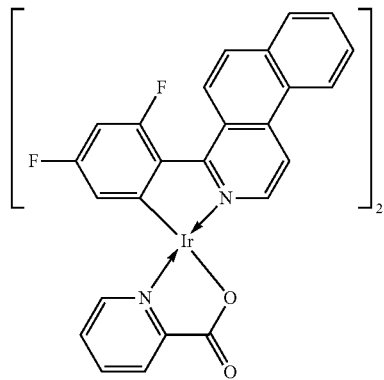

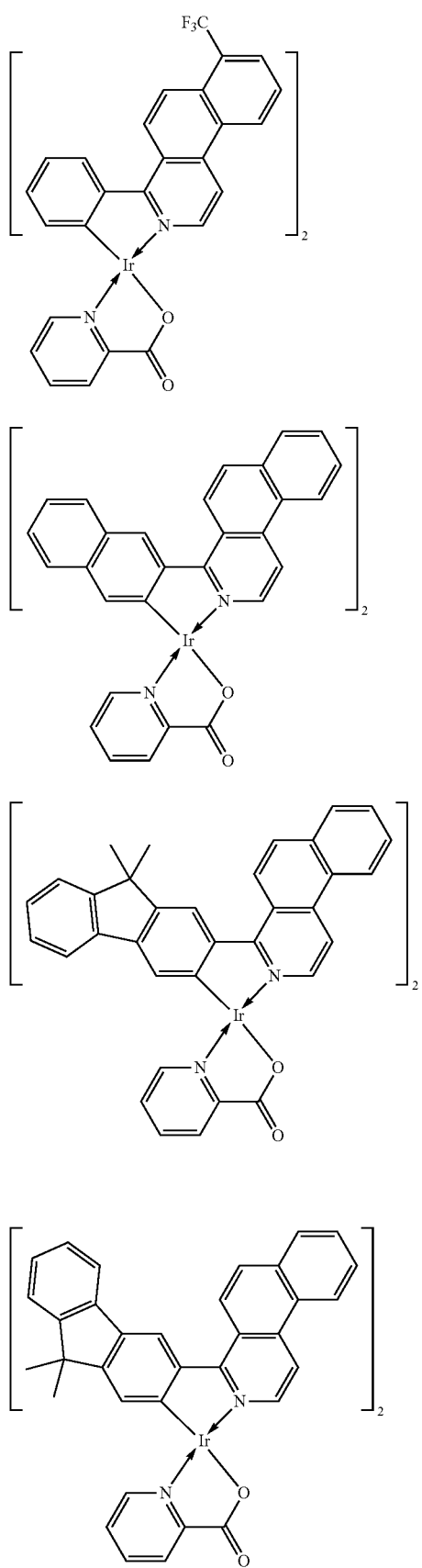
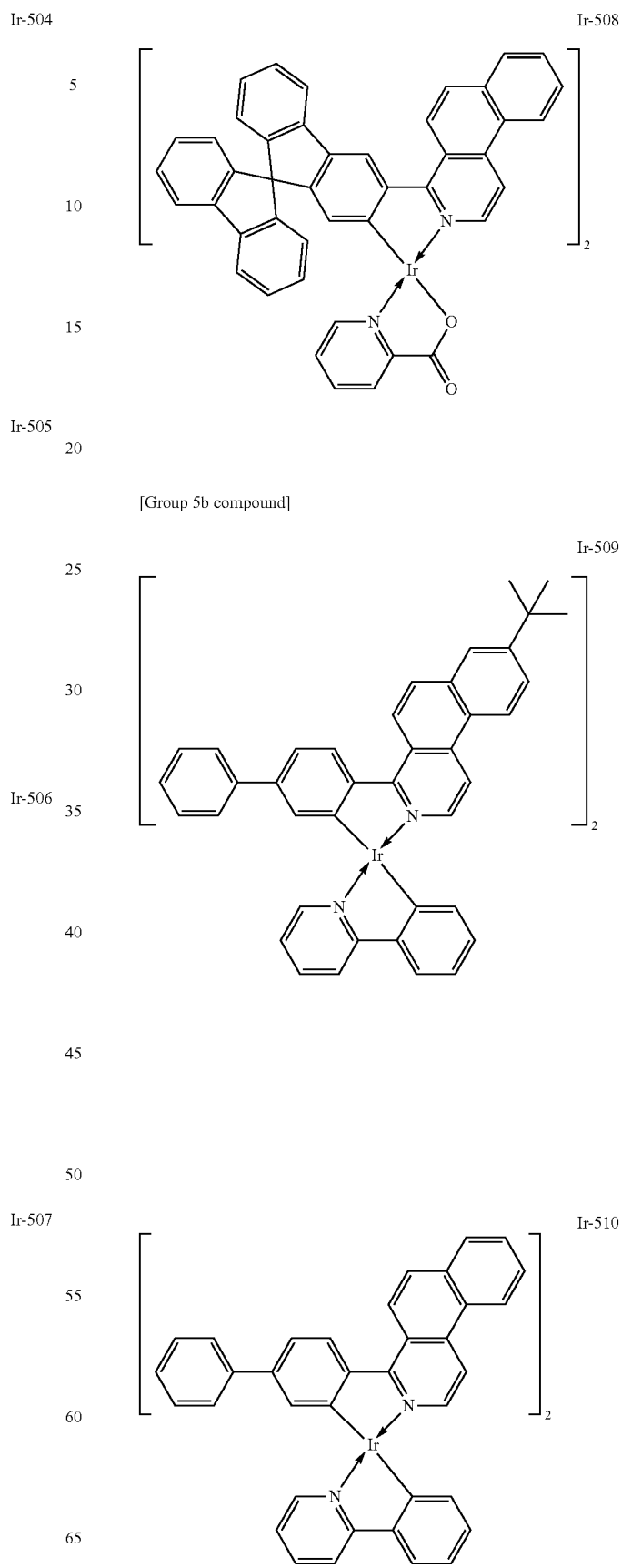
[Group 5b compound]

Ir-511

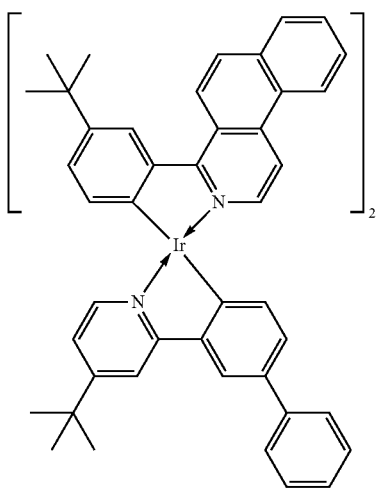

Ir-512

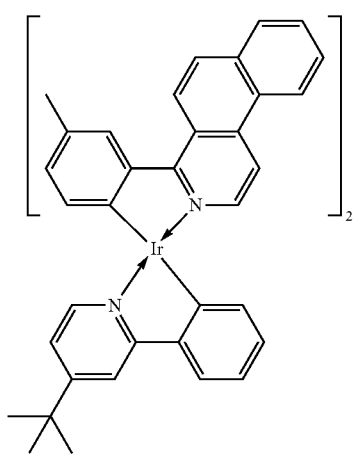

Ir-513

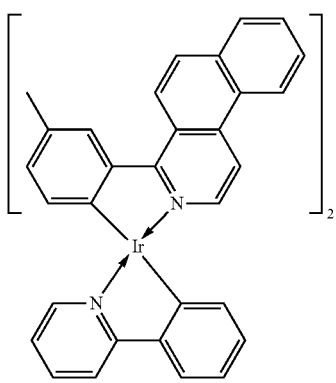

Ir-514

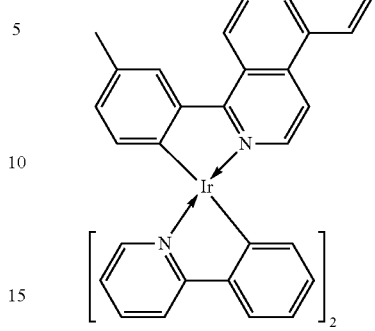

Ir-515

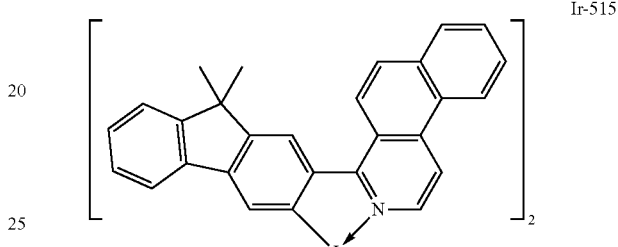

Ir-516

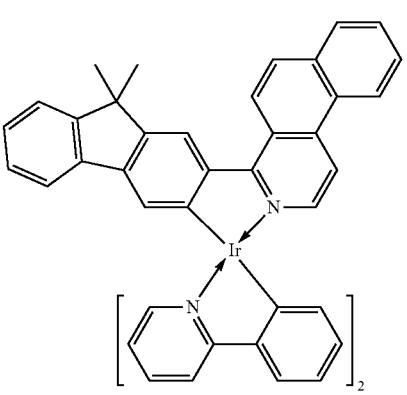

Of the exemplified compounds, the iridium complexes represented by Ir-101 to Ir-123 are each an iridium complex in which all ligands are each a ligand including a benzo[f] isoquinoline skeleton out of the iridium complexes each represented by the general formula [1]. The stability of each of those iridium complexes in the group 1 itself is extremely high by virtue of the structure of the ligand (arylbenzo[f] isoquinoline ligand) of the complex. Therefore, the incorporation of any such complex as a guest into the emission layer provides a long-lifetime organic light-emitting element because the incorporation improves its driving durability.

Of the exemplified compounds, the iridium complexes represented by Ir-201 to Ir-226 are each an iridium complex in which G does not represent a substituted or unsubstituted phenyl group out of the iridium complexes each represented by the general formula [21]. Those iridium complexes in the group 2 are each a complex having an extremely high emission quantum efficiency and hence the incorporation of any such complex as a guest into the emission layer provides an organic light-emitting element having high luminous efficiency. Further, three ligands of each iridium complex in the group 2 include one acac-based ligand (diketone-based bidentate ligand) having a small molecular weight. Accordingly, the complex has the following advantage: the complex can be easily subjected to sublimation purification because the molecular weight of the complex itself is relatively small.

Of the exemplified compounds, the iridium complexes represented by Ir-301 to Ir-322 are each an iridium complex in which G represents a substituted or unsubstituted phenyl group out of the iridium complexes each represented by the general formula [21]. Those iridium complexes in the group 3 are each a complex having an extremely high emission quantum efficiency as in the iridium complexes in the group 2. Accordingly, the incorporation of any such complex as a guest into the emission layer improves the luminous efficiency of the organic light-emitting element.

Of the exemplified compounds, the iridium complexes represented by Ir-401 to Ir-429 are each an iridium complex represented by the general formula [1] in which m represents 2 and n represents 1, but the iridium complex does not correspond to any iridium complex represented by the general formula [21]. Those iridium complexes in the group 4 are each also a complex having an extremely high emission quantum efficiency as in the iridium complexes in the groups 2 and 3. Accordingly, the incorporation of any such complex as a guest into the emission layer improves the luminous efficiency of the organic light-emitting element.

Of the exemplified compounds, the iridium complexes represented by Ir-501 to Ir-508 are each an iridium complex represented by the general formula [1] in which the partial structure $IrX_n$ is represented by the formula [3]. Those iridium complexes in the group 5a each contain, in a molecule thereof, one picolinic acid derivative as a ligand. Here, the introduction of the picolinic acid derivative as a ligand shifts the emission peak wavelength of the complex itself to shorter wavelengths as compared with that in the case where the acac-based ligand is introduced.

Of the exemplified compounds, the iridium complexes represented by Ir-509 to Ir-516 are each an iridium complex represented by the general formula [1] in which the partial structure $IrX_n$ is represented by the formula [2]. Those iridium complexes in the group 5b each contain, in a molecule thereof, one or two phenylpyridine (ppy) derivatives. Here, each iridium complex in the group 5b provides red light emission derived from the arylbenzo[f]isoquinoline ligand because the ligand ppy is a non-light-emitting ligand. In addition, the ligand ppy has a smaller molecular weight than that of the arylbenzo[f]isoquinoline ligand. Accordingly, the complex has a smaller molecular weight than that of any iridium complex in the group 1 and hence can be easily subjected to sublimation purification. Therefore, the incorporation of any iridium complex in the group 5b as a guest into the emission layer as in any iridium complex in the group 1 can provide a long-lifetime organic light-emitting element.

By the way, the following structural isomers sterically exist for the iridium complex represented by the general formula [1]: an fac form and an mer form. Although the steric structure of the iridium complex represented by the general formula [1] is not particularly limited in the present invention, the fac form generally credited with having a high quantum efficiency is preferred. However, in the case of an iridium complex in which two kinds of ligands having different structures coordinate to an iridium atom, the mer form such as Ir(ppy)$_2$acac may also have a high quantum efficiency. Accordingly, the fac form is not necessarily preferred. In addition, it is difficult to synthesize one of the structural isomers selectively at the time of the synthesis of the complex, and both isomers may be used as a mixture in terms of a cost.

(6) Specific Examples of Metal Complex

Specific structural formulae of the metal complex compound to be used as the host are exemplified below.

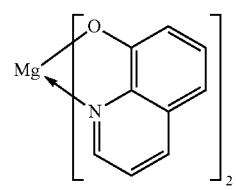

H101

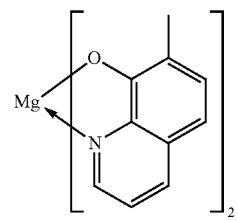

H102

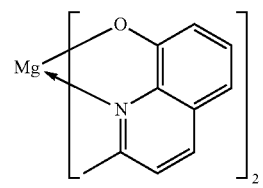

H103

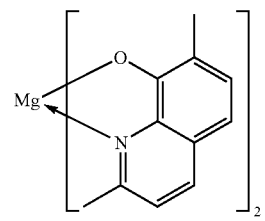

H104

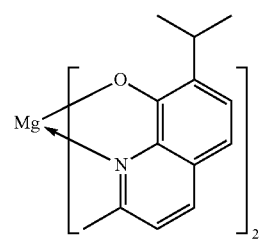

H105

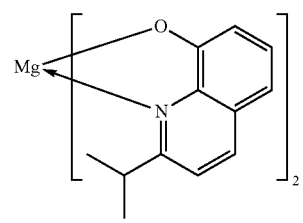

H106

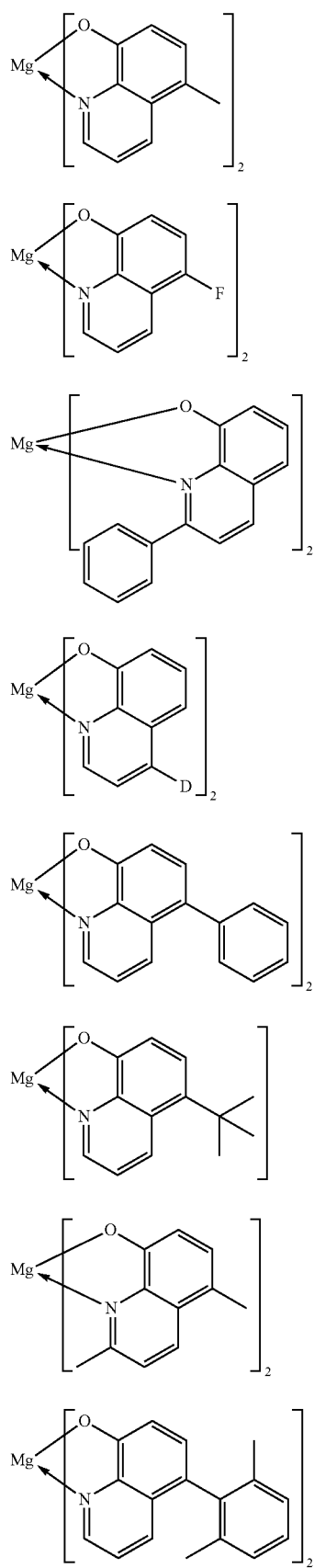
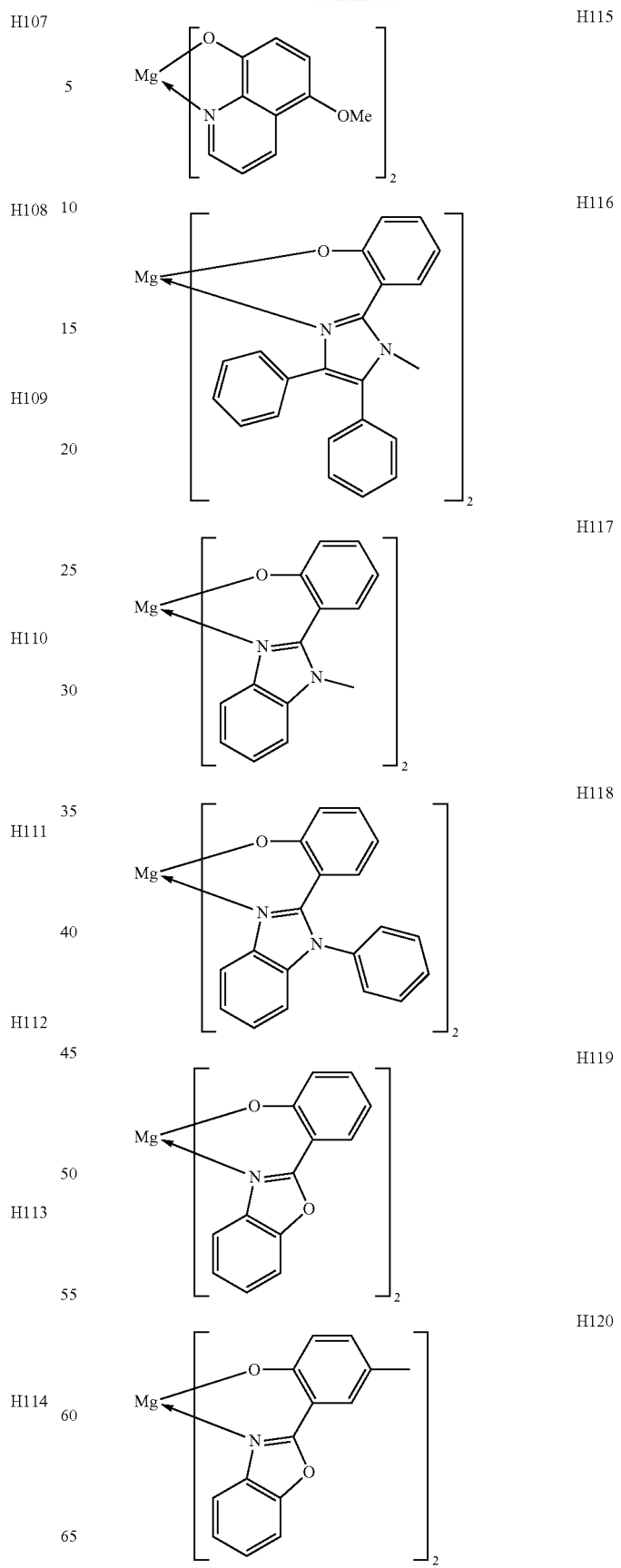

H121 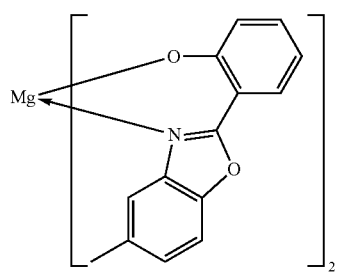
H122 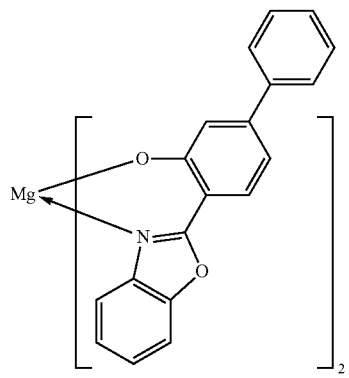
H123 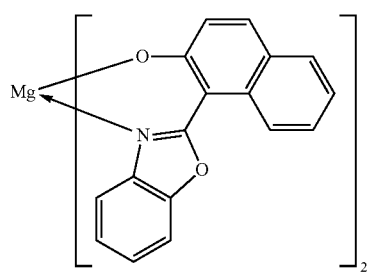
H124 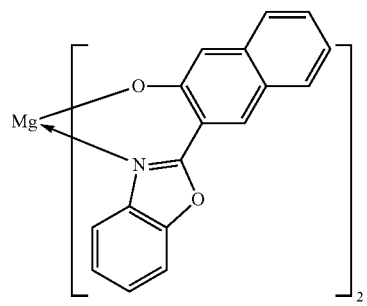
H125 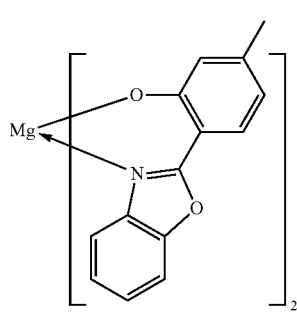
H126 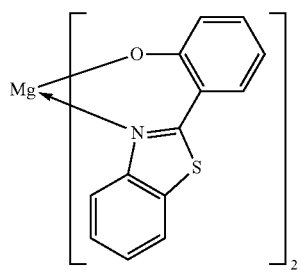
H127 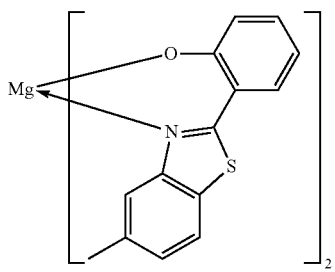
H128 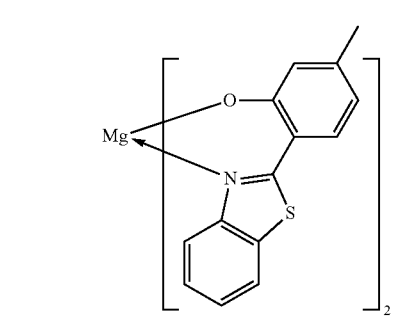
H129 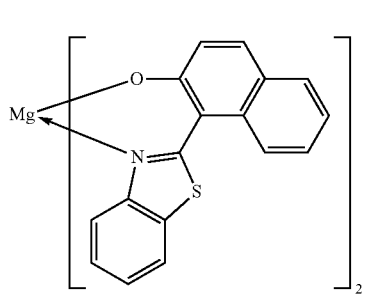
H130 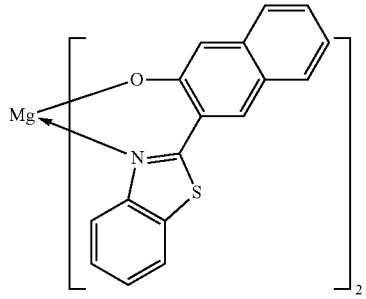

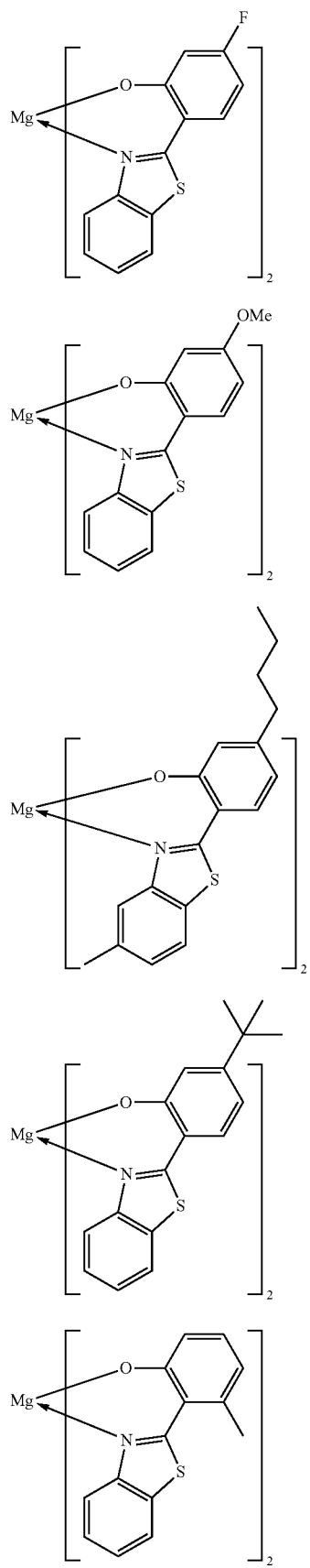
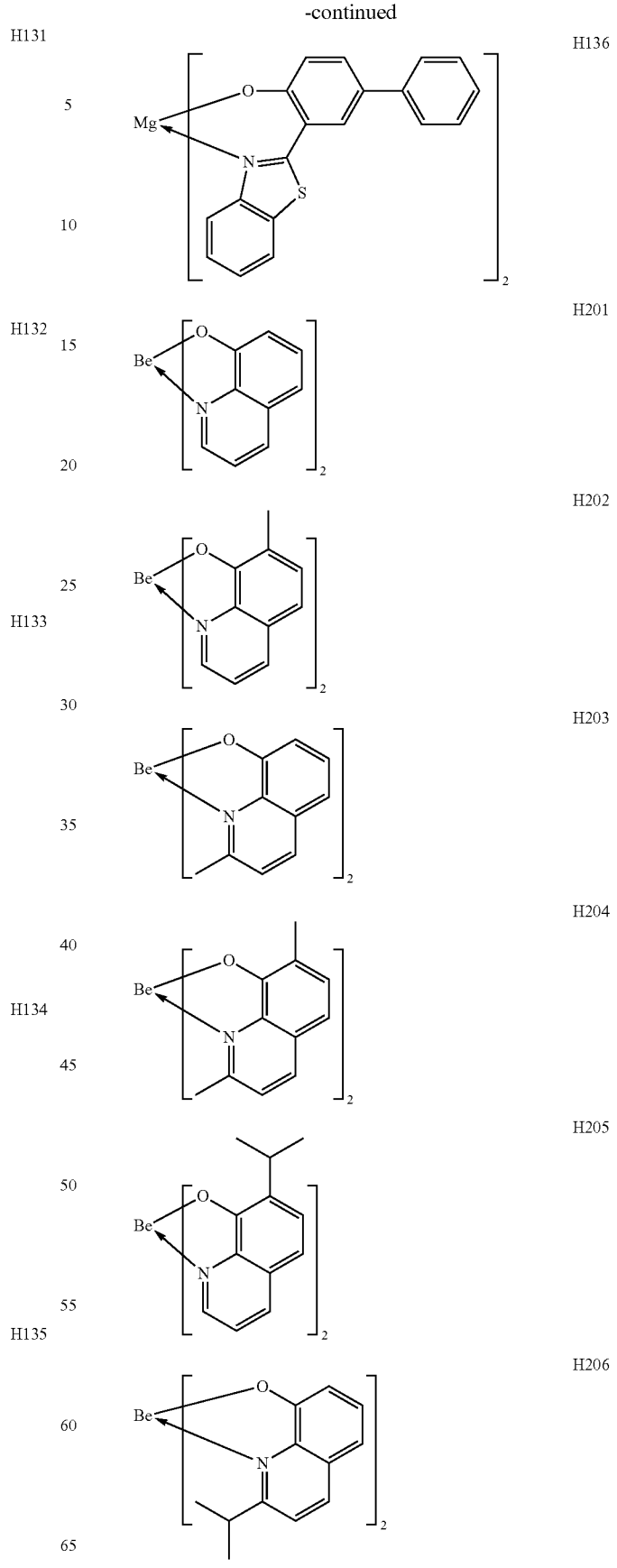

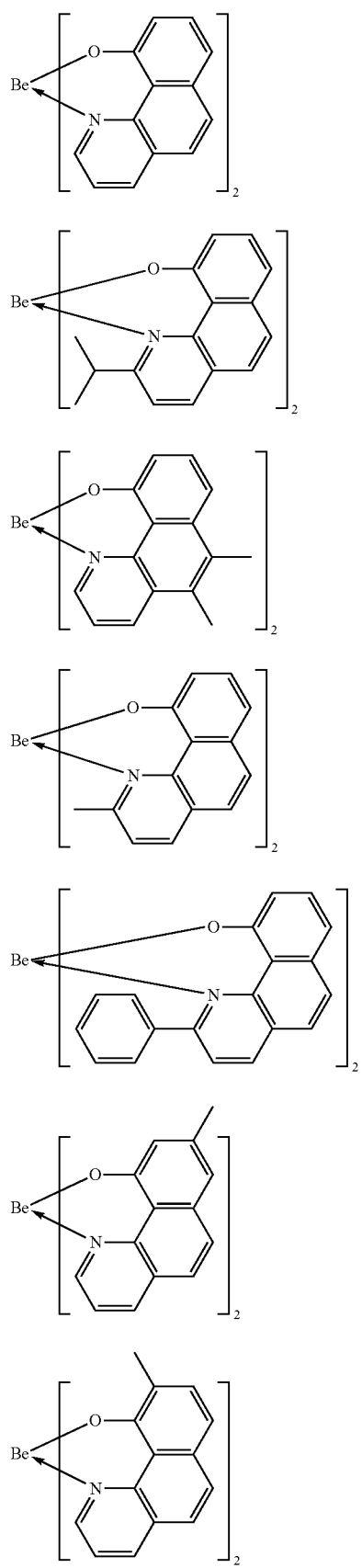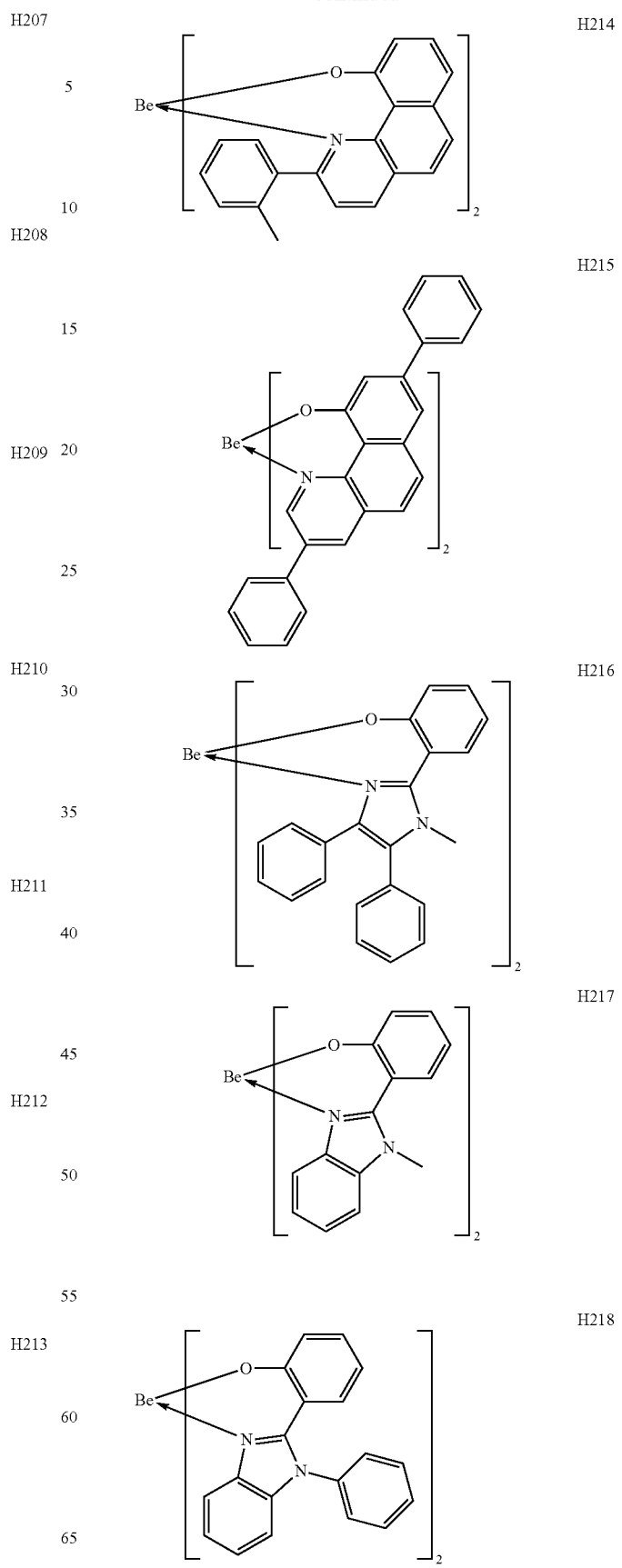

-continued
H219
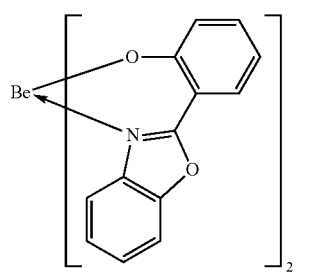
H220
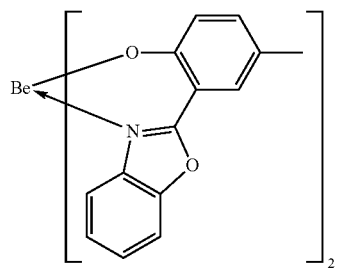
H221
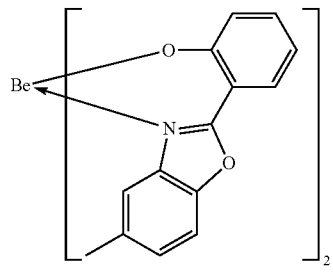
H222
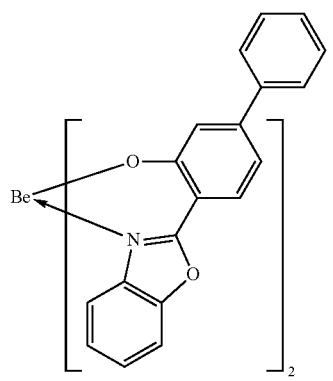
H223
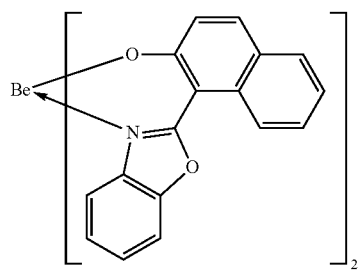
-continued
H224
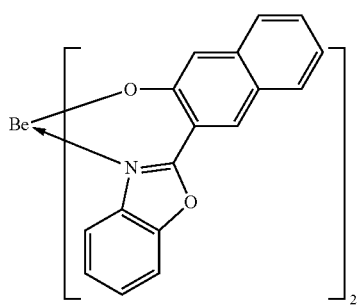
H225
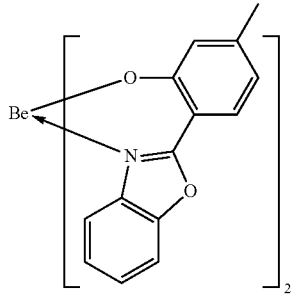
H226
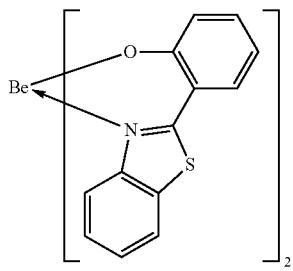
H227
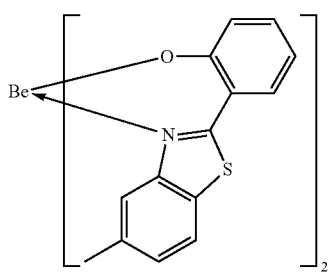
H228
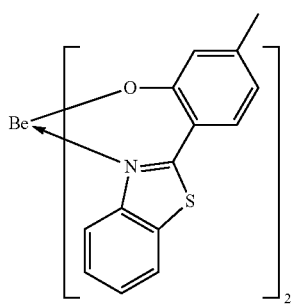

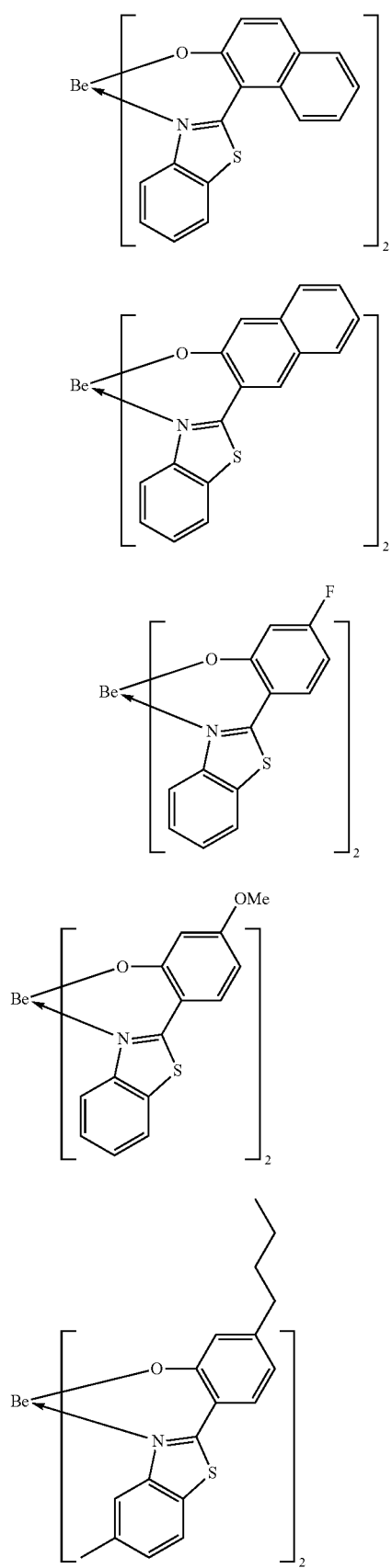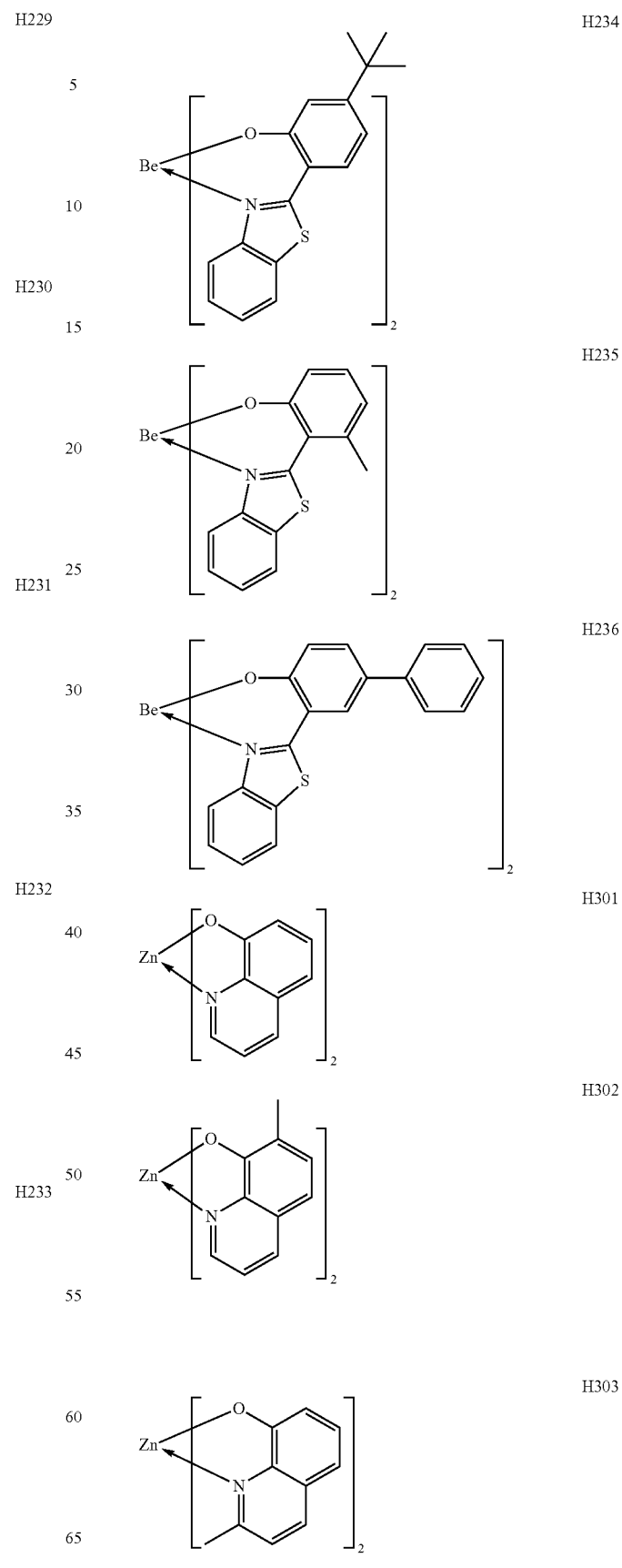

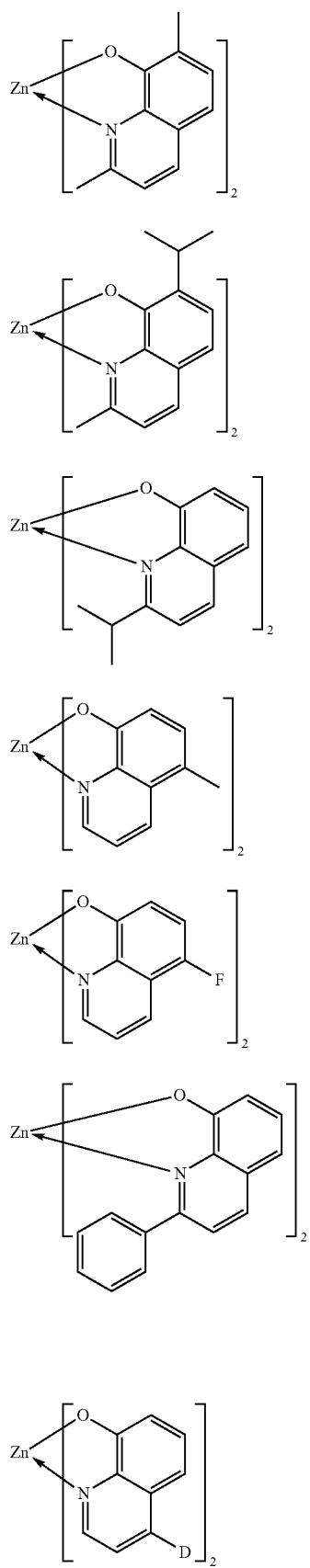
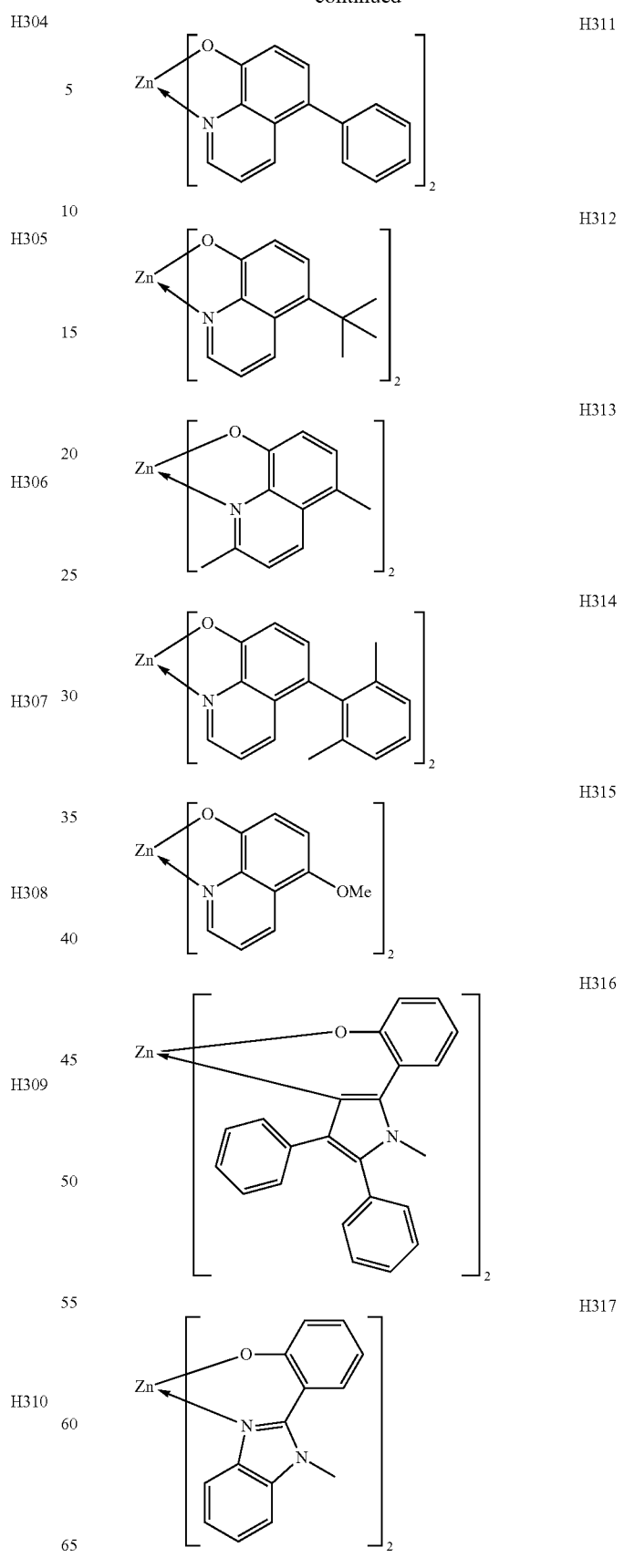

H318

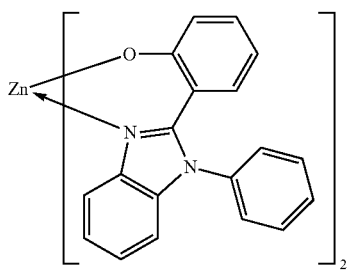

The exemplified compounds can be classified into several groups depending on a relationship between a ligand and a metal from the viewpoint of the stability of a metal complex itself.

Here, for ligands represented in the following type I to type III, distances between a nitrogen atom and oxygen atom included in each of the ligands and serving to coordinate to a metal atom are compared. The distances were each determined as follows: the stable structure of each of the ligands was calculated by employing an MM2 method as molecular mechanical calculation, and then the distance between the nitrogen atom and the oxygen atom was calculated from the structure.

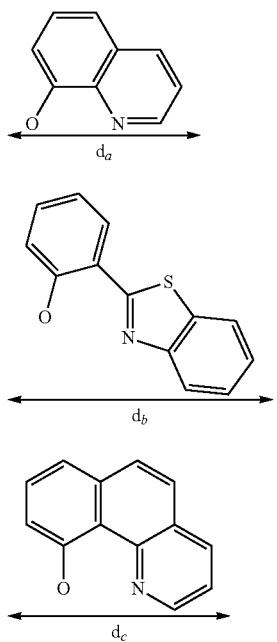

[Type I]

[Type II]

[Type III]

As a result of the calculation, the $d_a$ of a quinolinol ligand (type I) was found to be 2.68 Å, the $d_b$ of a phenylbenzothiazole ligand (type II) was found to be 2.60 Å, and the $d_c$ of a benzoquinolinol ligand (type III) was found to be 2.52 Å.

Meanwhile, the respective metal ionic radii of Mg, Zn, and Be are 0.75 Å, 0.83 Å, and 0.30 Å, respectively. In that case, Mg and Zn as metals having large ionic radii are suitable for the quinolinol ligand as the type I, and Be as a metal having a small metal ionic radius is suitable for the phenylbenzoxazole ligand as the type III. By the same reason, Be is also suitable for the phenylbenzothiazole ligand or the benzoquinolinol ligand. In actuality, when Mg or Zn is selected as a metal atom to be incorporated into a complex, it is difficult to synthesize a complex containing the benzoquinolinol ligand in which the distance between the nitrogen atom and the oxygen atom is long.

The metal complexes represented by Exemplified Compounds H101 to H115 are each a complex in which a central metal is Mg and a ligand is a quinolinol derivative. The quinolinol derivative is a ligand capable of producing a stable complex based on the ionic radius of Mg and is a compound having a small molecular weight. Accordingly, the complex can sublimate at a low sublimation temperature. The metal complexes represented by H116 to H118 are each a complex in which a central metal is Mg and a ligand is a phenylimidazole derivative. According to calculation, a distance between a nitrogen atom and oxygen atom in the phenylimidazole derivative is 2.56 Å, and hence the ligand can complex Mg. The ligand itself has a wide bang gap and hence the ligand is suitable for obtaining a high $T_1$ energy. The metal complexes represented by H119 to H125 are each a complex in which a central metal is Mg and a ligand is a phenylbenzoxazole derivative. A benzoxazole ring is a stable heterocycle. In addition, according to calculation, a distance between a nitrogen atom and oxygen atom in the benzoxazole derivative is 2.69 Å, and hence the ligand can produce a stable Mg complex. In addition, the ligand is a ligand suitable for the utilization of a high $T_1$ energy because of its wide bang gap. Therefore, an organic light-emitting element having high luminous efficiency can be obtained. The metal complexes represented by H126 to H136 are each a complex in which a central metal is Mg and a ligand is a phenylbenzothiazole derivative. A benzothiazole ring is a stable heterocycle and is a ligand capable of producing the most stable complex. Accordingly, the ligand is suitable for improving the stability and element lifetime of a element. By the way, introducing a substituent into any one of the ligands described above can suppress its stacking. Accordingly, the introduction can improve the sublimability of a complex and can change the band gap of the complex. It should be noted that a carbon atom adjacent to the nitrogen atom has high activity and hence the activity of the carbon atom can be controlled through substitution with a methyl group or an isopropyl group.

H201 to H206 are each a complex in which a central metal is Be and a ligand is a quinolinol derivative. Although the stability of each of the complexes is not very high in consideration of the ionic radius of a Be atom, the complex can sublimate at a low sublimation temperature because of its small molecular weight. H207 to H215 are each a complex in which a central metal is Be and a ligand is a benzoquinolinol derivative. A benzoquinolinol ring is a stable heterocycle. In addition, in consideration of the ionic radius of Be, the complex containing the benzoquinolinol ligand is a stable complex out of the Be complexes, and hence can provide a high-efficiency and long-lifetime organic light-emitting element. H216 to H218 are each a metal complex in which a central metal is Be, and each have a ligand having a wide band gap and suitable upon utilization of a high $T_1$ energy. Therefore, a high-efficiency organic light-emitting element can be obtained. H219 to H225 are each a complex in which a central metal is Be and a ligand is a phenylbenzoxazole derivative. A benzoxazole ligand is a stable heterocycle and is hence a ligand capable of producing a stable Be complex. In addition, the benzoxazole ligand is suitable for the utilization of a high $T_1$ energy and hence can provide a high-efficiency organic light-emitting element. H226 to H236 are each a complex in which a central metal is Be and a ligand is a phenylbenzothiazole derivative. A benzothiazole ligand is a stable heterocycle and is a ligand capable of producing the most stable Be complex. In addition, the complex has a $T_1$ energy suitable for red phosphorescence, and hence can provide a high-efficiency and long-lifetime organic light-emitting element.

By the way, introducing a substituent into any one of the ligands described above can suppress its stacking. Accordingly, the introduction can improve the sublimability of a complex and can change the band gap of the complex. It should be noted that a carbon atom adjacent to the nitrogen atom has high activity and hence the activity of the carbon atom can be controlled through substitution with a methyl group or an isopropyl group.

H301 to H315 are each a complex in which a central metal is Zn and a ligand is a quinolinol derivative. The ligand can produce an extremely stable complex based on the ionic radius of a Zn complex and has a small molecular weight, and hence the complex can sublimate at a low sublimation temperature. In addition, introducing a substituent suppresses the stacking of the ligand, and hence can improve the sublimability of the complex and can change the band gap of the complex. H316 to H318 are each a complex in which a central metal is Zn and a ligand is a phenylimidazole derivative. A distance between a nitrogen atom and oxygen atom in the ligand is 2.56 Å, and hence the ligand can complex Zn. The ligand itself has a wide bang gap and hence the ligand is suitable upon utilization of a high $T_1$ energy. Introducing a substituent into any one of the ligands described above can suppress its stacking. Accordingly, the introduction can improve the sublimability of a complex and can change the band gap of the complex. It should be noted that a carbon atom adjacent to the nitrogen atom has high activity and hence the activity of the carbon atom can be controlled through substitution with a methyl group or an isopropyl group.

(7) Constituent Material Except Iridium Complex and Metal Complex

As described above, the organic compound layer (preferably the emission layer) of the organic light-emitting element of the present invention contains at least the iridium complex represented by the general formula [1] and the metal complex compound represented by the general formula [5], provided that in the present invention, conventionally known low-molecular weight and high-molecular weight materials can each be used as required in addition to these compounds. More specifically, a hole-injectable/transportable material, a light emission assist material, an electron-injectable/transportable material, or the like can be used together with the iridium complex and the metal complex compound.

Examples of those materials are listed below.

The hole-injectable/transportable material is preferably a material having a high hole mobility so that the injection of a hole from the anode may be facilitated and the injected hole can be transported to the emission layer. In addition, the material is preferably a material having a high glass transition point for preventing the deterioration of film quality such as crystallization in the organic light-emitting element. Examples of the low-molecular weight and high-molecular weight materials each having hole-injecting/transporting performance include a triarylamine derivative, an arylcarbazole derivative, a phenylenediamine derivative, a stilbene derivative, a phthalocyanine derivative, a porphyrin derivative, poly(vinyl carbazole), poly(thiophene), and other conductive polymers. Further, the hole-injectable/transportable material is suitably used for the electron-blocking layer as well.

Specific examples of a compound to be used as the hole-injectable/transportable material are shown below. However, the compound is of course not limited thereto.

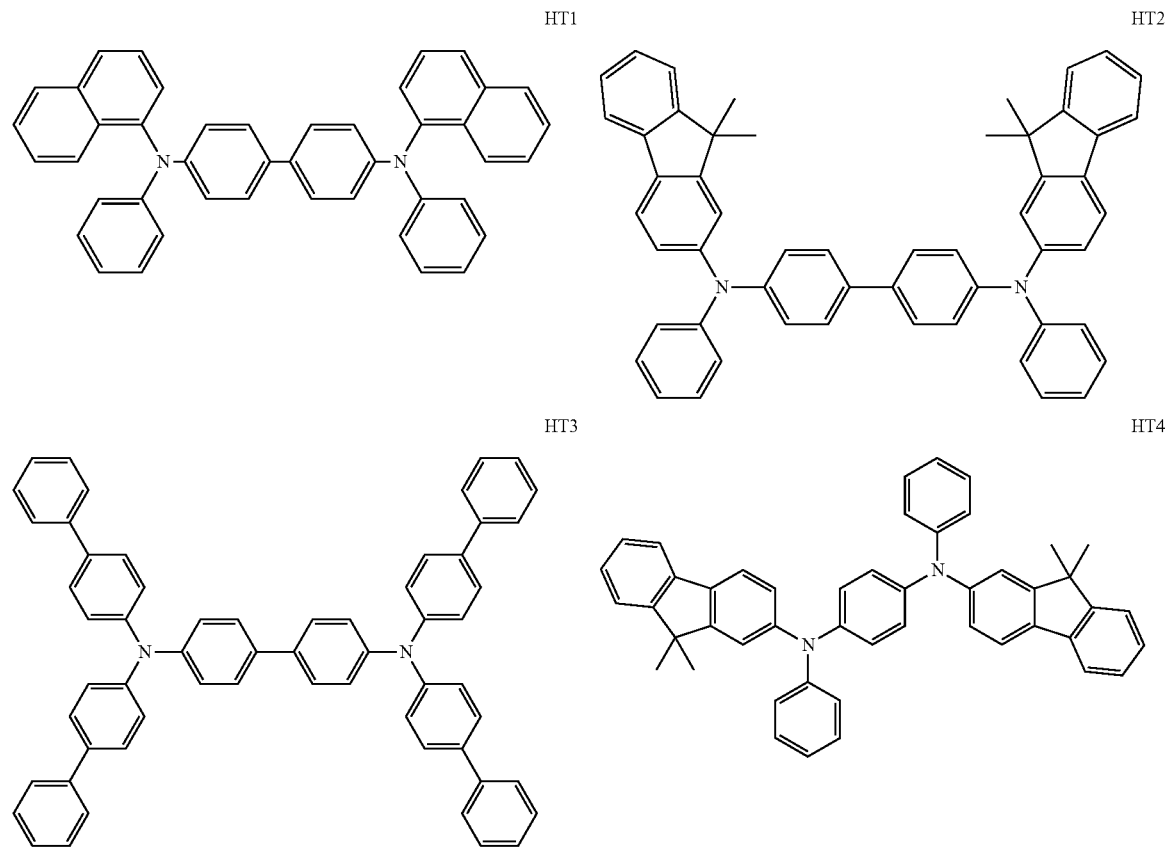

-continued
HT5
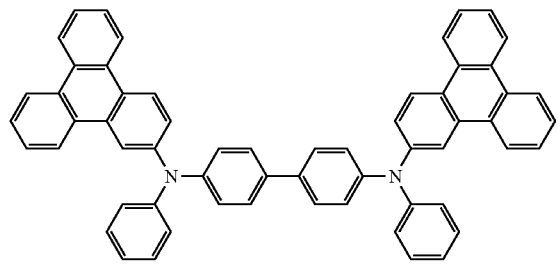
HT6
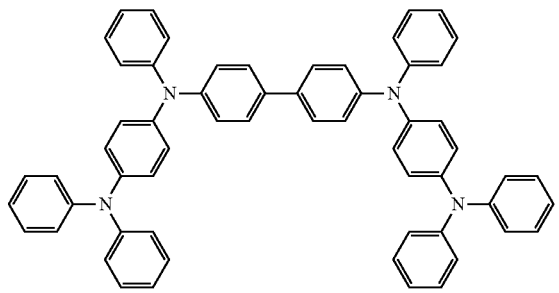
HT7
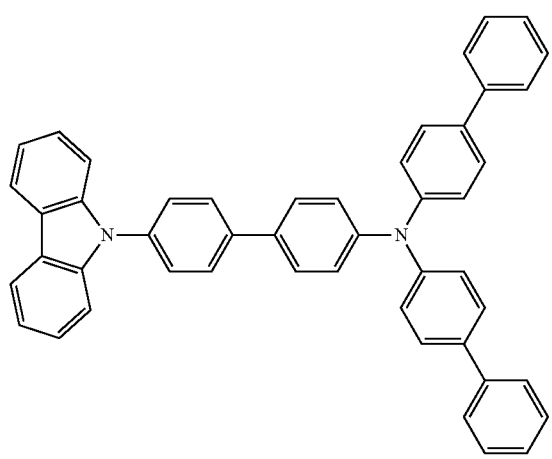
HT8
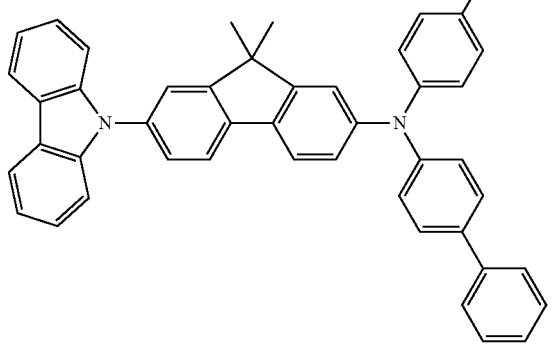
HT9
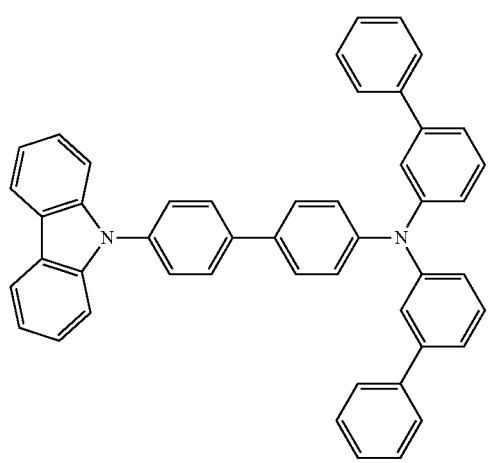
HT10
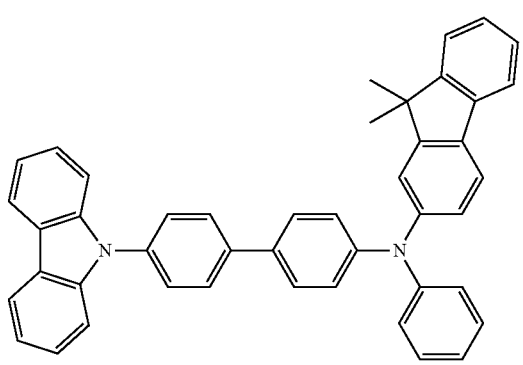
HT11
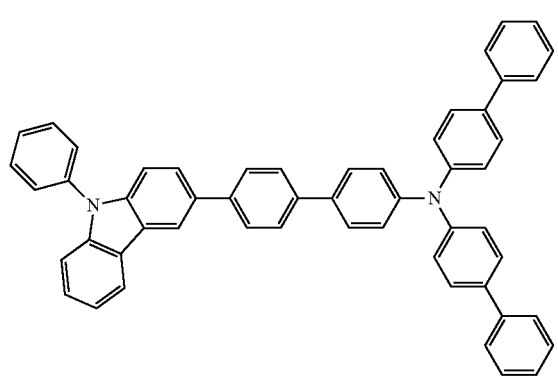
HT12
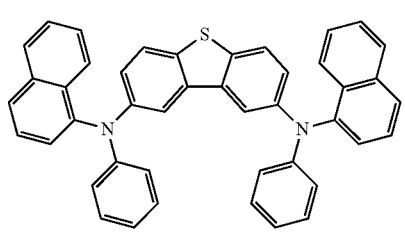

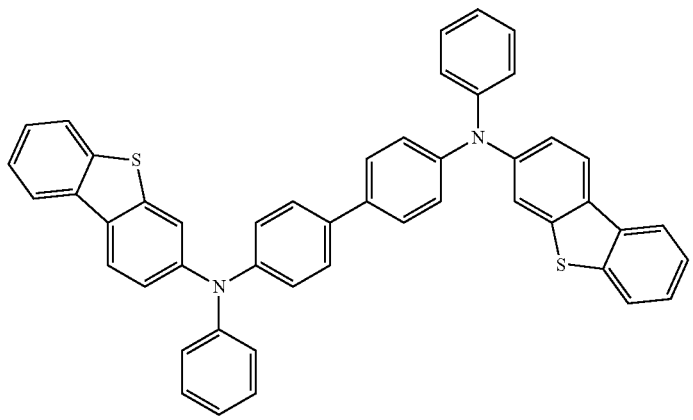

HT13

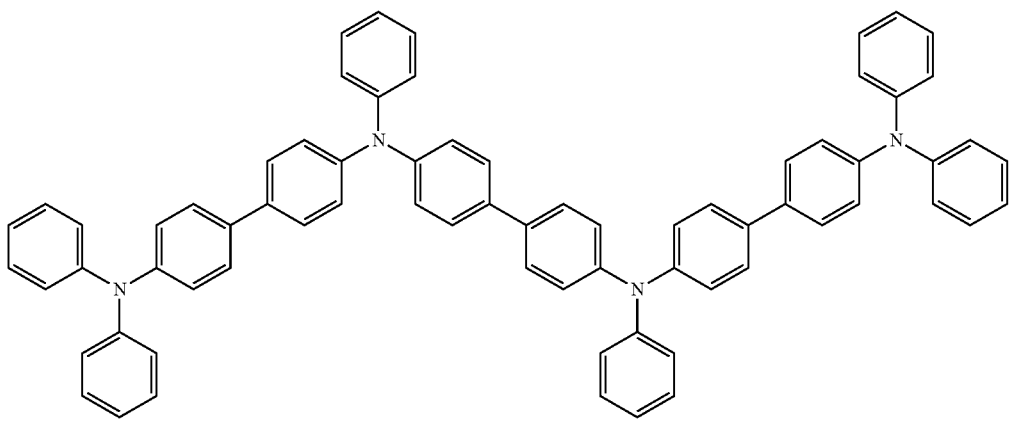

HT14

Examples of the light-emitting material mainly involved in a light-emitting function include: condensed ring compounds (such as a fluorene derivative, a naphthalene derivative, a pyrene derivative, a perylene derivative, a tetracene derivative, an anthracene derivative, and rubrene); a quinacridone derivative; a coumarin derivative; a stilbene derivative; an organic aluminum complex such as tris(8-quinolinolato)aluminum; a platinum complex; a rhenium complex; a copper complex; a europium complex; a ruthenium complex; and polymer derivatives such as a poly(phenylene vinylene) derivative, a poly(fluorene) derivative, and a poly(phenylene) derivative in addition to the iridium complex represented by the general formula [1] or a derivative thereof.

Specific examples of a compound to be used as the light-emitting material are shown below. However, the compound is of course not limited thereto.

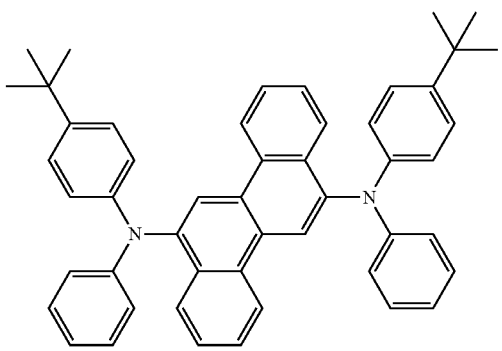

BD1

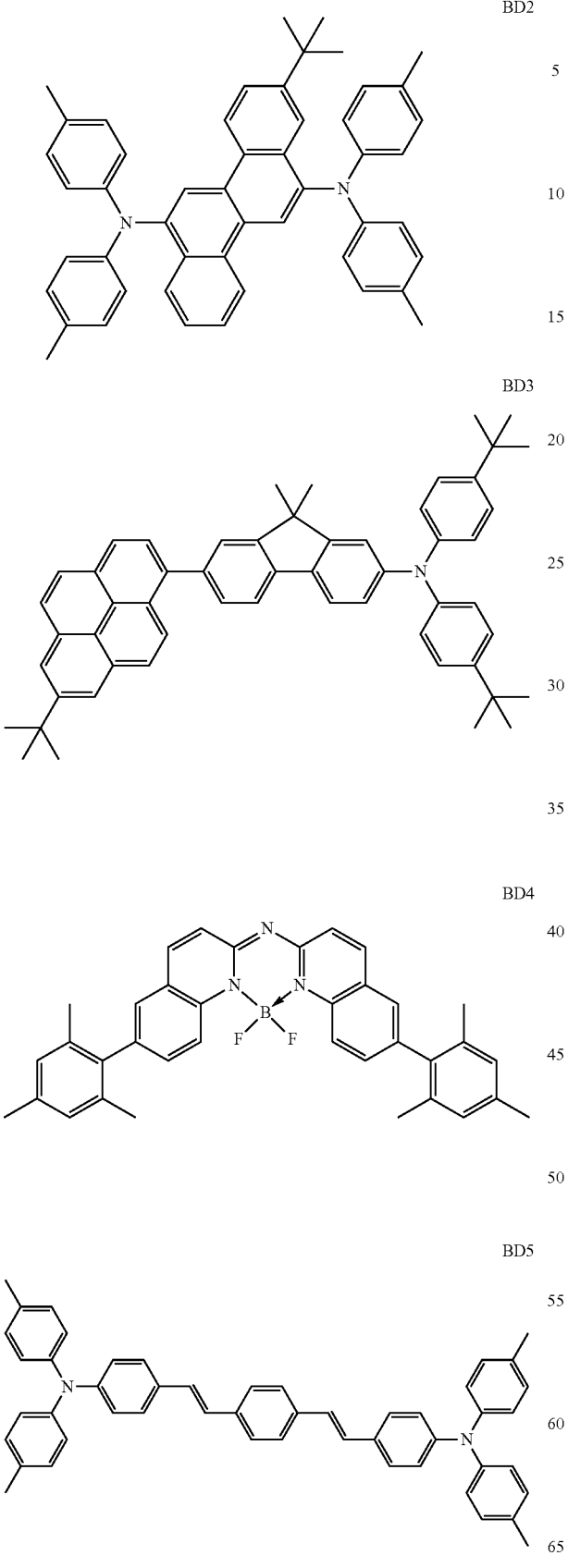
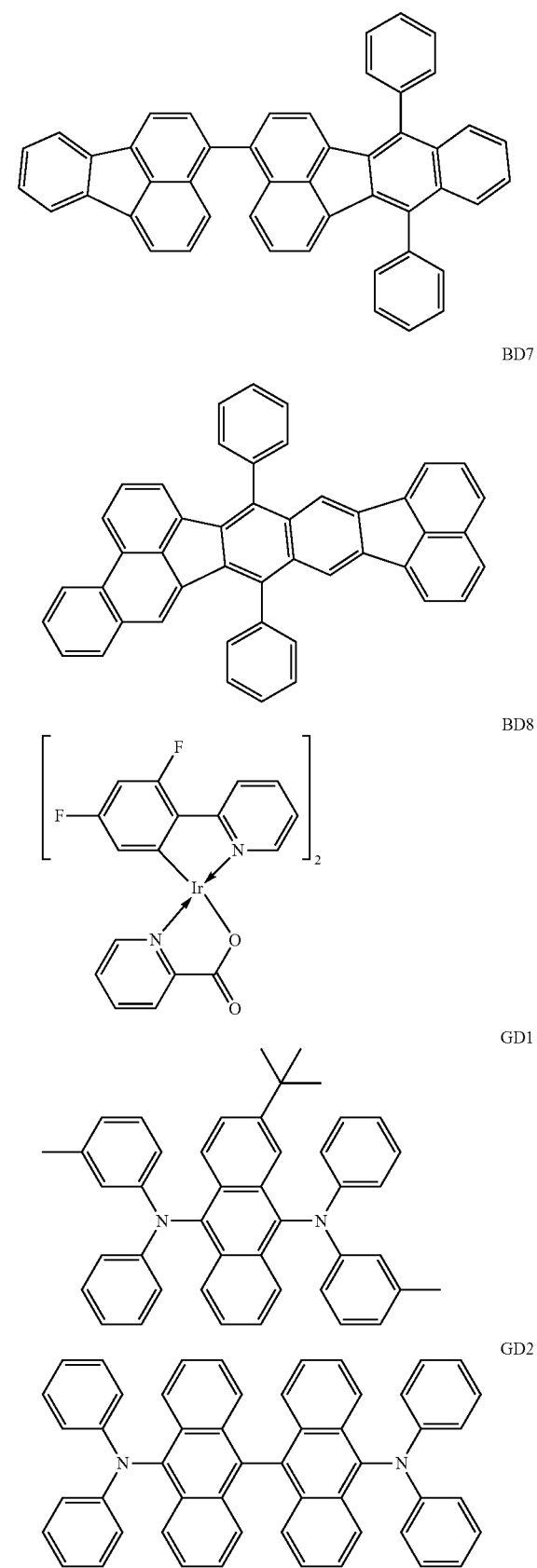

GD3 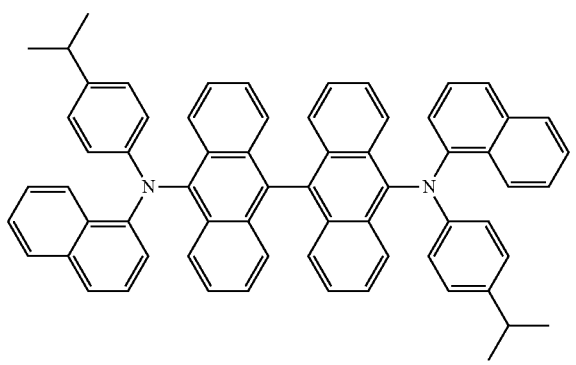
GD4 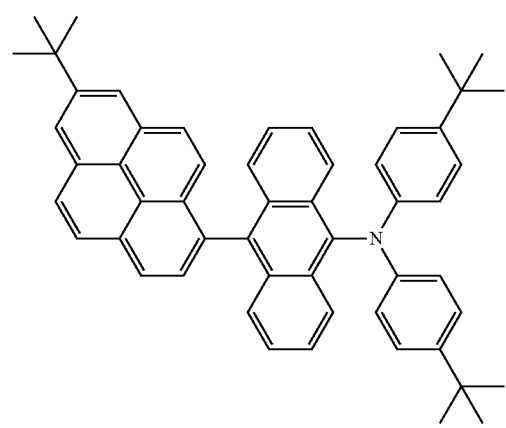
GD5 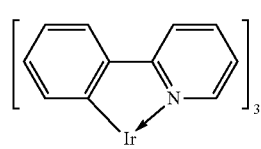
GD6 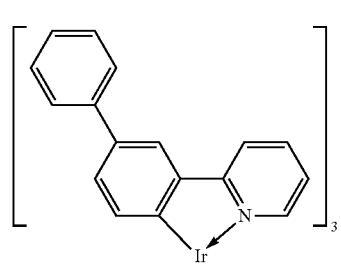
GD7 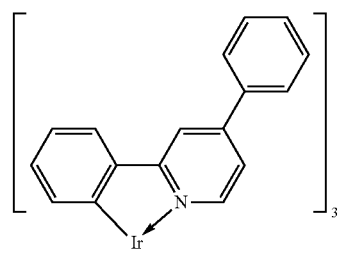
GD8 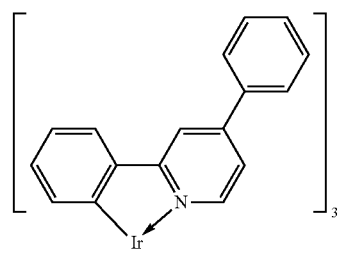
RD1 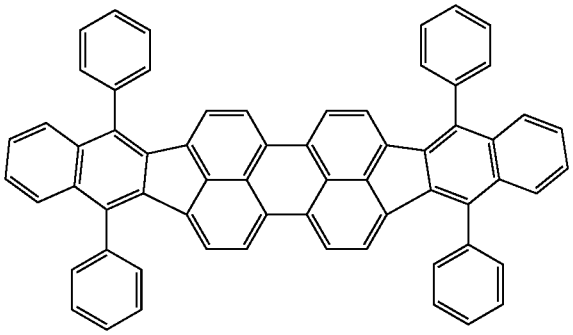
RD2 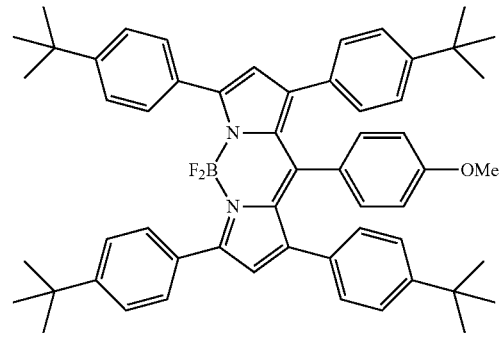
RD3 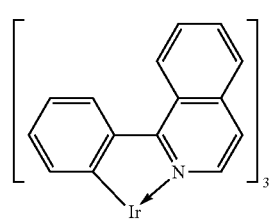
RD4 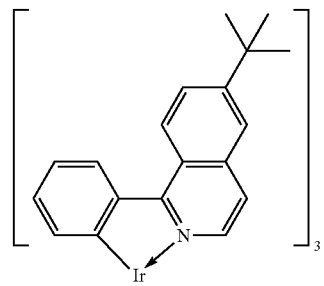

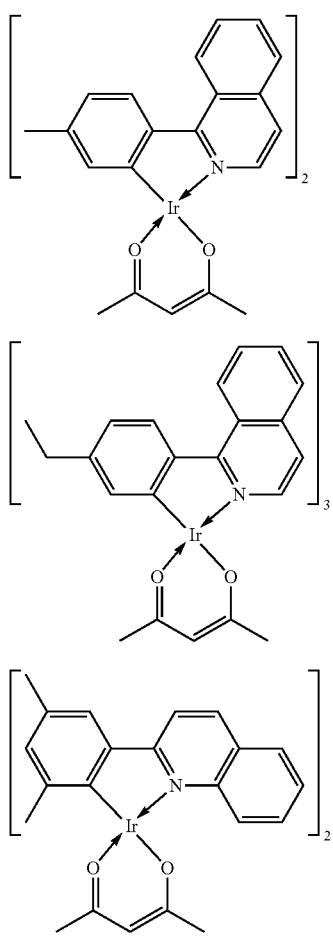

RD5

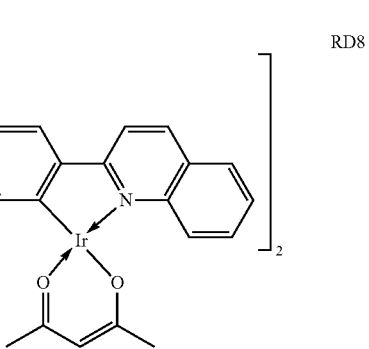

RD6

RD7

RD8

Examples of the host or assist material to be incorporated into the emission layer include: an aromatic hydrocarbon compound or a derivative thereof; a carbazole derivative; a dibenzofuran derivative; a dibenzothiophene derivative; an organic aluminum complex such as tris(8-quinolinolato) aluminum; and an organic beryllium complex in addition to the heterocycle-containing compound represented the general formula [5].

Specific examples of a compound to be used as the host or assist material to be incorporated into the emission layer are shown below. However, the compound is of course not limited thereto.

EM1

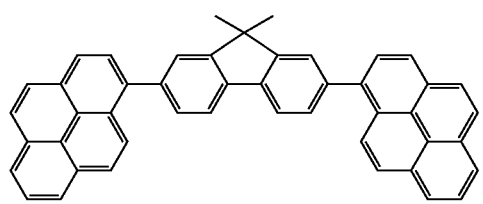

EM2

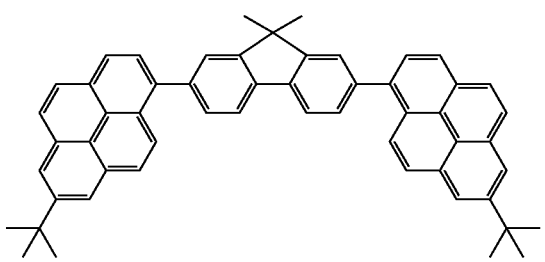

EM3

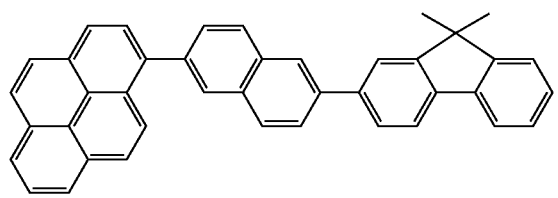

EM4

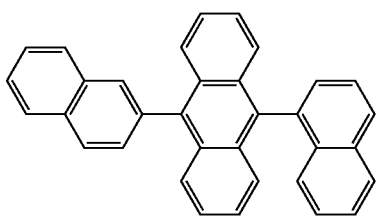

-continued
EM5
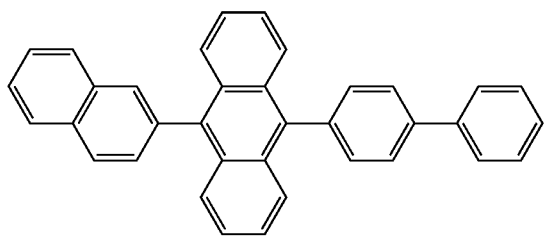
EM6
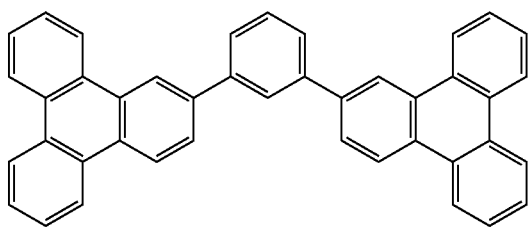
EM7
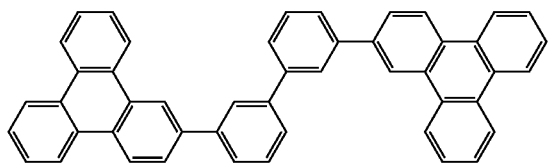
EM8
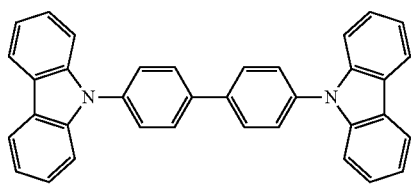
EM9
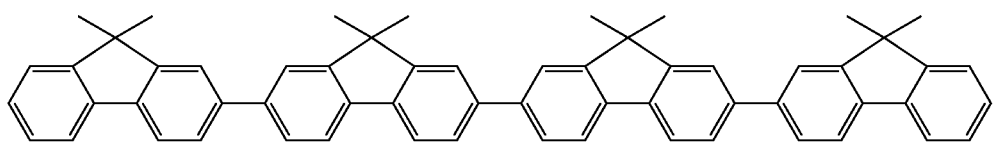
EM10
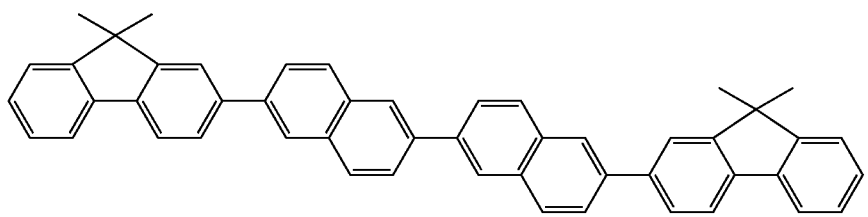
EM11
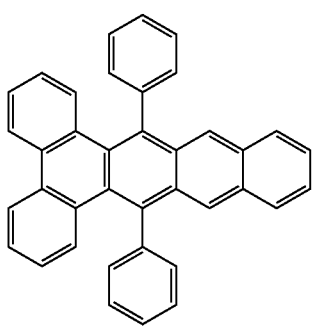
EM12
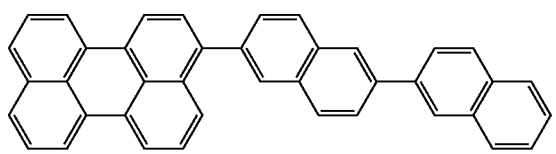
EM13
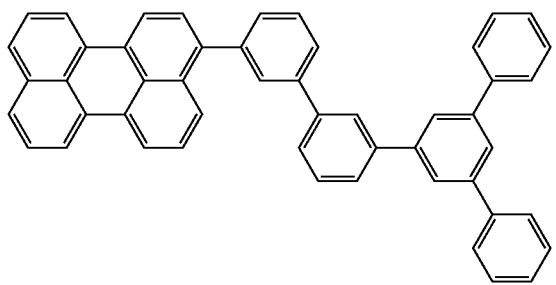
EM14
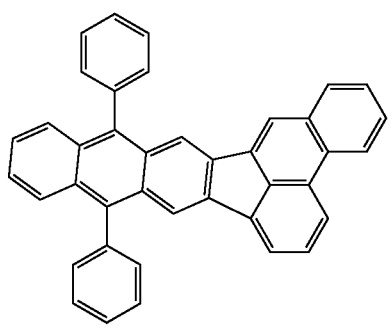

EM15
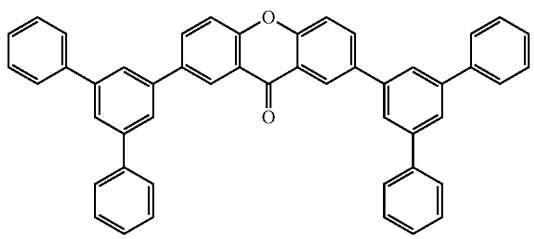

EM16
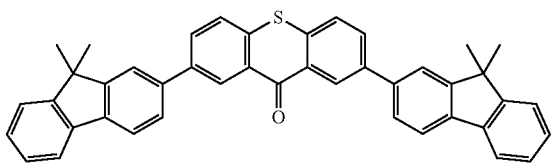

EM17
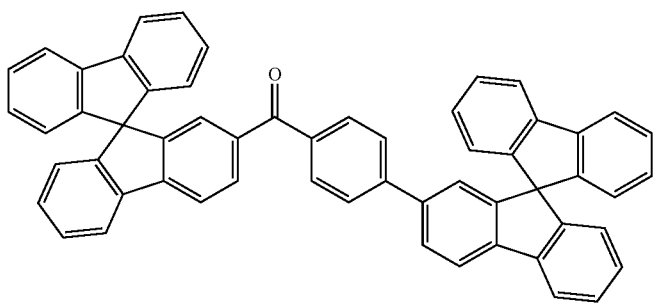

The electron-injectable/transportable material can be arbitrarily selected from materials that allow electrons to be easily injected from the cathode and can transport the injected electrons to the emission layer in consideration of, for example, the balance with the hole mobility of the hole-transportable material. Examples of the material having electron-injecting performance and electron-transporting performance include an oxadiazole derivative, an oxazole derivative, a pyrazine derivative, a triazole derivative, a triazine derivative, a quinoline derivative, a quinoxaline derivative, a phenanthroline derivative, and an organic aluminum complex. Further, the electron-injectable/transportable material is suitably used for the hole-blocking layer as well.

Specific examples of a compound to be used as the electron-injectable/transportable material are shown below. However, the compound is of course not limited thereto.

ET2
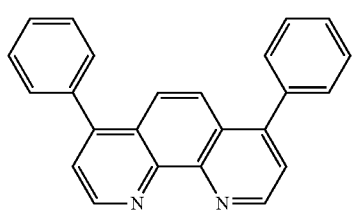

ET2
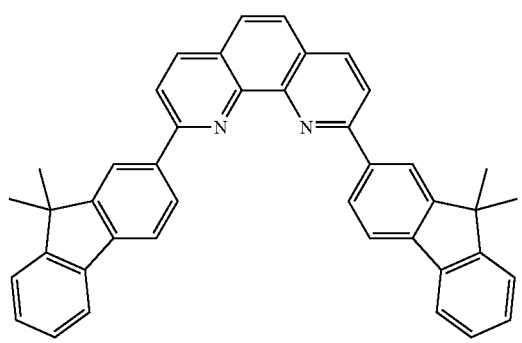

ET3
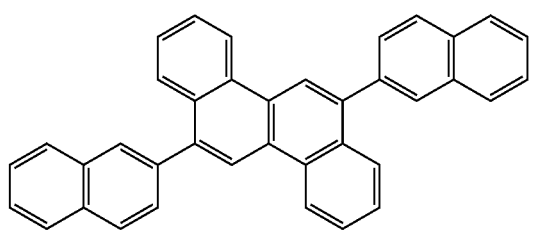

ET4

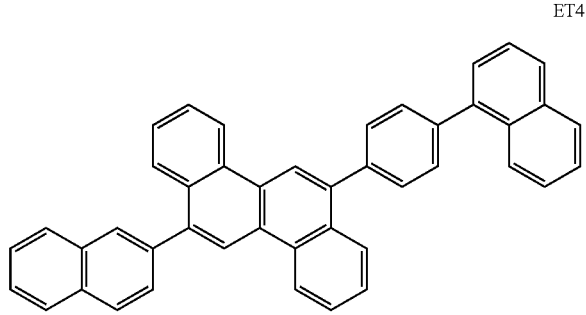

ET5

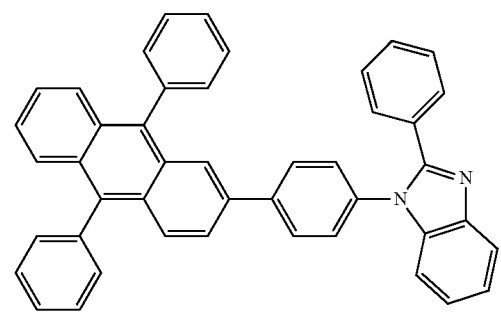

ET6

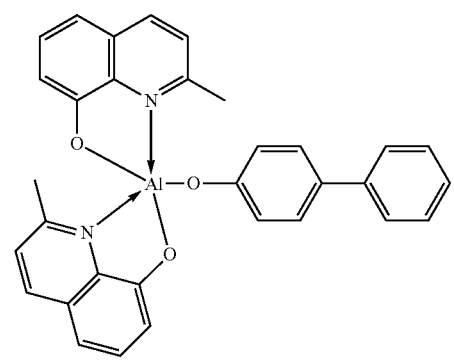

ET7

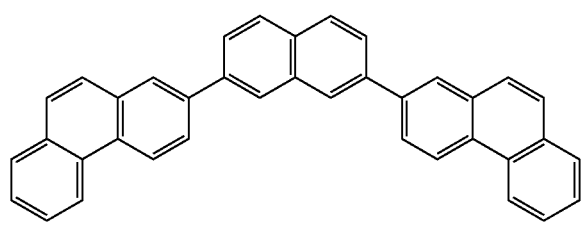

ET8

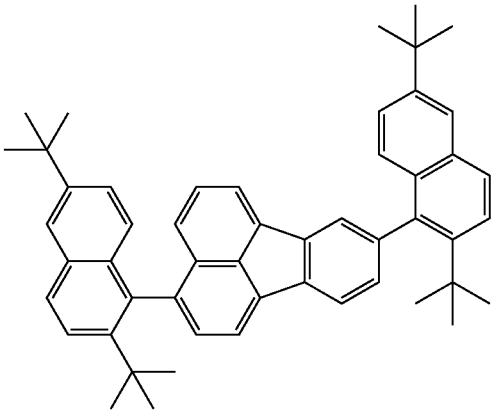

A constituent material for the anode desirably has as large a work function as possible. Examples thereof may include: metal simple substances such as gold, platinum, silver, copper, nickel, palladium, cobalt, selenium, vanadium, and tungsten or alloy obtained by combining these metal simple substances; metal oxides such as tin oxide, zinc oxide, indium oxide, indium tin oxide (ITO), and indium zinc oxide; and conductive polymers such as polyaniline, polypyrrole, and polythiophene.

One kind of those electrode substances may be used alone, or two or more kinds thereof may be used in combination. In addition, the anode may be of a single-layer construction or may be of a multilayer construction.

On the other hand, a constituent material for the cathode desirably has as small a work function as possible. Examples thereof include: alkali metals such as lithium; alkaline earth metals such as calcium; and metal simple substances such as aluminum, titanium, manganese, silver, lead, and chromium. Alternatively, alloys obtained by combining those metal simple substances can be used. For example, a magnesium-silver alloy, an aluminum-lithium alloy, or an aluminum-magnesium alloy can be used. A metal oxide such as indium tin oxide (ITO) can also be utilized. One kind of those electrode substances may be used alone, or two or more kinds thereof may be used in combination. In addition, the cathode may be of a single-layer construction or may be of a multilayer construction.

The organic compound layer (such as the hole-injecting layer, the hole-transporting layer, the electron-blocking layer, the emission layer, the hole-blocking layer, the electron-transporting layer, or the electron-injecting layer) for forming the organic light-emitting element of the present invention is formed by the following method.

A dry process such as a vacuum vapor deposition method, an ionized vapor deposition method, sputtering, or a plasma process can be used for the formation of the organic compound layer for forming the organic light-emitting element of the present invention. In addition, a wet process involving dissolving the constituent materials in an appropriate solvent and forming a layer by a known application method (such as spin coating, dipping, a casting method, an LB method, or an ink jet method) can be used instead of the dry process.

Here, when the layer is formed by the vacuum vapor deposition method, the solution application method, or the like, the layer hardly undergoes crystallization or the like and is excellent in stability over time. In addition, when the layer is formed by the application method, the film can be formed by using the constituent materials in combination with an appropriate binder resin.

Examples of the binder include, but not limited to, a polyvinyl carbazole resin, a polycarbonate resin, a polyester resin, an ABS resin, an acrylic resin, a polyimide resin, a phenol resin, an epoxy resin, a silicone resin, and a urea resin.

In addition, one kind of those binder resins may be used alone as a homopolymer or a copolymer, or two or more kinds thereof may be used as a mixture. Further, a known additive such as a plasticizer, an antioxidant, or a UV absorber may be used in combination as required.

(8) Application of Organic Light-Emitting Element of the Present Invention

The organic light-emitting element of the present invention can be used as a constituent member for a display apparatus or lighting apparatus. In addition, the element finds use in applications such as an exposure light source for an image-forming apparatus of an electrophotographic system, a backlight for a liquid crystal display apparatus, and a light-emitting apparatus including a white light source and a color filter. Examples of the color filter include filters that transmit light beams having three colors, i.e., red, green, and blue colors.

A display apparatus of the present invention includes the organic light-emitting element of the present invention in its display portion. It should be noted that the display portion includes multiple pixels.

In addition, the pixels each have the organic light-emitting element of the present invention and a transistor as an example of an active element (switching element) or amplifying element for controlling emission luminance, and the anode or cathode of the organic light-emitting element and the drain electrode or source electrode of the transistor are electrically connected to each other. Here, the display apparatus can be used as an image display apparatus for a PC or the like. The transistor is, for example, a TFT element and the TFT element is provided on, for example, the insulating surface of a substrate. In addition, the TFT element preferably includes an electrode formed of a transparent oxide semiconductor.

The display apparatus may be an information processing apparatus that includes an image input portion for inputting image information from, for example, an area CCD, a linear CCD, or a memory card, and displays an input image on its display portion.

In addition, the display portion of an imaging apparatus or inkjet printer may have a touch panel function. The drive system of the touch panel function is not particularly limited.

In addition, the display apparatus may be used in the display portion of a multifunction printer.

A lighting apparatus is an apparatus for lighting, for example, the inside of a room. The lighting apparatus may emit light having any one of the following colors: a white color (having a color temperature of 4,200 K), a daylight color (having a color temperature of 5,000 K), and colors ranging from blue to red colors.

A lighting apparatus of the present invention includes the organic light-emitting element of the present invention and an AC/DC converter circuit (circuit for converting an AC voltage into a DC voltage) connected to the organic light-emitting element. It should be noted that the lighting apparatus may further have a color filter.

An image-forming apparatus of the present invention is an image-forming apparatus including: a photosensitive member; charging unit for charging the surface of the photosensitive member; exposing unit for exposing the photosensitive member to form an electrostatic latent image; and a developing unit for developing the electrostatic latent image formed on the surface of the photosensitive member. Here, the exposing unit to be provided in the image-forming apparatus includes the organic light-emitting element of the present invention.

In addition, the organic light-emitting element of the present invention can be used as a constituent member for an exposing apparatus for exposing a photosensitive member. An exposing apparatus including a plurality of the organic light-emitting elements of the present invention is, for example, an exposing apparatus in which the organic light-emitting elements of the present invention are placed to form a line along a predetermined direction.

Next, the display apparatus of the present invention is described with reference to the drawing. FIGURE is a schematic sectional view illustrating an example of a display apparatus including an organic light-emitting element and a TFT element connected to the organic light-emitting element. It should be noted that the organic light-emitting element of the present invention is used as the organic light-emitting element constituting a display apparatus 1 of FIGURE The display apparatus 1 of FIGURE includes a substrate 11 made of glass or the like and a moisture-proof film 12 for protecting a TFT element or organic compound layer, the film being provided on the substrate. In addition, reference numeral 13 represents a metal gate electrode 13, reference numeral 14 represents a gate insulating film 14, and reference numeral 15 represents a semiconductor layer.

A TFT element 18 includes the semiconductor layer 15, a drain electrode 16, and a source electrode 17. An insulating film 19 is provided on the TFT element 18. An anode 21 constituting the organic light-emitting element and the source electrode 17 are connected to each other through a contact hole 20.

It should be noted that a system for the electrical connection between the electrode (anode or cathode) in the organic light-emitting element and the electrode (source electrode or drain electrode) in the TFT is not limited to the aspect illustrated in FIGURE. In other words, one of the anode and the cathode, and one of the source electrode and drain electrode of the TFT element have only to be electrically connected to each other.

Although multiple organic compound layers are illustrated like one layer in the display apparatus 1 of FIGURE, an organic compound layer 22 may be multiple layers. A first protective layer 24 and second protective layer 25 for suppressing the deterioration of the organic light-emitting element are provided on a cathode 23.

When the display apparatus 1 of FIGURE is a display apparatus that emits white light, an emission layer in the organic compound layer 22 in FIGURE may be a layer obtained by mixing a red light-emitting material, a green light-emitting material, and a blue light-emitting material. In addition, the layer may be a laminated emission layer obtained by laminating a layer formed of the red light-emitting material, a layer formed of the green light-emitting material, and a layer formed of the blue light-emitting material. Further, alternatively, the following aspect is permitted: the layer formed of the red light-emitting material, the layer formed of the green light-emitting material, and the layer formed of the blue light-emitting material are, for example, arranged side by side to form domains in one emission layer.

Although the transistor is used as a switching element in the display apparatus 1 of FIGURE, an MIM element may be used instead of the transistor as the switching element.

In addition, the transistor to be used in the display apparatus 1 of FIGURE is not limited to a transistor using a monocrystalline silicon wafer and may be a thin-film transistor including an active layer on the insulating surface of a substrate. A thin-film transistor using monocrystalline silicon as the active layer, a thin-film transistor using non-monocrystalline silicon such as amorphous silicon or microcrystalline silicon as the active layer, or a thin-film transistor using a non-monocrystalline oxide semiconductor such as an indium zinc oxide or an indium gallium zinc oxide as the active layer is also permitted. It should be noted that the thin-film transistor is also called a TFT element.

The transistor in the display apparatus 1 of FIG. 1 may be formed in a substrate such as an Si substrate. Here, the phrase "formed in a substrate" means that the transistor is produced by processing the substrate itself such as an Si substrate. In other words, the presence of the transistor in the substrate can be regarded as follows: the substrate and the transistor are integrally formed.

Whether the transistor is provided in the substrate is selected depending on definition. In the case of, for example, a definition of about a QVGA per inch, the organic light-emitting element is preferably provided in the Si substrate.

As described above, driving the display apparatus using the organic light-emitting element of the present invention enables display that has good image quality and is stable over a long time period.

EXAMPLES

Synthesis Examples 1 and 2

Synthesis of Exemplified Compounds Ir-101 and 201

Ir-101 and Ir-201 were synthesized according to the following synthesis scheme with reference to, for example, PTL 1 and NPLS 1 to 4.

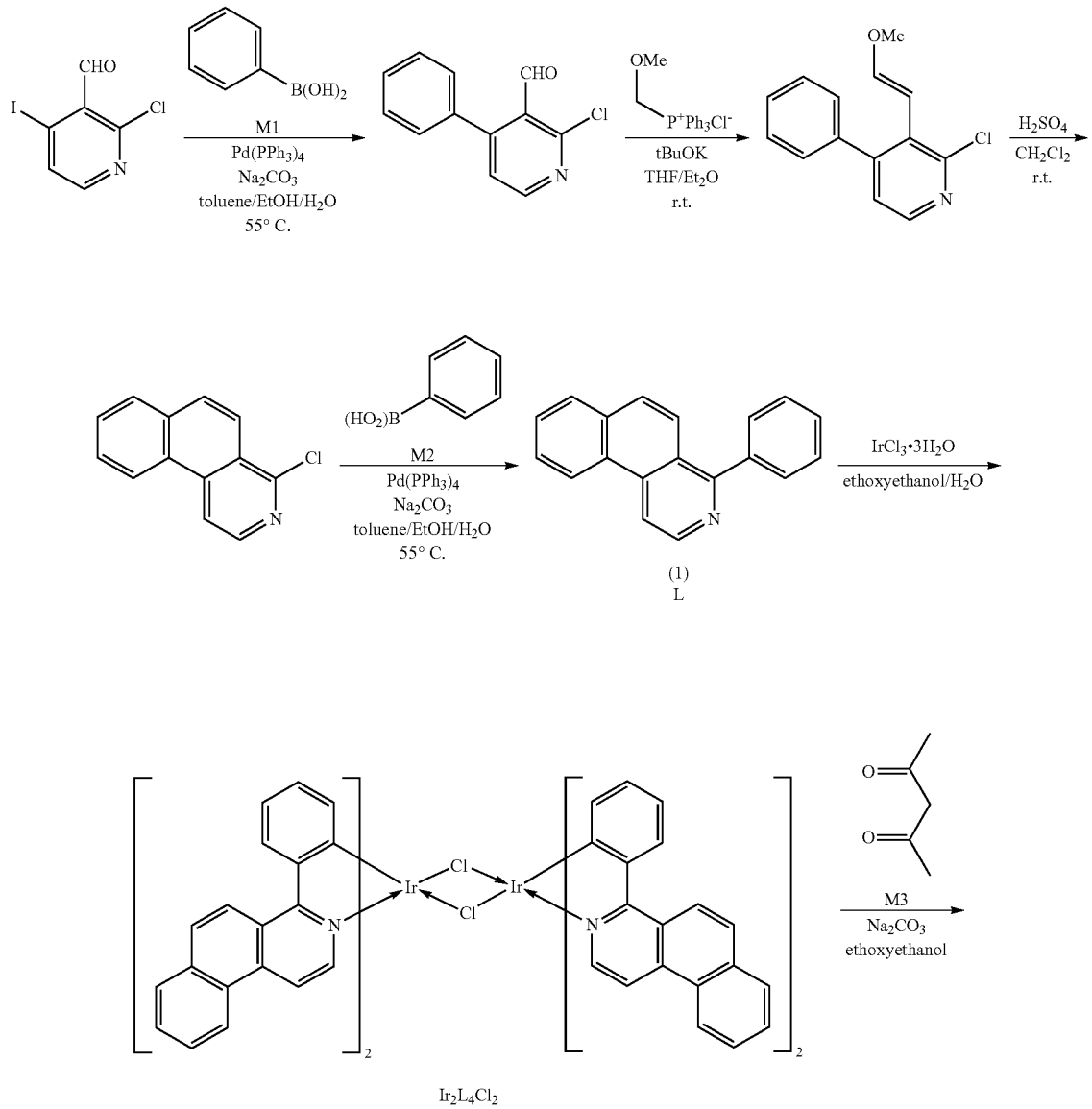

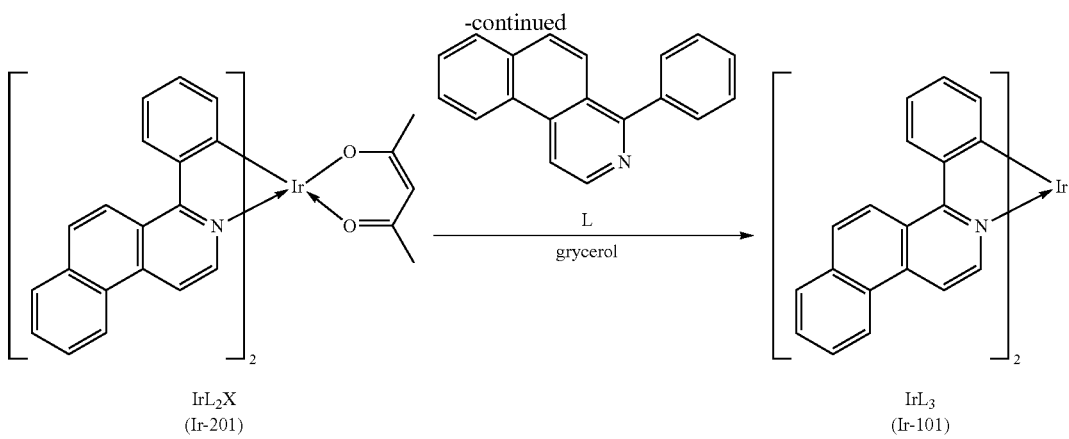

IrL₂X
(Ir-201)

IrL₃
(Ir-101)

Specifically, the synthesis was performed through the following steps:
(1) the synthesis of a ligand L (benzo[f]isoquinoline derivative);
(2) the synthesis of a chloro-crosslinked complex (Ir₂L₄Cl₂) having the ligand L;
(3) the synthesis of a complex (IrL₂X) having an auxiliary ligand X (the synthesis of Ir-201, Synthesis Example 1); and
(4) the synthesis of a complex (IrL₃) to which the three ligands L's are coordinated (the synthesis of Ir-101, Synthesis Example 2).

Ir-101 and Ir-201 thus obtained were each identified by matrix-assisted laser desorption/ionization time-of-flight mass spectrometry (MALDI-TOF-MS). Further, the PL spectrum of each of the resultant iridium complexes in a toluene dilute solution having a concentration of 1×10⁻⁵ M was measured with a UV-visible spectrophotometer and its maximum emission peak wavelength $\lambda_{max}$ was measured (excitation wavelength: 510 nm). Table 1 shows the results.

Synthesis Examples 3 to 16

Iridium complexes shown in Table 1 were each synthesized by the same synthesis method as that of Synthesis Examples 1 and 2 except that in the synthesis scheme of Synthesis Examples 1 and 2, the compounds (M1 to M3) serving as synthesis raw materials were appropriately changed. The structures of the resultant iridium complexes were confirmed by performing identification in the same manner as in the iridium complexes obtained in Synthesis Examples 1 and 2. In addition, their maximum emission peak wavelengths were measured by PL spectrum measurement. Table 1 shows the results.

Synthesis Example 17

Synthesis of Exemplified Compound Ir-515

Ir-515 was synthesized according to the following synthesis scheme with reference to, for example, PTL 5.

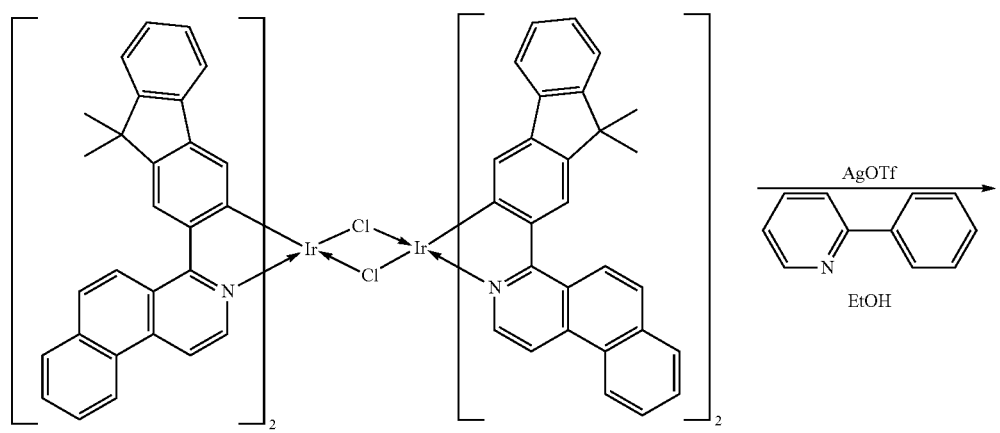

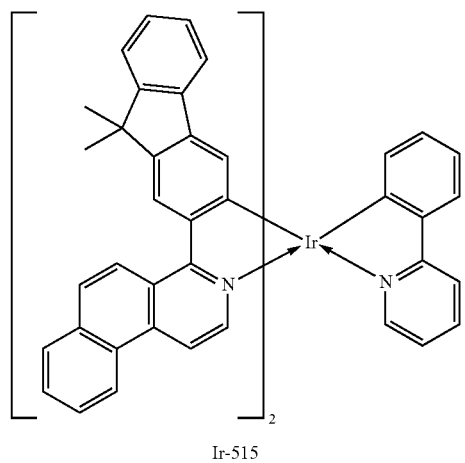

Ir-515

The structure of Ir-515 thus obtained was confirmed by performing identification in the same manner as in the iridium complexes obtained in Synthesis Examples 1 and 2. In addition, its maximum emission peak wavelength was measured by PL spectrum measurement. Table 1 shows the results.

Synthesis Example 18

Synthesis of Exemplified Compound Ir-516

Ir-516 was synthesized by the same synthesis method as that of Synthesis Example 17 except that in Synthesis Example 17, the loading amount of the auxiliary ligand (phenylpyridine) was appropriately regulated. The structure of Ir-516 thus obtained was confirmed by performing identification in the same manner as in the iridium complexes obtained in Synthesis Examples 1 and 2. In addition, its maximum emission peak wavelength was measured by PL spectrum measurement. Table 1 shows the results.

TABLE 1

| | Ir complex | MS (calculated value) | MS (measured value) | $\lambda_{max}$ (nm) |
|---|---|---|---|---|
| Synthesis Example 1 | Ir-101 | 955.25 | 955.44 | 592 |
| Synthesis Example 2 | Ir-201 | 800.20 | 800.38 | 601 |
| Synthesis Example 3 | Ir-205 | 828.23 | 828.29 | 617 |
| Synthesis Example 4 | Ir-206 | 912.33 | 912.56 | 614 |
| Synthesis Example 5 | Ir-212 | 856.26 | 856.45 | 614 |
| Synthesis Example 6 | Ir-213 | 940.36 | 940.85 | 614 |
| Synthesis Example 7 | Ir-214 | 1024.45 | 1025.80 | 612 |
| Synthesis Example 8 | Ir-221 | 912.33 | 912.23 | 621 |
| Synthesis Example 9 | Ir-222 | 996.42 | 997.54 | 619 |
| Synthesis Example 10 | Ir-301 | 952.26 | 952.52 | 615 |
| Synthesis Example 11 | Ir-304 | 1064.39 | 1065.77 | 613 |
| Synthesis Example 12 | Ir-316 | 1036.36 | 1036.61 | 619 |
| Synthesis Example 13 | Ir-318 | 1148.48 | 1149.72 | 616 |
| Synthesis Example 14 | Ir-414 | 1012.36 | 1013.85 | 612 |
| Synthesis Example 15 | Ir-416 | 1032.33 | 1032.22 | 635 |
| Synthesis Example 16 | Ir-424 | 1276.36 | 1276.71 | 619 |
| Synthesis Example 17 | Ir-515 | 1087.35 | 1087.34 | 623 |
| Synthesis Example 18 | Ir-516 | 871.25 | 817.17 | 624 |

Synthesis Examples 19 to 21

Synthesis of Exemplified Compounds H101, H201, and H301

Exemplified Compounds H101, H201, and H301 were each synthesized according to the following synthesis scheme, specifically, by performing a complexation reaction in methanol involving using quinolin-8-ol as a starting raw material.

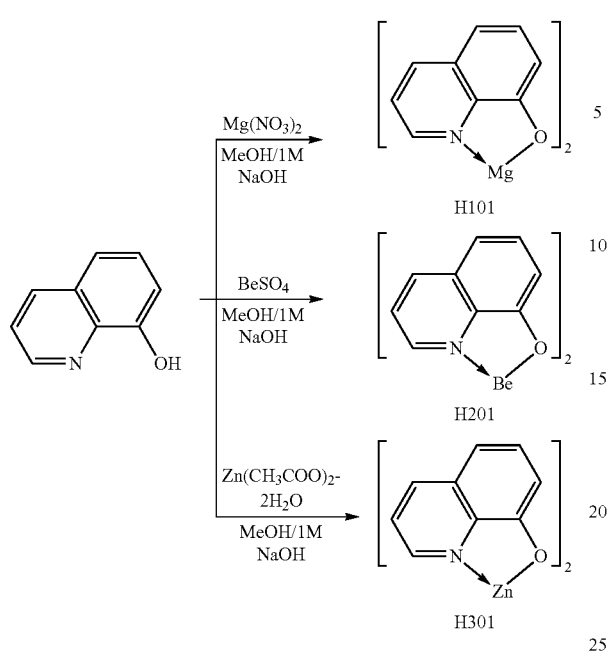

The resultant compounds (Exemplified Compounds H101, H201, and H301) were identified by MALDI-TOF-MS. Table 2 shows the results.

Synthesis Examples 22 to 25

Metal complexes were each synthesized by the same synthesis method as that of Synthesis Example 19 except that in Synthesis Example 19, the synthesis raw material was changed from quinolin-8-ol to a compound shown in Table 2 below. The structures of the resultant metal complexes were confirmed by the same method as that of Synthesis Example 19. Table 6 shows the results.

TABLE 2

| | Starting raw material | Synthesized metal complex |
|---|---|---|
| Synthesis Example 22 | [structure] | H119 |
| Synthesis Example 23 | [structure] | H126 |

TABLE 2-continued

| | Starting raw material | Synthesized metal complex |
|---|---|---|
| Synthesis Example 24 | [structure] | H129 |
| Synthesis Example 25 | [structure] | H130 |

Synthesis Examples 26 to 35

Metal complexes were each synthesized by the same synthesis method as that of Synthesis Example 20 except that in Synthesis Example 20, the synthesis raw material was changed from quinolin-8-ol to a compound shown in Table 3 below. The structures of the resultant metal complexes were confirmed by the same method as that of Synthesis Example 20. Table 6 shows the results.

TABLE 3

| | Starting raw material | Synthesized metal complex |
|---|---|---|
| Synthesis Example 26 | [structure] | H203 |
| Synthesis Example 27 | [structure] | H207 |
| Synthesis Example 28 | [structure] | H212 |
| Synthesis Example 29 | [structure] | H216 |

TABLE 3-continued

| | Starting raw material | Synthesized metal complex |
|---|---|---|
| Synthesis Example 30 | 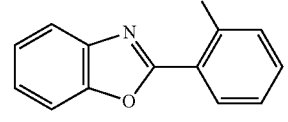 | H218 |

TABLE 4

| | Starting raw material | Synthesized metal complex |
|---|---|---|
| Synthesis Example 31 | | H219 |
| Synthesis Example 32 | | H226 |
| Synthesis Example 33 | | H229 |
| Synthesis Example 34 | | H230 |
| Synthesis Example 35 | | H236 |

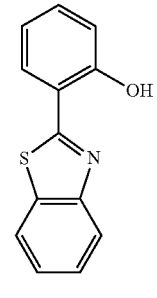 [SMILES: Oc1ccccc1-c1nc2ccccc2s1]

Synthesis Examples 36 to 38

Metal complexes were each synthesized by the same synthesis method as that of Synthesis Example 21 except that in Synthesis Example 21, the synthesis raw material was changed from quinolin-8-ol to a compound shown in Table 4 below. The structures of the resultant metal complexes were confirmed by the same method as that of Synthesis Example 21. Table 6 shows the results.

TABLE 5

| | Starting raw material | Synthesized metal complex |
|---|---|---|
| Synthesis Example 36 | | H303 |
| Synthesis Example 37 | | H316 |
| Synthesis Example 38 | | H318 |

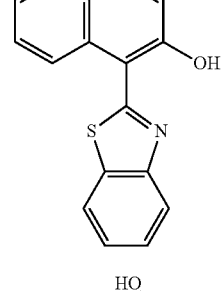

TABLE 6

| | Exemplified Compound | MS (calculated value) | MS (measured value) |
|---|---|---|---|
| Synthesis Example 19 | H101 | 312.07 | 312.33 |
| Synthesis Example 20 | H201 | 297.10 | 297.23 |
| Synthesis Example 21 | H301 | 352.02 | 352.08 |
| Synthesis Example 22 | H119 | 444.10 | 444.22 |
| Synthesis Example 23 | H126 | 476.05 | 476.34 |
| Synthesis Example 24 | H129 | 576.08 | 576.53 |
| Synthesis Example 25 | H130 | 576.08 | 576.57 |
| Synthesis Example 26 | H203 | 325.13 | 325.98 |
| Synthesis Example 27 | H207 | 397.13 | 397.67 |
| Synthesis Example 28 | H212 | 425.16 | 425.51 |
| Synthesis Example 29 | H216 | 659.28 | 659.33 |
| Synthesis Example 30 | H218 | 579.22 | 579.52 |
| Synthesis Example 31 | H219 | 429.12 | 429.46 |
| Synthesis Example 32 | H226 | 461.08 | 461.34 |
| Synthesis Example 33 | H229 | 561.11 | 561.87 |

TABLE 6-continued

| | Exemplified Compound | MS (calculated value) | MS (measured value) |
|---|---|---|---|
| Synthesis Example 34 | H230 | 561.11 | 561.87 |
| Synthesis Example 35 | H236 | 613.14 | 613.54 |
| Synthesis Example 36 | H303 | 380.05 | 380.11 |
| Synthesis Example 37 | H316 | 714.20 | 714.29 |
| Synthesis Example 38 | H318 | 579.22 | 579.53 |

Example 1

In this example, an organic light-emitting element having a construction in which "an anode/a hole-transporting layer/an electron-blocking layer/an emission layer/a hole-blocking layer/an electron-transporting layer/a cathode" were formed on a substrate in the stated order was produced by the following method.

First, ITO was formed into a film on a glass substrate and then subjected to desired patterning processing to form an ITO electrode (anode). At this time, the thickness of the ITO electrode was set to 100 nm. The substrate on which the ITO electrode had been thus formed was used as an ITO substrate in the following steps.

An organic light-emitting element was obtained by continuously forming, on the ITO substrate, organic compound layers and electrode layers shown in Table 7 below. It should be noted that at this time, the electrode area of the opposing electrode (metal electrode layers, cathode) was set to 3 mm$^2$.

TABLE 7

| | Material | Thickness [nm] |
|---|---|---|
| Hole-transporting layer: HTL | HT-2 | 40 |
| Electron-blocking layer: EBL | HT-7 | 10 |
| Emission layer Host: HOST Guest: GUEST | H226 (host) Ir-205 (guest) (H226:Ir-205 = 96:4 (weight ratio)) | 30 |
| Hole-blocking layer: HBL | ET-3 | 10 |
| Electron-transporting layer: ETL | ET-2 | 50 |
| First metal electrode layer | LiF | 0.5 |
| Second metal electrode layer | Al | 100 |

The characteristics of the resultant element were measured and evaluated by measuring its current-voltage characteristics with a microammeter 4140B manufactured by Hewlett-Packard Company and measuring its emission luminance with a BM7 manufactured by TOPCON CORPORATION. In this example, the light-emitting element had a maximum luminous wavelength of 619 nm and chromaticity (x, y) of (0.66, 0.34).

As a result, luminous efficiency when the organic light-emitting element of this example was caused to emit light with its luminance set to 2,000 cd/m$^2$ was 23.0 cd/A. In addition, the luminance half lifetime of the organic light-emitting element of this example at a current value of 100 mA/cm$^2$ was 300 hours.

Examples 2 to 22 and Comparative Examples 1 to 5

Organic light-emitting elements were each produced by the same method as that of Example 1 except that in Example 1, the compounds used as the hole-transporting layer (HTL), the electron-blocking layer (EBL), the emission layer host (HOST), the emission layer guest (GUEST), the hole-blocking layer (HBL), and the electron-transporting layer (ETL) were appropriately changed to compounds shown in Table 4 below. The characteristics of the resultant elements were measured and evaluated in the same manner as in Example 1. Table 8 shows the results of the measurement.

TABLE 8

| | HTL | EBL | HOST | GUEST | HBL | ETL | Luminous efficiency [cd/A] |
|---|---|---|---|---|---|---|---|
| Example 1 | HT1 | HT7 | H-226 | Ir-205 | ET-3 | ET-2 | 23.0 |
| Example 2 | HT1 | HT7 | H-119 | Ir-222 | ET-3 | ET-2 | 23.3 |
| Example 3 | HT1 | HT11 | H-126 | Ir-213 | ET-4 | ET-2 | 23.5 |
| Example 4 | HT1 | HT9 | H-129 | Ir-301 | ET-3 | ET-2 | 23.1 |
| Example 5 | HT1 | HT10 | H-201 | Ir-101 | ET-3 | ET-2 | 25.1 |
| Example 6 | HT1 | HT7 | H-201 | Ir-212 | ET-3 | ET-2 | 25.9 |
| Example 7 | HT1 | HT7 | H-203 | Ir-316 | ET-3 | ET-2 | 24.8 |
| Example 8 | HT2 | HT8 | H-207 | Ir-206 | ET-3 | ET-2 | 25.8 |
| Example 9 | HT2 | HT7 | H-207 | Ir-301 | ET-3 | ET-2 | 25.0 |
| Example 10 | HT2 | HT7 | H-218 | Ir-318 | ET-3 | ET-2 | 24.9 |
| Example 11 | HT2 | HT7 | H-219 | Ir-221 | ET-3 | ET-1 | 26.0 |
| Example 12 | HT1 | HT7 | H-226 | Ir-301 | ET-3 | ET-2 | 25.1 |
| Example 13 | HT1 | HT8 | H-226 | Ir-222 | ET-3 | ET-2 | 26.1 |
| Example 14 | HT1 | HT7 | H-229 | Ir-316 | ET-3 | ET-2 | 25.5 |
| Example 15 | HT2 | HT8 | H-229 | Ir-221 | ET-3 | ET-2 | 25.9 |
| Example 16 | HT2 | HT7 | H-230 | Ir-201 | ET-3 | ET-2 | 26.7 |
| Example 17 | HT2 | HT7 | H-236 | Ir-104 | ET-3 | ET-2 | 26.5 |
| Example 18 | HT2 | HT7 | H-236 | Ir-317 | ET-3 | ET-2 | 24.9 |
| Example 19 | HT2 | HT7 | H-301 | Ir-414 | ET-4 | ET-2 | 23.8 |
| Example 20 | HT2 | HT7 | H-303 | Ir-201 | ET-7 | ET-2 | 22.8 |
| Example 21 | HT1 | HT7 | H-316 | Ir-213 | ET-3 | ET-1 | 26.3 |
| Example 22 | HT1 | HT7 | H-318 | Ir-304 | ET-3 | ET-2 | 25.0 |
| Comparative Example 1 | HT1 | HT7 | H226 | RD3 | ET-3 | ET-2 | 13.2 |
| Comparative Example 2 | HT1 | HT7 | H226 | RD4 | ET-3 | ET-2 | 13.2 |
| Comparative Example 3 | HT1 | HT7 | EM9 | RD6 | ET-4 | ET-2 | 17.5 |
| Comparative Example 4 | HT1 | HT7 | EM8 | RD7 | ET-4 | ET-2 | 19.0 |
| Comparative Example 5 | HT1 | HT7 | EM9 | Ir-316 | ET-3 | ET-2 | 22.5 |

Each of the organic light-emitting elements of Comparative Examples 1 to 4 had a lower luminous efficiency than those of the organic light-emitting elements of Examples. This is caused by the fact that the guest in the emission layer is not the iridium complex (big-based Ir complex) represented by the general formula [1]. In addition, the organic light-emitting element of Comparative Example 5 has a lower luminous efficiency than those of the organic light-emitting elements of Examples, though the difference is slight. This can be said to be because the efficiency of energy transfer from the host to the guest is lower than that of each of the organic light-emitting elements of Examples.

In addition, the luminance half lifetimes of the organic light-emitting elements of Examples 1 to 22 at a current value of 100 mA/cm$^2$ were about 200 hours to 400 hours. In other words, the elements had long lifetimes.

Therefore, the organic light-emitting element of the present invention, specifically, the organic light-emitting element including the metal complex compound (host) lengthening the lifetime of the emission layer and the iridium complex represented by the general formula [1] (guest) imparting high luminous efficiency to the layer was found to have high luminous efficiency and a long lifetime.

Example 23

In this example, an organic light-emitting element having a construction in which "an anode/a hole-transporting layer/an electron-blocking layer/an emission layer/a hole-blocking layer/an electron-transporting layer/a cathode" were formed on a substrate in the stated order was produced. It should be noted that in this example, the emission layer contains an assist material.

First, organic compound layers and electrode layers shown in Table 9 below were continuously formed on an ITO substrate that had been produced by the same method as that of Example 1. It should be noted that at this time, the electrode area of the opposing electrode (metal electrode layers, cathode) was set to 3 mm².

TABLE 9

| | Material | Thickness (nm) |
|---|---|---|
| Hole-transporting layer: HTL | HT-2 | 40 |
| Electron-blocking layer: EBL | HT-7 | 10 |
| Emission layer | H-229 (host) | 30 |
| Host: HOST | HT-2 (assist) | |
| Assist: ASSIST | Ir-205 (guest) | |
| Guest: GUEST | (H-229:HT-2:Ir-205 = 80:15:5 (weight ratio)) | |
| Hole-blocking layer: HBL | ET-3 | 10 |
| Electron-transporting layer: ETL | ET-1 | 50 |
| First metal electrode layer | LiF | 0.5 |
| Second metal electrode layer | Al | 100 |

The characteristics of the resultant element were measured and evaluated in the same manner as in Example 1. Here, the organic light-emitting element of this example had a maximum luminous wavelength of 621 nm and chromaticity (x, y) of (0.66, 0.34). In addition, the element had a luminous efficiency at the time of its light emission at a luminance of 1,500 cd/m² of 35.2 cd/A and a luminance half lifetime at a current value of 100 mA/cm² of 230 hours.

Examples 24 to 31

Organic light-emitting elements were each produced by the same method as that of Example 23 except that in Example 23, the compounds used as the hole-transporting layer (HTL), the electron-blocking layer (EBL), the emission layer host (HOST), the emission layer assist (ASSIST), the emission layer guest (GUEST), the hole-blocking layer (HBL), and the electron-transporting layer (ETL) were changed as shown in Table 6. The characteristics of the resultant elements were measured and evaluated in the same manner as in Example 23. Table 9 shows the results of the measurement.

TABLE 10

| | HTL | EBL | HOST | ASSIST | GUEST | HBL | ETL | Luminous efficiency at 1,500 cd/m² [cd/A] |
|---|---|---|---|---|---|---|---|---|
| Example 24 | HT2 | HT7 | H-229 | HT2 | Ir-205 | ET-3 | ET-2 | 35.2 |
| Example 25 | HT2 | HT7 | H-129 | HT2 | Ir-318 | ET-7 | ET-2 | 30.2 |
| Example 26 | HT2 | HT11 | H-201 | GD6 | Ir-222 | ET-3 | ET-2 | 37.3 |
| Example 27 | HT1 | HT8 | H-219 | GD6 | Ir-206 | ET-4 | ET-1 | 32.8 |
| Example 28 | HT2 | HT7 | H-226 | H-226 | Ir-214 | ET-3 | ET-2 | 38.3 |
| Example 29 | HT2 | HT7 | H-229 | H-229 | Ir-316 | ET-3 | ET-2 | 35.8 |
| Example 30 | HT3 | HT8 | H-236 | HT2 | Ir-301 | ET-4 | ET-2 | 32.4 |
| Example 31 | HT2 | HT7 | H-318 | GD6 | Ir-221 | ET-3 | ET-2 | 34.1 |

The foregoing shows that the organic light-emitting element of the present invention, whose emission layer contains the metal complex compound exhibiting a lifetime-lengthening effect and the big-based Ir complex imparting high luminous efficiency, is an organic light-emitting element having high luminous efficiency and a long luminance half lifetime. In addition, the luminance half lifetimes of the organic light-emitting elements of Examples 23 to 31 at a current value of 100 mA/cm² were about 200 hours to 350 hours, and hence the elements were found to be long-lifetime and high-performance light-emitting elements.

As described above with reference to the embodiments and Examples, according to the present invention, it is possible to provide the organic light-emitting element having high luminous efficiency and a long lifetime.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-285621, filed on Dec. 27, 2012, which is hereby incorporated by reference herein in its entirety.

The invention claimed is:

1. An organic light-emitting element comprising:
a pair of electrodes; and
an organic compound layer placed between the pair of electrodes,
wherein the organic compound layer includes an iridium complex represented by the following general formula [1] and a metal complex compound represented by the following general formula [5]:

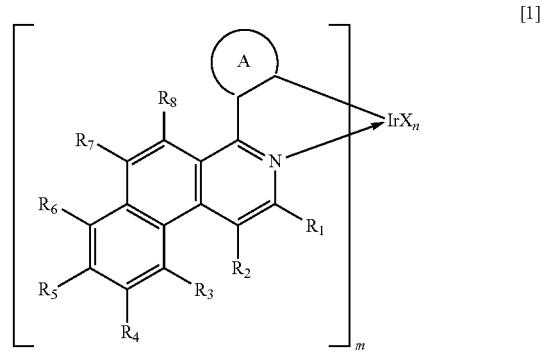

[1]

in the formula [1]:
  R₁ to R₈ each represents a hydrogen atom, a halogen atom, a cyano group, an alkyl group, an alkoxy group, a substituted amino group, a substituted or unsubstituted aromatic hydrocarbon group, or a substituted or unsubstituted heteroaromatic group;
  m represents an integer of 1 to 3 and n represents an integer of 0 to 2, provided that m+n equals 3;
  ring A represents a cyclic structure selected from the group consisting of a benzene ring, a naphthalene ring, a phenanthrene ring, a fluorene ring, a 9,9-spirobifluorene ring and a chrysene ring, and is covalently bonded to a benzo[f]isoquinoline skeleton and an Ir metal, and the ring A may further have a substituent;
  X represents a bidentate ligand; and
  a partial structure IrX_n is selected from any one of structures represented by the following general formulae [2] to [4]:

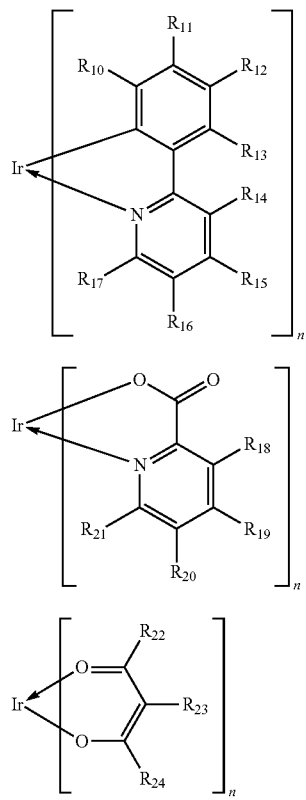

in the formulae [2] to [4]:
  R₁₀ to R₂₄ each represents a hydrogen atom, a halogen atom, a substituted or unsubstituted alkyl group, an alkoxy group, an aryloxy group, an aralkyl group, a substituted amino group, a substituted or unsubstituted aromatic hydrocarbon group, or a substituted or unsubstituted heteroaromatic group, and when n represents 2, multiple substituents represented by any one of R₁₀ to R₂₄ may be identical to or different from each other;

$$ML_2 \quad [5]$$

in the formula [5]:
  M represents a divalent metal atom selected from the group consisting of beryllium, magnesium and zinc;
  L represents a bidentate ligand; and when M represents beryllium or magnesium, a partial structure ML comprises any one of structures represented by the following general formulae [8] to [11], and when M represents zinc, the partial structure ML comprises any one of the structures represented by the following general formulae [8] to [9]:

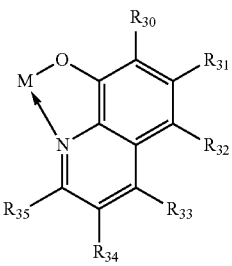

[6]

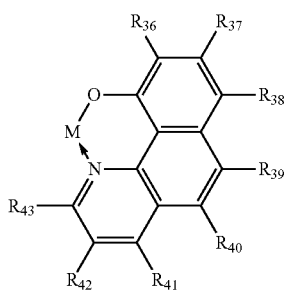

[7]

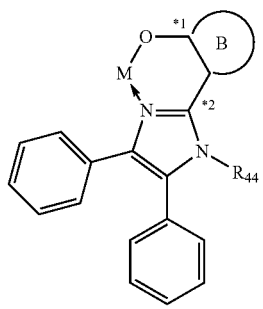

[8]

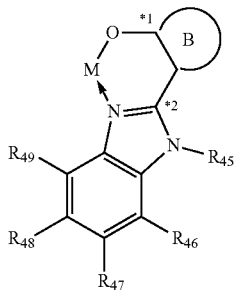

[9]

103
-continued

[10]
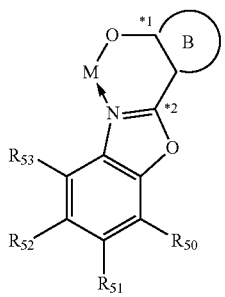

[11]
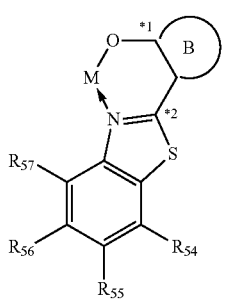

in the formulae [8] to [11]:

$R_{30}$ to $R_{57}$ each represents a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group, in the formulae [8] to [11]:

a ring B comprises any one of cyclic structures represented by the following general formulae [12] to [14]; and

*1 represents a bonding position with an oxygen atom and *2 represents a bonding position with a carbon atom in a heterocyclic five-membered ring skeleton:

[12]
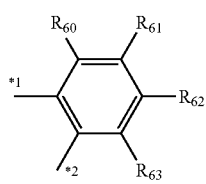

[13]
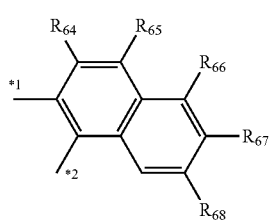

104
-continued

[14]
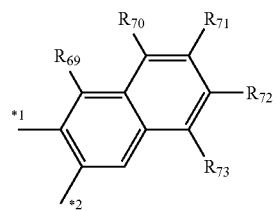

in the formulae [12] to [14]:

$R_{60}$ to $R_{73}$ each represents a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

2. The organic light-emitting element according to claim 1, wherein $R_1$ to $R_8$, $R_{10}$ to $R_{24}$, $R_{30}$ to $R_{57}$, and $R_{60}$ to $R_{73}$ each represents a hydrogen atom, an alkyl group having 1 to 4 carbon atoms, or a phenyl group that may be substituted with an alkyl group having 1 to 4 carbon atoms.

3. The organic light-emitting element according to claim 1, wherein m represents 2 and n represents 1.

4. The organic light-emitting element according to claim 1, wherein the iridium complex represented by the general formula [1] comprises a compound represented by the following general formula [15]:

[15]
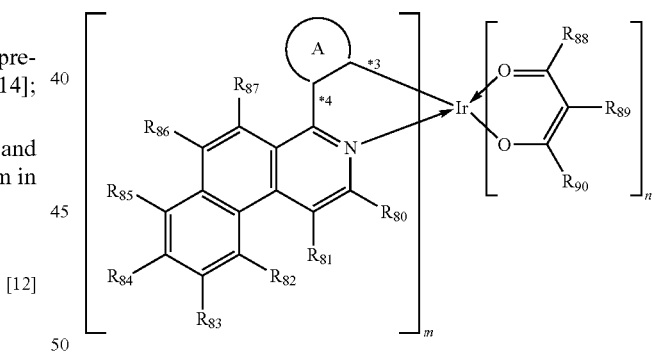

in the formula [15]:

$R_{80}$ to $R_{90}$ each represents a hydrogen atom, a halogen atom, a cyano group, an alkyl group, an alkoxy group, a substituted amino group, a substituted or unsubstituted aromatic hydrocarbon group, or a substituted or unsubstituted heteroaromatic group;

m represents an integer of 1 to 3 and n represents an integer of 0 to 2, provided that m+n equals 3;

*3 represents a bond between the ring A and the Ir metal, and *4 represents a bond between the ring A and a carbon atom at a 1-position in the benzo[f]isoquinoline skeleton; and the ring A comprises any one of structures represented by the following general formulae [16] to [20]:

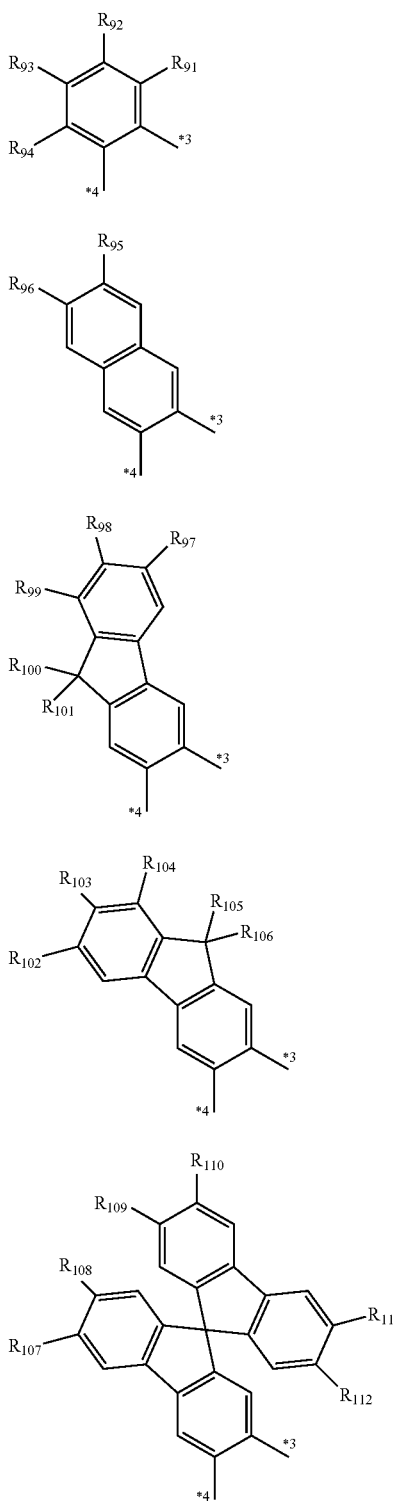

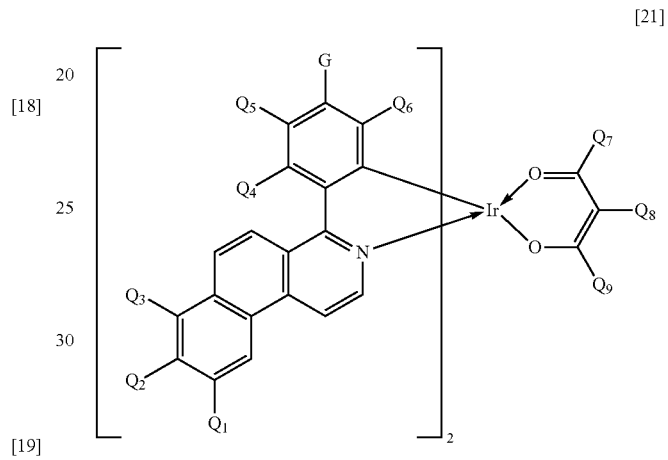

in the formulae [16] to [20]:

R$_{91}$ to R$_{112}$ each represents a hydrogen atom, a halogen atom, an alkyl group, an alkoxy group, a substituted amino group, a substituted or unsubstituted aromatic hydrocarbon group, or a substituted or unsubstituted heteroaromatic group; and

*3 represents a bonding position with the Ir metal and *4 represents a bonding position with the carbon atom at the 1-position in the benzo[f]isoquinoline skeleton.

5. The organic light-emitting element according to claim 3, wherein the ring A comprises the structure represented by the general formula [16].

6. The organic light-emitting element according to claim 4, wherein R$_{80}$ to R$_{90}$, and R$_{91}$ to R$_{112}$ each represents a hydrogen atom, an alkyl group having 1 to 4 carbon atoms, or a phenyl group that may be substituted with an alkyl group having 1 to 4 carbon atoms.

7. The organic light-emitting element according to claim 1, wherein the iridium complex represented by the general formula [1] comprises an iridium complex represented by the following general formula [21]:

in the formula [21]:

Q$_1$ to Q$_9$ each represents a hydrogen atom, a halogen atom, an alkyl group, an alkoxy group, a trifluoromethyl group, or a cyano group; and G represents a hydrogen atom, a halogen atom, an alkyl group, an alkoxy group, a trifluoromethyl group, a cyano group, or a substituted or unsubstituted phenyl group.

8. The organic light-emitting element according to claim 7, wherein Q$_1$ to Q$_9$ each represents a hydrogen atom, an alkyl group having 1 to 4 carbon atoms, or a phenyl group that may be substituted with an alkyl group having 1 to 4 carbon atoms.

9. The organic light-emitting element according to claim 1, wherein:
the organic compound layer comprises an emission layer including a host and a guest;
the guest comprises the iridium complex represented by the general formula [1]; and
the host comprises the metal complex compound represented by the general formula [5].

10. The organic light-emitting element according to claim 9, wherein the organic compound layer further includes an assist material different from the host and the guest.

11. The organic light-emitting element according to claim 10, wherein the assist material comprises an iridium complex.

12. The organic light-emitting element according to claim 1, wherein the organic light-emitting element emits red light.

13. The organic light-emitting element according to claim 1, further comprising an active element connected to the organic light-emitting element.

14. The organic light-emitting element according to claim 1, further comprising a substrate and other organic light-emitting elements on the substrate.

15. A display apparatus comprising multiple pixels, wherein each pixel has the organic light-emitting element according to claim 1 and an active element connected to the organic light-emitting element.

16. An information processing apparatus comprising:
a display portion for displaying an image; and
an input portion for inputting image information,
wherein the display portion comprises the display apparatus according to claim 15.

17. A lighting apparatus comprising:
the organic light-emitting element according to claim 1; and
an AC/DC converter circuit connected to the organic light-emitting element.

18. The display apparatus according to claim 15, wherein an electrode of the active element is formed of a transparent oxide semiconductor.

19. An image-forming apparatus comprising:
a photosensitive member;
charging unit for charging a surface of the photosensitive member;
exposing unit for exposing the photosensitive member to form an electrostatic latent image; and
developing unit for developing the electrostatic latent image formed on the surface of the photosensitive member,
wherein the exposing unit includes the organic light-emitting element according to claim 1.

20. An exposing apparatus for exposing a photosensitive member comprising a plurality of the organic light-emitting elements according to claim 1, wherein the organic light-emitting elements are placed to form a line along a predetermined direction.

* * * * *